(12) United States Patent
Matsuyama et al.

(10) Patent No.: US 11,535,647 B2
(45) Date of Patent: Dec. 27, 2022

(54) PEPTIDE PURIFICATION METHOD USING SULFONATE COMPOUND

(71) Applicant: NAGASE & CO., LTD., Osaka (JP)

(72) Inventors: Keisuke Matsuyama, Kobe (JP); Kenichiro Yamamoto, Ibaraki (JP); Sayoko Murakami, Ibaraki (JP)

(73) Assignee: NAGASE & CO., LTD., Osaka (JP)

( * ) Notice: Subject to any disclaimer, the term of this patent is extended or adjusted under 35 U.S.C. 154(b) by 0 days.

(21) Appl. No.: 17/275,938

(22) PCT Filed: Aug. 8, 2019

(86) PCT No.: PCT/JP2019/031405
§ 371 (c)(1),
(2) Date: Mar. 12, 2021

(87) PCT Pub. No.: WO2020/054287
PCT Pub. Date: Mar. 19, 2020

(65) Prior Publication Data
US 2022/0144888 A1 May 12, 2022

(30) Foreign Application Priority Data

Sep. 14, 2018 (JP) .............................. JP2018-173042
Jan. 22, 2019 (JP) .............................. JP2019-008701

(51) Int. Cl.
  *C07K 1/00* (2006.01)
  *C07K 1/30* (2006.01)
(52) U.S. Cl.
  CPC ...................... *C07K 1/30* (2013.01)
(58) Field of Classification Search
  CPC ...................................................... C07K 1/30
  See application file for complete search history.

(56) References Cited

U.S. PATENT DOCUMENTS

| | | | |
|---|---|---|---|
| 4,581,168 | A | 4/1986 | Diaz et al. |
| 6,251,625 | B1 | 6/2001 | Bommarius et al. |
| 6,663,869 | B1 | 12/2003 | Rose et al. |
| 2004/0029781 | A1 | 2/2004 | Hernan et al. |
| 2008/0193981 | A1 | 8/2008 | Fahrner et al. |
| 2008/0262207 | A1 | 10/2008 | Duffin et al. |
| 2008/0287650 | A1 | 11/2008 | Tovi et al. |
| 2013/0102761 | A1 | 4/2013 | Liao et al. |
| 2014/0005121 | A1 | 1/2014 | Chakraborty et al. |
| 2014/0336355 | A1 | 11/2014 | Arendt et al. |
| 2016/0347789 | A1 | 12/2016 | Felle et al. |

FOREIGN PATENT DOCUMENTS

| | | |
|---|---|---|
| CA | 1340353 C | 1/1999 |
| CN | 1193997 A | 9/1998 |
| CN | 1222916 A | 7/1999 |
| CN | 101759776 A | 6/2010 |
| CN | 101796064 A | 8/2010 |
| CN | 101899092 A | 12/2010 |
| CN | 106905381 A | 6/2017 |
| EP | 0 333 036 | 9/1989 |
| JP | 10-87695 A | 4/1998 |
| JP | 2013-501773 A | 1/2013 |
| JP | 2016-190851 A | 11/2016 |
| JP | 2018-52933 A | 4/2018 |
| WO | WO 2011/018745 A1 | 2/2011 |
| WO | WO 2011/150110 A | 12/2011 |
| WO | WO 2014/094957 | 6/2014 |
| WO | WO 2016/071872 A1 | 5/2016 |

OTHER PUBLICATIONS

Bergot et al. (User Bulletin No. 16, Peptide Synthesizer, Applied Biosystems, 2002.*
Combined Chinese Office Action and Search Report dated Aug. 9, 2021 in Patent Application No. 2019800432843 (with English language translation), 21 pages.
Maiqian Nie, "Organic Chemistry: Sulfonic Acids," Metallurgical Industry Press, 2nd edition, Jan. 2014, 16 pages.
International Search Report dated Nov. 5, 2519 in PCT/JP2019/031405 (with English translation), 10 pages.
International Preliminary Report on Patentability and Written Opinion dated Mar. 9, 2021 in PCT/JP2019/031405 (with English translation), 14 pages.
Taiwanese Search Report dated Jan. 29, 2021 in Taiwanese Patent Application No. 108128238 (with English translation), 2 pages.
Lougnot, D. -J., et al., "A water-soluble benzophenone in reverse micelles: Kinetics and Spectroscopy", Journal of Photochemistry, 1984, vol. 26, pp. 119-130.
Bigger, S. W., et al., "FlashPhotol: Using a flash photolysis apparatus simulator to introduce students to the kinetics of translent species and fast reactions", J. Chem. Educ., 2016, vol. 93, pp. 1475-1477.
Nahor, G. S., et al., "Reduction of dinitrogen to ammonia in aqueous solution mediated by colloidal metals", J. Chem. Soc. Faraday Trans., 1990, vol. 86, No. 23, pp. 3927-3933.
Garber, L.T., et al., "Peptide crystal growth via sulfonate salt formation: The structure of bis-glycylglycine-1, 5-napthaienedisulfonate hydrate", Letters in Peptide Science, 1994, 1, pp. 127-133.
Decision to Grant a Patent dated May 20, 2019, in Japanese Patent Application No. 2019-008701 (with English translation).
Notice of Reasons for Refusal dated Feb. 12, 2019, in Japanese Patent Application No. 2019-008701 (with machine English translation).

(Continued)

*Primary Examiner* — Jeanette M Lieb
(74) *Attorney, Agent, or Firm* — Oblon, McClelland, Maier & Neustadt, L.L.P.

(57) ABSTRACT

A method for purifying a target peptide may include mixing a peptide product obtained through a peptide synthesis with a solvent in the presence of a sulfonic acid compound to obtain a solid; and performing a solid-liquid separation to collect the solid.

24 Claims, No Drawings
Specification includes a Sequence Listing.

(56) References Cited

OTHER PUBLICATIONS

GL Sciences Inc., Good Usage of HPLC, Chapter II-5 ion-pair reagents (https://www.gls.co.ip/technique/technique_data/ic/usage_of_hplc/P2_5.html> (with English Machine Translation).
Chromatographia, vol. 20, No. 10, p. 587-590 (Oct. 1985).
Supplementary European Search Report dated Jun. 23. 2022, in corresponding European Patent Application No. 19860341.7.

* cited by examiner

SEQUENCE LISTING

```
<160> NUMBER OF SEQ ID NOS: 63

<210> SEQ ID NO 1
<211> LENGTH: 6
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 1
```

Tyr Phe Tyr Pro Glu Leu
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (6)..(6)
<223> OTHER INFORMATION: AMIDATION

<400> SEQUENCE: 2

Tyr Phe Tyr Pro Glu Leu
1               5

<210> SEQ ID NO 3
<211> LENGTH: 16
<212> TYPE: PRT
<213> ORGANISM: Artificial sequence
<220> FEATURE:
<223> OTHER INFORMATION: Synthetic Peptide

<400> SEQUENCE: 3

Val Ile Arg Ala Leu Arg Arg Ala Leu Val Ala Leu Arg Ala Leu Arg
1               5                   10                  15

<210> SEQ ID NO 4
<211> LENGTH: 19
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (19)..(19)
<223> OTHER INFORMATION: AMIDATION

<400> SEQUENCE: 4

Ala Arg Leu Asp Val Ala Ser Glu Phe Arg Lys Lys Trp Asn Lys Ala
1               5                   10                  15

Leu Ser Arg

<210> SEQ ID NO 5
<211> LENGTH: 31
<212> TYPE: PRT
<213> ORGANISM: Artificial sequence
<220> FEATURE:
<223> OTHER INFORMATION: Synthetic Peptide

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 6
<211> LENGTH: 14
<212> TYPE: PRT
<213> ORGANISM: Artificial sequence
<220> FEATURE:
<223> OTHER INFORMATION: Synthetic Peptide

<400> SEQUENCE: 6

Ala Gly Cys Lys Asn Phe Phe Trp Lys Thr Phe Thr Ser Cys

```
1               5                   10
```

<210> SEQ ID NO 7
<211> LENGTH: 8
<212> TYPE: PRT
<213> ORGANISM: Artificial sequence
<220> FEATURE:
<223> OTHER INFORMATION: Synthetic Peptide

<400> SEQUENCE: 7

```
Ala Gln Lys Leu Arg Ala Ser Asp
1               5
```

<210> SEQ ID NO 8
<211> LENGTH: 8
<212> TYPE: PRT
<213> ORGANISM: Artificial sequence
<220> FEATURE:
<223> OTHER INFORMATION: Synthetic Peptide

<400> SEQUENCE: 8

```
Tyr Glu Arg Ala Lys Ser Asn Met
1               5
```

<210> SEQ ID NO 9
<211> LENGTH: 25
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (25)..(25)
<223> OTHER INFORMATION: AMIDATION

<400> SEQUENCE: 9

```
Phe Arg Val Asp Glu Glu Phe Gln Ser Pro Phe Ala Ser Gln Ser Arg
1               5                   10                  15

Gly Tyr Phe Leu Phe Arg Pro Arg Asn
            20                  25
```

<210> SEQ ID NO 10
<211> LENGTH: 5
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 10

```
Gly Gly Gly Arg Gly
1               5
```

<210> SEQ ID NO 11
<211> LENGTH: 5
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)

```
<223> OTHER INFORMATION: AMIDATION

<400> SEQUENCE: 11

Ala Leu Arg Ala Leu
1               5

<210> SEQ ID NO 12
<211> LENGTH: 5
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 12

Ala Leu Arg Ala Leu
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic Peptide

<400> SEQUENCE: 13

Ala Leu Arg Ala Leu Arg Ala Leu Arg
1               5

<210> SEQ ID NO 14
<211> LENGTH: 5
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: AMIDATION

<400> SEQUENCE: 14

Gly Gly Arg Gly Gly
1               5

<210> SEQ ID NO 15
<211> LENGTH: 27
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (27)..(27)
<223> OTHER INFORMATION: AMIDATION

<400> SEQUENCE: 15

His Ser Asp Gly Thr Phe Thr Ser Glu Leu Ser Arg Leu Arg Glu Gly
1               5                   10                  15

Ala Arg Leu Gln Arg Leu Leu Gln Gly Leu Val
            20                  25
```

```
<210> SEQ ID NO 16
<211> LENGTH: 5
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: AMIDATION

<400> SEQUENCE: 16

Tyr Tyr Pro Glu Leu
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 17

Tyr Tyr Pro Glu Leu
1               5

<210> SEQ ID NO 18
<211> LENGTH: 15
<212> TYPE: PRT
<213> ORGANISM: Artificial sequence
<220> FEATURE:
<223> OTHER INFORMATION: Synthetic Peptide

<400> SEQUENCE: 18

Val Ile Arg Ala Leu Arg Ala Leu Val Ala Leu Arg Ala Leu Arg
1               5                   10                  15

<210> SEQ ID NO 19
<211> LENGTH: 18
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (18)..(18)
<223> OTHER INFORMATION: AMIDATION

<400> SEQUENCE: 19

Ala Arg Leu Asp Val Ala Ser Glu Phe Arg Lys Lys Asn Lys Ala Leu
1               5                   10                  15

Ser Arg

<210> SEQ ID NO 20
<211> LENGTH: 30
<212> TYPE: PRT
<213> ORGANISM: Artificial sequence
<220> FEATURE:
<223> OTHER INFORMATION: Synthetic Peptide

<400> SEQUENCE: 20
```

His Ala Glu Gly Thr Phe Thr Ser Asp Val Ser Ser Tyr Leu Glu Gly
1               5                   10                  15

Gln Ala Ala Lys Glu Phe Ala Trp Leu Val Lys Gly Arg Gly
            20              25              30

<210> SEQ ID NO 21
<211> LENGTH: 13
<212> TYPE: PRT
<213> ORGANISM: Artificial sequence
<220> FEATURE:
<223> OTHER INFORMATION: Synthetic Peptide

<400> SEQUENCE: 21

Ala Gly Cys Lys Asn Phe Phe Trp Lys Thr Phe Thr Ser
1               5                   10

<210> SEQ ID NO 22
<211> LENGTH: 7
<212> TYPE: PRT
<213> ORGANISM: Artificial sequence
<220> FEATURE:
<223> OTHER INFORMATION: Synthetic Peptide

<400> SEQUENCE: 22

Ala Gln Lys Leu Arg Ala Asp
1               5

<210> SEQ ID NO 23
<211> LENGTH: 6
<212> TYPE: PRT
<213> ORGANISM: Artificial sequence
<220> FEATURE:
<223> OTHER INFORMATION: Synthetic Peptide

<400> SEQUENCE: 23

Ala Lys Leu Arg Ala Asp
1               5

<210> SEQ ID NO 24
<211> LENGTH: 7
<212> TYPE: PRT
<213> ORGANISM: Artificial sequence
<220> FEATURE:
<223> OTHER INFORMATION: Synthetic Peptide

<400> SEQUENCE: 24

Gln Lys Leu Arg Ala Ser Asp
1               5

<210> SEQ ID NO 25
<211> LENGTH: 7
<212> TYPE: PRT
<213> ORGANISM: Artificial sequence
<220> FEATURE:
<223> OTHER INFORMATION: Synthetic Peptide

<400> SEQUENCE: 25

Ala Gln Lys Leu Arg Ser Asp
1               5

<210> SEQ ID NO 26
<211> LENGTH: 7
<212> TYPE: PRT
<213> ORGANISM: Artificial sequence
<220> FEATURE:
<223> OTHER INFORMATION: Synthetic Peptide

```
<400> SEQUENCE: 26

Ala Gln Lys Leu Arg Ala Ser
1               5

<210> SEQ ID NO 27
<211> LENGTH: 7
<212> TYPE: PRT
<213> ORGANISM: Artificial sequence
<220> FEATURE:
<223> OTHER INFORMATION: Synthetic Peptide

<400> SEQUENCE: 27

Ala Gln Lys Arg Ala Ser Asp
1               5

<210> SEQ ID NO 28
<211> LENGTH: 7
<212> TYPE: PRT
<213> ORGANISM: Artificial sequence
<220> FEATURE:
<223> OTHER INFORMATION: Synthetic Peptide

<400> SEQUENCE: 28

Ala Gln Lys Leu Ala Ser Asp
1               5

<210> SEQ ID NO 29
<211> LENGTH: 7
<212> TYPE: PRT
<213> ORGANISM: Artificial sequence
<220> FEATURE:
<223> OTHER INFORMATION: Synthetic Peptide

<400> SEQUENCE: 29

Tyr Glu Arg Ala Lys Asn Met
1               5

<210> SEQ ID NO 30
<211> LENGTH: 7
<212> TYPE: PRT
<213> ORGANISM: Artificial sequence
<220> FEATURE:
<223> OTHER INFORMATION: Synthetic Peptide

<400> SEQUENCE: 30

Tyr Glu Arg Lys Ser Asn Met
1               5

<210> SEQ ID NO 31
<211> LENGTH: 7
<212> TYPE: PRT
<213> ORGANISM: Artificial sequence
<220> FEATURE:
<223> OTHER INFORMATION: Synthetic Peptide

<400> SEQUENCE: 31

Tyr Glu Arg Ala Ser Asn Met
1               5

<210> SEQ ID NO 32
<211> LENGTH: 7
<212> TYPE: PRT
<213> ORGANISM: Artificial sequence
<220> FEATURE:
<223> OTHER INFORMATION: Synthetic Peptide

<400> SEQUENCE: 32
```

Tyr Glu Arg Ala Lys Ser Met
1               5

<210> SEQ ID NO 33
<211> LENGTH: 7
<212> TYPE: PRT
<213> ORGANISM: Artificial sequence
<220> FEATURE:
<223> OTHER INFORMATION: Synthetic Peptide

<400> SEQUENCE: 33

Glu Arg Ala Lys Ser Asn Met
1               5

<210> SEQ ID NO 34
<211> LENGTH: 7
<212> TYPE: PRT
<213> ORGANISM: Artificial sequence
<220> FEATURE:
<223> OTHER INFORMATION: Synthetic Peptide

<400> SEQUENCE: 34

Tyr Glu Arg Ala Lys Ser Asn
1               5

<210> SEQ ID NO 35
<211> LENGTH: 7
<212> TYPE: PRT
<213> ORGANISM: Artificial sequence
<220> FEATURE:
<223> OTHER INFORMATION: Synthetic Peptide

<400> SEQUENCE: 35

Tyr Arg Ala Lys Ser Asn Met
1               5

<210> SEQ ID NO 36
<211> LENGTH: 24
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (24)..(24)
<223> OTHER INFORMATION: AMIDATION

<400> SEQUENCE: 36

Phe Arg Val Asp Glu Glu Phe Gln Ser Pro Phe Ala Ser Gln Ser Arg
1               5                   10                  15

Gly Tyr Phe Leu Phe Arg Arg Asn
            20

<210> SEQ ID NO 37
<211> LENGTH: 4
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 37

Gly Gly Gly Gly
1

```
<210> SEQ ID NO 38
<211> LENGTH: 4
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 38

Ala Leu Ala Leu
1

<210> SEQ ID NO 39
<211> LENGTH: 4
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 39

Ala Leu Ala Leu
1

<210> SEQ ID NO 40
<211> LENGTH: 8
<212> TYPE: PRT
<213> ORGANISM: Artificial sequence
<220> FEATURE:
<223> OTHER INFORMATION: Synthetic Peptide

<400> SEQUENCE: 40

Ala Leu Ala Leu Arg Ala Leu Arg
1               5

<210> SEQ ID NO 41
<211> LENGTH: 4
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 41

Gly Gly Gly Gly
1

<210> SEQ ID NO 42
<211> LENGTH: 26
<212> TYPE: PRT
<213> ORGANISM: Artificial sequence
<220> FEATURE:
```

```
<223> OTHER INFORMATION: Synthetic Peptide
<220> FEATURE:
<221> NAME/KEY: MOD_RES
<222> LOCATION: (26)..(26)
<223> OTHER INFORMATION: AMIDATION

<400> SEQUENCE: 42

His Ser Asp Gly Thr Phe Thr Ser Glu Leu Ser Arg Leu Glu Gly Ala
1               5                   10                  15
Arg Leu Gln Arg Leu Leu Gln Gly Leu Val
            20                  25

<210> SEQ ID NO 43
<211> LENGTH: 9
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = Pyr = pyroglutamic acid
<220> FEATURE:
<221> NAME/KEY: MOD_RES
<222> LOCATION: (9)..(9)
<223> OTHER INFORMATION: AMIDATION

<400> SEQUENCE: 43

Xaa His Trp Ser Tyr Leu Leu Arg Pro
1               5

<210> SEQ ID NO 44
<211> LENGTH: 5
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 44

His Val Thr Thr Val
1               5

<210> SEQ ID NO 45
<211> LENGTH: 4
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 45

Val Thr Thr Val
1

<210> SEQ ID NO 46
<211> LENGTH: 8
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (8)..(8)
```

```
<223> OTHER INFORMATION: AMIDATION

<400> SEQUENCE: 46

Tyr Glu Arg Ala Lys Ser Asn Met
1               5

<210> SEQ ID NO 47
<211> LENGTH: 8
<212> TYPE: PRT
<213> ORGANISM: Artificial sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: AMIDATION

<400> SEQUENCE: 47

Tyr Glu Arg Ala Lys Ser Asn Leu
1               5

<210> SEQ ID NO 48
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (10)..(10)
<223> OTHER INFORMATION: AMIDATION

<400> SEQUENCE: 48

Val Lys Arg Glu Ser Tyr Ser Gly Val Thr
1               5                   10

<210> SEQ ID NO 49
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 49

Arg Ala Val Leu Pro
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = RC8 = ((R)-alpha-(7-octenyl)alanine)
<220> FEATURE:
<221> NAME/KEY: MISC_FEATURE
<222> LOCATION: (5)..(5)
<223> OTHER INFORMATION: Xaa = (Me)F = N-Methylphenylalanine
<220> FEATURE:
<221> NAME/KEY: MISC_FEATURE
<222> LOCATION: (7)..(7)
<223> OTHER INFORMATION: Xaa = SC5 = ((S)-alpha-(4-pentenyl)alanine)

<400> SEQUENCE: 50

Xaa Arg Arg Arg Xaa Arg Xaa
1               5
```

```
<210> SEQ ID NO 51
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: AMIDATION

<400> SEQUENCE: 51

His Tyr Phe Tyr Pro Glu Leu
1               5

<210> SEQ ID NO 52
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (11)..(11)
<223> OTHER INFORMATION: AMIDATION

<400> SEQUENCE: 52

Trp Pro Val Thr Leu Asn Ala Gln Thr Ile Asp
1               5                   10

<210> SEQ ID NO 53
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa = (Me)G = N-Methylglycine
<220> FEATURE:
<221> NAME/KEY: MISC_FEATURE
<222> LOCATION: (5)..(5)
<223> OTHER INFORMATION: Xaa = Dap = diaminopropionic acid

<400> SEQUENCE: 53

Thr Xaa Arg Lys Xaa His
1               5

<210> SEQ ID NO 54
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = Pyr = pyroglutamic acid
<220> FEATURE:
<221> NAME/KEY: MOD_RES
<222> LOCATION: (17)..(17)
<223> OTHER INFORMATION: AMIDATION

<400> SEQUENCE: 54

Xaa Gly Pro Trp Leu Glu Glu Glu Glu Glu Ala Tyr Gly Trp Met Asp
1               5                   10                  15
```

Phe

<210> SEQ ID NO 55
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: AMIDATION

<400> SEQUENCE: 55

Val Lys Arg Glu Ser Tyr Ser Gly Val
1               5

<210> SEQ ID NO 56
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 56

Arg Ala Leu Pro
1

<210> SEQ ID NO 57
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = RC8 = ((R)-alpha-(7-octenyl)alanine)
<220> FEATURE:
<221> NAME/KEY: MOD_RES
<222> LOCATION: (6)..(6)
<223> OTHER INFORMATION: AMIDATION
<220> FEATURE:
<221> NAME/KEY: MISC_FEATURE
<222> LOCATION: (6)..(6)
<223> OTHER INFORMATION: Xaa = SC5 = ((S)-alpha-(4-pentenyl)alanine)

<400> SEQUENCE: 57

Xaa Arg Arg Arg Arg Xaa
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 58

His Tyr Tyr Pro Glu Leu
1               5

```
<210> SEQ ID NO 59
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (10)..(10)
<223> OTHER INFORMATION: AMIDATION

<400> SEQUENCE: 59

Pro Val Thr Leu Asn Ala Gln Thr Ile Asp
1               5                   10

<210> SEQ ID NO 60
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = (Me)G = N-Methylglycine
<220> FEATURE:
<221> NAME/KEY: MISC_FEATURE
<222> LOCATION: (4)..(4)
<223> OTHER INFORMATION: Xaa = Dap = (S)-diaminopropionic acid

<400> SEQUENCE: 60

Xaa Arg Lys Xaa His
1               5

<210> SEQ ID NO 61
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = Pyr = pyroglutamic acid
<220> FEATURE:
<221> NAME/KEY: MOD_RES
<222> LOCATION: (16)..(16)
<223> OTHER INFORMATION: AMIDATION

<400> SEQUENCE: 61

Xaa Gly Pro Trp Leu Glu Glu Glu Glu Tyr Gly Trp Met Asp Phe
1               5                   10                  15

<210> SEQ ID NO 62
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 62

Tyr His Tyr Pro Glu Leu
1               5
```

```
<210> SEQ ID NO 63
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = MeK = alpha-Methyllysine
<220> FEATURE:
<221> NAME/KEY: MOD_RES
<222> LOCATION: (6)..(6)
<223> OTHER INFORMATION: AMIDATION

<400> SEQUENCE: 63

Tyr Xaa Tyr Pro Glu Leu
1               5
```

PEPTIDE PURIFICATION METHOD USING SULFONATE COMPOUND

TECHNICAL FIELD

The present application relates to a method for purifying a target peptide from peptide product obtained by peptide synthesis, and a medicament comprising the target peptide obtained by the purification method.

BACKGROUND ART

Peptides with relatively few amino acid residues (usually less than or equal to 30 residues) are commonly produced by organic chemical synthesis (for example, Patent Document 1). Examples of the organic chemical synthesis method include solid-phase and liquid-phase methods, in which peptide elongation reactions consisting of coupling reaction of N-protected amino acid with C-protected peptide (C-protected amino acid in a case of dipeptide formation) followed by N-terminal deprotection reaction are repeated. In the organic chemical synthesis methods, since various analogue peptides are also synthesized due to partial duplication, partial omission, etc. of the peptide elongation reaction, it is required to separate the generated target peptide from these analogue peptides. However, the physicochemical properties of analogue peptides are often very similar to those of the target peptide, making their separation very difficult. It is desired to provide a method for effectively separating a target peptide and analogue peptides in order to obtain a purified target peptide.

Peptides comprising more amino acid residues (usually over 30 residues) are commonly produced by fermentation (for example, Patent Document 2). In this case, analogue peptides, for example, having amino acid replacement(s) may contaminate the target one, and the separation of these peptides having very similar properties is a serious problem.

At present, even in the case where the scale is increased, the purification of peptide is generally performed by a preparative high performance liquid chromatography method, which requires a large cost. It is desired to provide a method for effectively separating/removing analogue peptide(s) from a mixture of a target peptide and analogue peptide(s) thereof, for replacing or supplementing the preparative high performance liquid chromatography.

PRIOR ART DOCUMENT

Patent Document

Patent Document 1: JP 2018-52933 A
Patent Document 2: JP 2016-190851 A

The disclosures of the prior art documents cited herein are incorporated herein by reference in their entirety.

SUMMARY

Technical Problem

An objective of the present application is to provide a method for purifying a target peptide comprising removing analogue peptide(s) from a mixture comprising the target peptide and the analogue peptide(s), obtained through peptide synthesis. Another objective of the present application is to provide a peptide purification method for replacing or supplementing conventional peptide purification method(s).

Solution to Problem

As a result of studies to solve the above problems, the present inventors have found that when a synthetic peptide product of a target peptide comprising an analogue peptide is mixed with a sulfonic acid compound having a certain structure in the presence of a solvent followed by a solid-liquid separation, the purity (absolute purity, except the sulfonic acid compounds) of the target peptide is improved and a solid product comprising the sulfonate salt of the target peptide having a reduced ratio of the analogue peptide is provided, thereby reaching the present invention.

The invention of the present application is explained in detail below.

[Aspect 1] A method for purifying a target peptide from a peptide product obtained through a peptide synthesis, wherein the target peptide is free at the N-terminus and/or comprises at least one basic amino acid residue, comprising steps:

(1) mixing the peptide product with a solvent in the presence of a sulfonic acid compound to provide a solid;

(2) performing a solid-liquid separation to collect the solid.

[Aspect 1-1] A method for purifying a target peptide from a peptide product obtained through a peptide synthesis, wherein the target peptide is free at the N-terminus and/or comprises at least one basic amino acid residue, comprising steps:

(1) mixing the peptide product with a solvent in the presence of a sulfonic acid compound to provide a solid;

(2) performing a solid-liquid separation one minute or more after the mixing to collect the solid.

[Aspect 1-2] A method for purifying a target peptide from a peptide product obtained through a peptide synthesis, wherein the target peptide is free at the N-terminus and/or comprises at least one basic amino acid residue, comprising steps:

(1) mixing the peptide product with a solvent in the presence of a sulfonic acid compound to provide a solid, wherein the solvent comprises water; an alcohol compound; acetonitrile; an ether compound; a ketone compound; an ester compound; a hydrocarbon compound; DMSO; an amide compound; a halogenated hydrocarbon; or a mixture thereof;

(2) performing a solid-liquid separation to collect the solid.

[Aspect 1-3] A method for purifying a target peptide from a peptide product obtained through a peptide synthesis, wherein the target peptide is free at the N-terminus and/or comprises at least one basic amino acid residue, comprising steps:

(1) mixing the peptide product with a solvent in the presence of a sulfonic acid compound to provide a solid;

(2) performing a solid-liquid separation to collect the solid;

(3) washing the solid.

[Aspect 1-4] A method for purifying a target peptide from a peptide product obtained through a peptide synthesis, wherein the target peptide is free at the N-terminus and/or comprises at least one basic amino acid residue, comprising steps:

(1) mixing the peptide product with a solvent in the presence of a sulfonic acid compound at 0 to 50° C. to provide a solid;

(2) performing a solid-liquid separation at 0 to 50° C. to collect the solid.

[Aspect 1-5] A method for purifying a target peptide from a peptide product obtained through a peptide synthesis, wherein the target peptide is free at the N-terminus and/or comprises at least one basic amino acid residue, comprising steps:

(1) mixing the peptide product with a solvent in the presence of a sulfonic acid compound to provide a solid, wherein the weight ratio of the solvent to the target peptide (the weight of solvent/the weight of target peptide) is 1 to 100000;

(2) performing a solid-liquid separation to collect the solid.

[Aspect 1-6] A method for purifying a target peptide from a peptide product obtained through a peptide synthesis, wherein the target peptide is free at the N-terminus and/or comprises at least one basic amino acid residue, comprising steps:

(1) mixing the peptide product with a solvent in the presence of a sulfonic acid compound to provide a solid, wherein the molar ratio of the sulfonic acid compound to the target peptide is 0.1 to 50;

(2) performing a solid-liquid separation to collect the solid.

[Aspect 1-7] A method for purifying a target peptide from a peptide product obtained through a peptide synthesis, wherein the target peptide is free at the N-terminus and/or comprises at least one basic amino acid residue, comprising steps:

(1) mixing the peptide product with a sulfonic acid compound in the presence of a solvent;

(2) separating the resulting solid from the liquid phase to collect the resulting solid.

[Aspect 2] The method according to any one of Aspects 1, and 1-1 to 1-7, wherein the sulfonic acid compound is represented by formula (I):

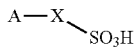

(I)
wherein:
A is $C_{6-14}$aryl (for example, $C_{6-13}$aryl, $C_{6-10}$aryl) which may be substituted, a bicyclic heterocyclic group which may be substituted, $C_{2-3}$alkenyl, or $C_{2-3}$alkynyl;

X is
(i) a single bond,
(ii) $C_{1-6}$alkylene (for example, $C_{1-5}$alkylene, $C_{1-4}$alkylene) which may be substituted,
(iii) —CO—$(CH_2)_n$— wherein the CO binds to the A, or
(iv) $C_{2-4}$ alkenylene; and
n is an integer selected from 1 to 3.

[Aspect 3] The method according to Aspect 2, wherein
A is $C_{6-14}$aryl (for example, $C_{6-13}$aryl, $C_{6-10}$aryl) which may be substituted;
X is
(i) a single bond,
(ii) $C_{1-6}$alkylene (for example, $C_{1-5}$alkylene, $C_{1-3}$alkylene) which may be substituted,
(iii) —CO—$(CH_2)_n$— wherein the CO binds to the A, or
(iv) $C_{2-3}$alkenylene; and
n is an integer selected from 1 to 3.

[Aspect 4] The method according to Aspect 2, wherein
A is a bicyclic heterocyclic group which may be substituted;
X is
(i) a single bond,
(ii) $C_{1-6}$ alkylene (for example, $C_{1-5}$alkylene, $C_{1-4}$alkylene, $C_{1-3}$alkylene),
(iii) —CO—$(CH_2)_n$— wherein the CO binds to the A, or
(iv) $C_{2-3}$alkenylene; and
n is an integer selected from 1 to 3.

[Aspect 5] The method according to Aspect 2, wherein
A is $C_{2-3}$ alkenyl; and
X is $C_{1-4}$alkylene.

[Aspect 6] The method according to Aspect 2, wherein
A is $C_{2-3}$alkynyl; and
X is $C_{1-4}$alkylene.

[Aspect 7] The method according to any one of Aspects 1 to 6 and 1-1 to 1-7 wherein the target peptide has 5 to 31 amino acid residues.

[Aspect 8] The method according to any one of Aspects 1 to 7 and 1-1 to 1-7 wherein the peptide product comprises an analogue peptide.

[Aspect 9] The method according to any one of Aspects 1 to 8 and 1-1 to 1-7 wherein the molar ratio of the analogue peptide to the target peptide is 0.7 or less in the peptide product.

[Aspect 10] The method according to any one of Aspects 1 to 9 and 1-1 to 1-7 wherein the peptide synthesis is a solid phase peptide synthesis.

[Aspect 11] The method according to any one of Aspects 1 to 10 and 1-1 to 1-7 wherein the target peptide comprises at least one basic amino acid residue and may be free at the N-terminus.

[Aspect 12] The method according to any one of Aspects 2, 3, and 7 to 11, wherein
A is $C_{6-14}$aryl (for example, $C_{6-13}$aryl, $C_{6-10}$aryl) which may be substituted with the same or different 1 to 5 substituents selected from the group consisting of $C_{1-4}$alkyl, —CO—$C_{6-10}$aryl, —OH, —O—$C_{1-3}$alkyl, —$NO_2$, —$CO_2H$, —$CO_2$—$C_{1-4}$alkyl, halogen, —$NH_2$, —$CH_2$—$SO_3H$, —$SO_3H$, —CN, —CO—$C_{1-4}$alkyl, —$CF_3$, and $C_{6-10}$aryl.

[Aspect 13] The method according to any one of Aspects 2, 3, and 7 to 12, wherein
A is $C_{6-13}$aryl selected from phenyl, naphthyl, fluorenyl, and indanyl wherein the $C_{6-13}$aryl may be substituted with the same or different 1 to 5 substituents selected from the group consisting of $C_{1-4}$alkyl, —CO—$C_{6-10}$aryl, —OH, —O—$C_{1-3}$alkyl, —$NO_2$, —$CO_2H$, —$CO_2$—$C_{1-4}$alkyl, halogen, —$NH_2$, —$CH_2$—$SO_3H$, —$SO_3H$, —CN, —CO—$C_{1-4}$alkyl, —$CF_3$, and $C_{6-10}$aryl.

[Aspect 13-1] The method according to any one of Aspects 2, 3, and 7 to 12, wherein
A is $C_{6-10}$aryl selected from phenyl, naphthyl, and indanyl wherein the $C_{6-10}$aryl may be substituted with the same or different 1 to 5 substituents selected from the group consisting of $C_{1-4}$alkyl, —CO—$C_{6-10}$aryl, —OH, —O—$C_{1-3}$alkyl, —$NO_2$, —$CO_2H$, —$CO_2$—$C_{1-4}$alkyl, halogen, —$NH_2$, —$CH_2$—$SO_3H$, —$SO_3H$, —CN, —CO—$C_{1-4}$alkyl, —$CF_3$, and $C_{6-10}$aryl.

[Aspect 14] The method according to any one of Aspects 2, 4, and 7 to 11, wherein
A is a bicyclic heterocyclic group selected from the group consisting of 2,3,4,5-tetrahydro-1H-1-benzazepinyl, benzoxanyl, indolinyl, isoindolinyl, phthalazinyl, chromanyl, benzofuranyl, benzothiophenyl, pyrimidinyl, benzothiazolyl, quinolyl, isochromanyl, and benzotriazolyl wherein the bicyclic heterocyclic group may be substituted.

[Aspect 15] The method according to any one of Aspects 2, 4, 7 to 11, and 14, wherein A is a bicyclic heterocyclic group which may be substituted with the same or different 1 to 5 substituents selected from the group consisting of $C_{6-10}$aryl, $C_{1-4}$alkyl, —CO—$C_{6-10}$aryl, —OH, —O—$C_{1-3}$alkyl, —NO$_2$, —CO$_2$H, CO$_2$—$C_{1-4}$alkyl, halogen, —NH$_2$, —CH$_2$—SO$_3$H, —SO$_3$H, —CN, —CO—$C_{1-4}$alkyl, —CF$_3$, and oxo.

[Aspect 16] The method according to any one of Aspects 2, 4, 7 to 11, 14 and 15, wherein A is a bicyclic heterocyclic group selected from

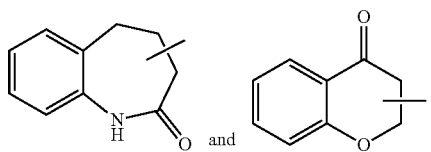

wherein the bicyclic heterocyclic group may be substituted with one phenyl group.

[Aspect 17] The method according to any one of Aspects 2 to 4, 7 to 16 and 13-1, wherein X is (i) a single bond, (ii) $C_{1-4}$alkylene (for example, $C_{1-3}$alkylene) which may be substituted with the same or different 1 to 3 substituents selected from the group consisting of methyl, benzyl, cyano, and phenyl, or (iii) —CO—CH$_2$— wherein the CO binds to the A.

[Aspect 17-1] The method according to any one of Aspects 2 to 4, and 7 to 16 and 13-1, wherein X is (i) a single bond, (ii) $C_{1-4}$alkylene (for example, $C_{1-3}$alkylene) which may be substituted with one methyl group, one benzyl group, one cyano group, and/or one or two phenyl groups, or (iii) —CO—CH$_2$— wherein the CO binds to the A.

[Aspect 18] The method according to Aspect 12, wherein X is (i) a single bond, (ii) $C_{1-4}$alkylene (for example, $C_{1-3}$alkylene) which may be substituted with the same or different 1 to 3 substituents selected from the group consisting of methyl, benzyl, cyano, and phenyl, or (iii) —CO—(CH$_2$)— wherein the CO binds to the A.

[Aspect 18-1] The method according to Aspect 12, wherein X is (i) a single bond, (ii) $C_{1-4}$alkylene (for example, $C_{1-3}$alkylene) which may be substituted with one methyl group, one benzyl group, one cyano group, and/or one or two phenyl groups, or (iii) —CO—(CH$_2$)— wherein the CO binds to the A.

[Aspect 19] The method according to any one of Aspects 2 to 4, 7 to 18, 13-1, 17-1, and 18-1, wherein X is a single bond.

[Aspect 20] The method according to Aspect 16, wherein X is a single bond.

[Aspect 21] The method according to any one of Aspects 1 to 20, 1-1 to 1-7, 13-1, 17-1, and 18-1, wherein the sulfonic acid compound is selected from:

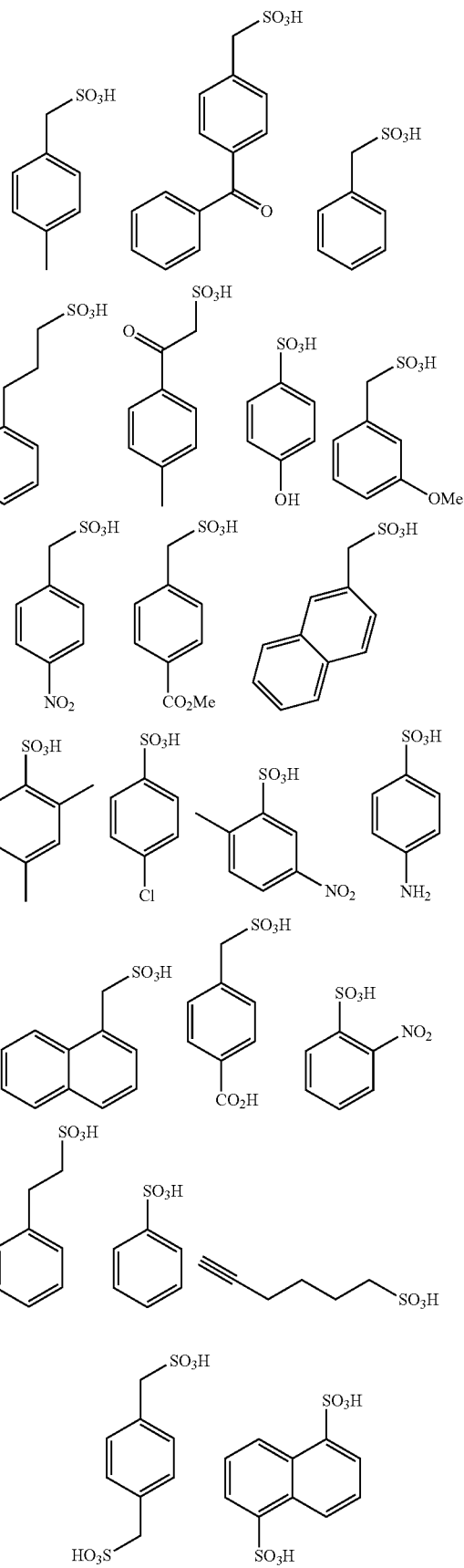

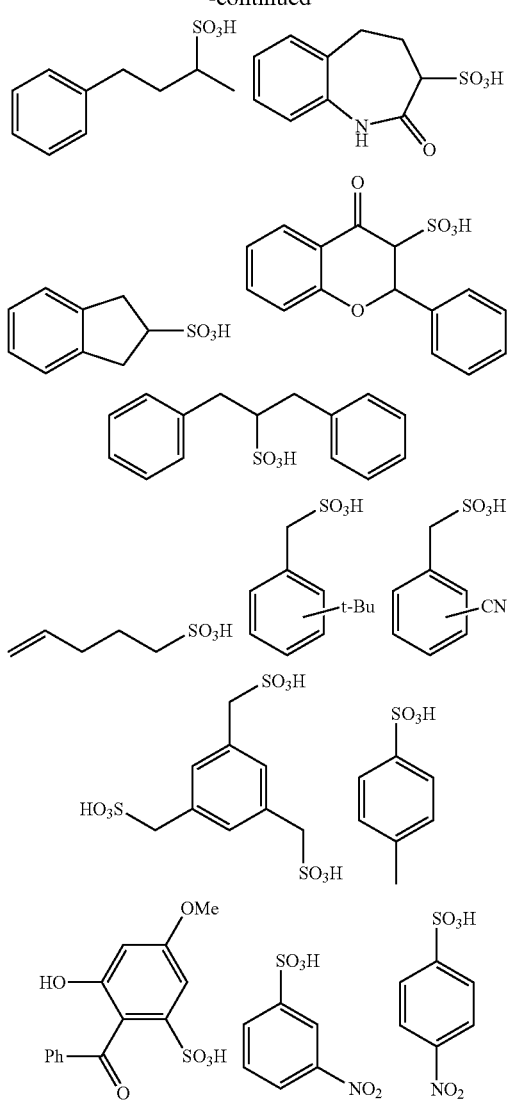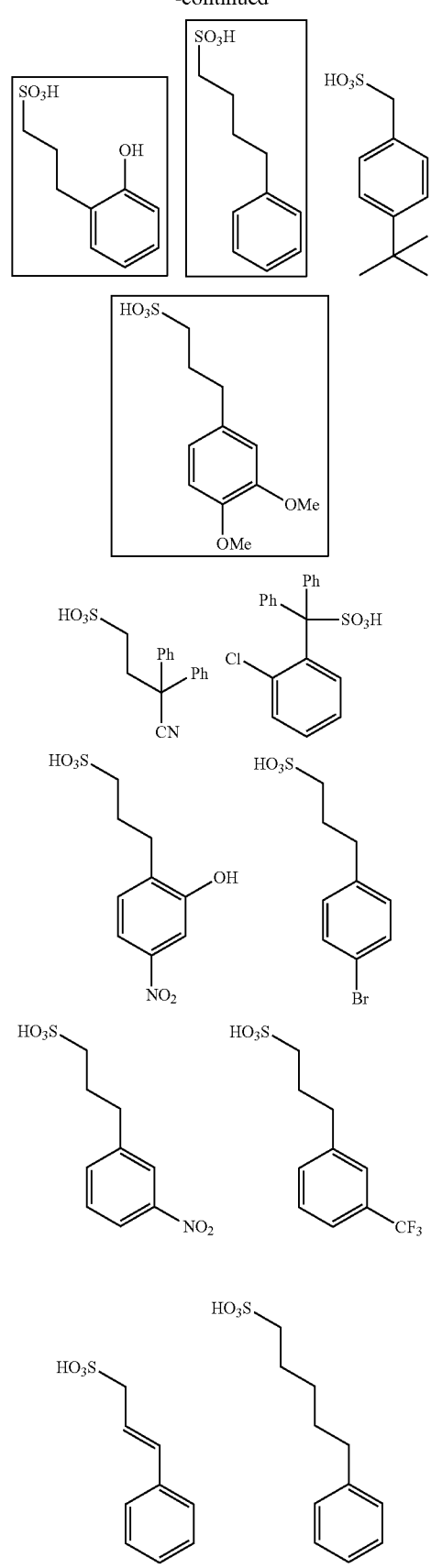

-continued

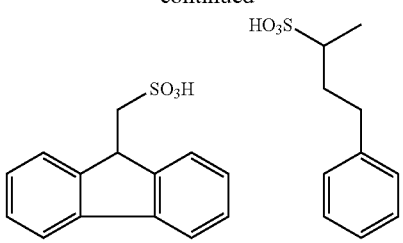

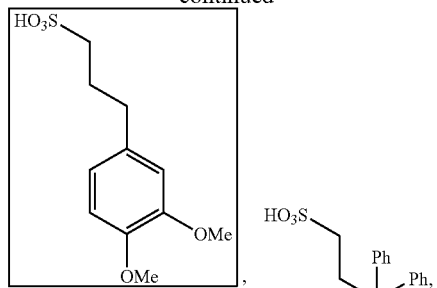

[Aspect 22] The method according to any one of Aspects 1 to 21, and 1-1 to 1-7, 13-1, 17-1, and 18-1, further comprising a step of removing the sulfonic acid compound.

[Aspect 23] The method according to any one of Aspects 1 to 22, 1-1 to 1-7, 13-1, 17-1, and 18-1, wherein the method is for increasing the molar ratio of the target peptide to an analogue peptide.

[Aspect 24] A method for producing a target peptide, comprising the method according to any one of Aspects 1 to 23, 1-1 to 1-7, 13-1, 17-1, and 18-1.

[Aspect 25] An agent comprising a target peptide purified by a method comprising the method according to any one of Aspects 1 to 23, 1-1 to 1-7, 13-1, 17-1, and 18-1.

[Aspect 26] An agent comprising a sulfonic acid compound for use in the method according to any one of Aspects 1 to 23, 1-1 to 1-7, 13-1, 17-1, and 18-1.

[Aspect 27] A compound selected from:

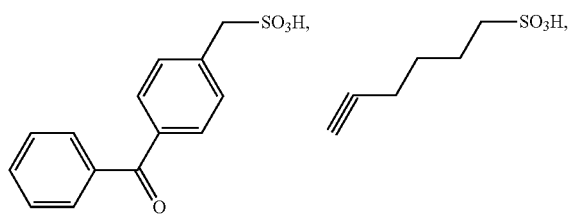

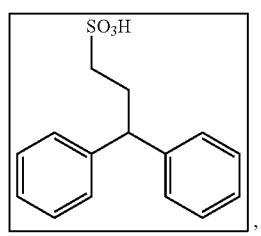

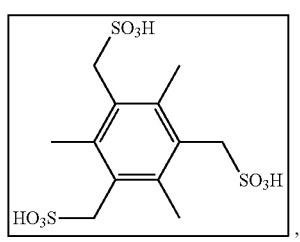

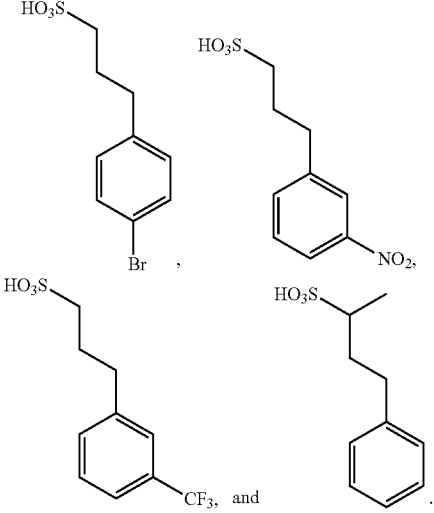

[Aspect 28] An agent comprising a target peptide obtained through purification from a peptide product obtained through a peptide synthesis, wherein the target peptide is free at the N-terminus and/or comprises at least one basic amino acid residue, and the purification comprises steps:
(1) mixing the peptide product with a solvent in the presence of a sulfonic acid compound to provide a solid;
(2) performing a solid-liquid separation to collect the solid.

[Aspect 28-1] An agent comprising a target peptide obtained through purification from a peptide product obtained through a peptide synthesis, wherein the target peptide is free at the N-terminus and/or comprises at least one basic amino acid residue, and the purification comprises steps:
(1) mixing the peptide product with a sulfonic acid compound in the presence of a solvent;
(2) separating the resulting solid from the liquid phase to collect the resulting solid.

[Aspect 29] An agent comprising a sulfonic acid compound, for use in purification of a target peptide from a peptide product obtained through a peptide synthesis, wherein the target peptide is free at the N-terminus and/or comprises at least one basic amino acid residue, and the purification comprises steps:

(1) mixing the peptide product with a solvent in the presence of the sulfonic acid compound to provide a solid;

(2) performing a solid-liquid separation to collect the solid.

[Aspect 29-1] An agent comprising a sulfonic acid compound, for use in purification of a target peptide from a peptide product obtained through a peptide synthesis, wherein the target peptide is free at the N-terminus and/or comprises at least one basic amino acid residue, and the purification comprises steps:

(1) mixing the peptide product with the agent comprising the sulfonic acid compound in the presence of a solvent;

(2) separating the resulting solid from the liquid phase to collect the resulting solid.

Effect of the Invention

By the invention of the application, an increased purity of a target peptide is provided from a peptide product obtained through a peptide synthesis, which may comprise an analogue peptide.

DESCRIPTION OF EMBODIMENTS

In one aspect, the present application provides a method for purifying a target peptide from a peptide product obtained through a peptide synthesis, wherein the target peptide is free at the N-terminus and/or comprises at least one basic amino acid residue, comprising steps:

(1) mixing the peptide product with a solvent in the presence of a sulfonic acid compound to provide a solid;

(2) performing a solid-liquid separation to collect the solid.

In one aspect, the present application provides a method for purifying a target peptide from a peptide product obtained through a peptide synthesis, wherein the target peptide is free at the N-terminus and/or comprises at least one basic amino acid residue, comprising steps:

(1) mixing the peptide product with a sulfonic acid compound in the presence of a solvent;

(2) separating the resulting solid from the liquid phase to collect the resulting solid.

The term "purify/purification" as used herein means that the purity of a substance is increased. The purity may mean both an absolute purity (the amount of a substance of interest relative to the total amount of the mixture comprising the substance of interest) and a relative purity (the amount of a substance of interest relative to the amount of another substance (for example, impurity), in a mixture).

For example, in the present invention, the term "purifying a target peptide" includes a case where the amount of the target peptide in the solid obtained after mixing with the sulfonic acid compound relative to the weight obtained by subtracting the portion corresponding to the sulfonic acid compound from the solid obtained after mixing with the sulfonic acid compound is increased as compared to the amount of the target peptide relative to the total amount of the peptide product before mixing with the sulfonic acid compound (for example, increase in % by weight). In the present invention, the term "purifying a target peptide" includes, for example, a case where the molar ratio of the target peptide to the analogue peptide in the resulting solid after the mixing with sulfonic acid compound is increased as compared with before the mixing.

In the present application, the method for determining the purity of the target peptide is not particularly limited, and the purity may be determined by a commonly used method (for example, HPLC method).

In the present application, the term "peptide synthesis" is not particularly limited as long as it is a method for synthesizing a peptide, and examples thereof include an organic chemical synthesis method (for example, solid phase and liquid phase methods) and fermentation methods, which may be performed by a commonly used method. In peptide synthesis, the synthesis conditions (for example, resin, protecting group, reaction temperature, reaction time, and solvent in the organic chemical synthesis methods; culture conditions, host, vector, nucleic acid sequence in the fermentation methods) are usually set so as to suppress the generation of impurities (for example, analogue peptide(s)). Also in the present application, the peptide synthesis is preferably conducted under synthesis conditions in which generation of analogue peptide(s) is suppressed, on the basis of the knowledge generally known to a person skilled in the art, and the amount of substance of the target peptide is preferably larger than that of the analogue peptide, in the peptide product obtained through the peptide synthesis.

For example, in the peptide product obtained through peptide synthesis, the molar ratio of the analogue peptide to the target peptide (analogue peptide/target peptide) is 0.7 or less (preferably 0.6 or less, more preferably 0.5 or less, still more preferably 0.45 or less, still more preferably 0.4 or less, and more preferably 0.2 or less). A lower molar ratio of the analogue peptide to the target peptide is preferable. Thus the lower limit of the range of the molar ratio is not particularly limited, but examples of the range of the molar ratio include 0.0001 to 0.7, 0.001 to 0.6, and 0.01 to 0.5. For example, an approximate value of the molar ratio (for example, area ratio) calculated based on a value obtained by HPLC may be used as the molar ratio.

In a peptide product obtained through a peptide synthesis, "the amount of substance of the target peptide is larger than that of the analogue peptide" means that the amount of substance of the target peptide is larger than the amount of substance of one kind of analogue peptide, and when a multiple kinds of analogue peptides are comprised, it means that the amount of substance of the target peptide is larger than that of each analogue peptide. In a peptide product obtained through a peptide synthesis, "the amount of substance of the target peptide is larger than that of the analogue peptide" may be indicated by the extremely high probability that in the peptide product the amount of substance of the analogue peptide is lower than that of the target peptide due to the fact that the amount of the target peptide relative to the total amount of the peptide product obtained through a peptide synthesis, the absolute purity, is large (for example, the concentration of the target peptide in the peptide product is 40 wt. % or more, 50 wt. % or more, 60 wt. % or more, 70 wt. % or more, 80 wt. % or more, or 90 wt. % or more).

In the present application, "target peptide" means a peptide which is produced by a peptide synthesis carried out for the purpose of producing the peptide. The structure of the target peptide is not particularly limited so long as: is free at the N-terminus; has at least 1 (for example, 1 to 5, 1 to 4, 1 to 3, 1 to 2, and 1) basic amino acid residue; or the N-terminus is free and has at least 1 (for example, 1 to 5, 1 to 4, 1 to 3, 1 to 2, and 1) basic amino acid residue. The target peptide preferably has 5 to 31 amino acid residues, more preferably 5 to 25, still more preferably 5 to 20, and even more preferably 5 to 15 amino acid residues. The range of the number of amino acid residues of the target peptide may also be indicated by a combination of a lower limit selected from 5, 6, 7, and 8 and an upper limit selected from 31, 25, 20, 15, and 10.

The amino acid residues which may be comprised in the target peptide may be those derived from naturally occurring amino acids such as L-selenocysteine, 2-aminoisobutyric acid, D-isovaline, L-isovaline, L-norleucine, and L-ornithine in addition to the 20 amino acids listed in the table below (L-form except glycine, which does not have an asymmetric carbon) which usually constitute a protein; and those derived from unnatural amino acids which do not exist in nature or exist in small amounts, if any (therefore, it is usually produced by chemical synthesis, etc.).

Examples of unnatural amino acids include:
D forms of the 19 amino acids, excluding glycine, shown in the table below;
N-methylated forms of the 20 amino acids shown in the table below (for example, N-methylglycine, L-N-methylphenylalanine) and enantiomers of L-N-methylated forms of the 19 amino acids, excluding N-methylglycine, shown in the table below;
both enantiomers of α-methylated forms of the 18 amino acids, excluding glycine and alanine, shown in the table below (for example, α-methyllysine);
both enantiomers of α-ethylated forms of the 19 amino acids, excluding alanine, shown in the table below;
D-selenocysteine;
D-norleucine;
D-ornithine;
(S)- or (R)-2,3-diaminopropionic acid;
(S)- or (R)-2,4-diaminobutyric acid;
(S)- or (R)-pyroglutamic acid;
(S)- or (R)-α-methyl-orthofluorophenylalanine;
(S)- or (R)-α-(4-pentenyl)alanine;
(S)- or (R)-α-(7-octenyl)alanine;
(S)- or (R)-α-propargylalanine;
(S)- or (R)-α-allylalanine;
(S)- or (R)-indan-2-ylglycine;
(S)- or (R)-pyridin-3-ylmethylglycine, and derivatives thereof in which the pyridine ring may be substituted with phenyl group(s) which may be substituted with alkyl group(s);
(S)- or (R)-pyridin-2-ylmethylglycine;
(S)- or (R)-pipecolic acid; and
(S)- or (R)- and trans- or cis-4-hydroxyproline;
RC8((R)-α-(7-octenyl)alanine);
SC5((S)-α-(4-pentenyl)alanine).

| alanine | A |
| leucine | L |
| arginine | R |
| lysine | K |
| asparagine | N |
| methionine | M |
| aspartic acid | D |
| phenylalanine | F |
| cysteine | C |
| proline | P |
| glutamine | Q |
| serine | S |
| glutamic acid | E |
| threonine | T |
| glycine | G |
| tryptophan | W |
| histidine | H |
| tyrosine | Y |
| isoleucine | I |
| valine | V |

In the present application, the term "basic amino acid residue" means an amino acid residue derived from an amino acid having basic moiety(moieties) other than the amino group (for example, D- or L-lysine, D- or L-arginine, D- or L-histidine, D- or L-ornithine, (S)- or (R)-2,3-diaminopropionic acid, and (S)- or (R)-2,4-diaminobutyric acid).

In the present application, the target peptide may be modified at the terminus (termini) with a protecting group and the like commonly used in peptide synthesis. For example, the N-terminus may be modified with Ac group (acetyl group), Fmoc group (9-fluorenylmethyloxycarbonyl group), or Boc group (tert-butoxycarbonyl group). For example, the C-terminus may be modified with an amide group or an ester group.

In the present application, the term "analogue peptide" refers to a peptide that may be produced by peptide synthesis for producing a target peptide and that is not the target peptide. Examples of the analogue peptide include peptide(s) in which:
(1) some of the amino acid residues (for example, continuous or discontinuous 1 to 3 amino acid residues, continuous or discontinuous 1 to 2 amino acid residues, or amino acid residue) in the target peptide are/is duplicated;
(2) some of the amino acid residues (for example, continuous or discontinuous 1 to 3 amino acid residues, continuous or discontinuous 1 to 2 amino acid residues, or 1 amino acid residue) in the target peptide are/is deleted.
(3) some of the amino acid residues (for example, continuous or discontinuous 1 to 3 amino acid residues, continuous or discontinuous 1 to 2 amino acid residues, or amino acid residue) in the target peptide are/is epimerized (for example, epimerization by isomerization at α-position of N-protected amino acid); and/or
(4) some of the amino acid residues (for example, continuous or discontinuous 1 to 3 amino acid residues, continuous or discontinuous 1 to 2 amino acid residues, and 1 amino acid residue) in the target peptide are/is replaced by the same number of amino acid residue(s).

The number of amino acid residues of the analogue peptide is, for example, the same as, 1 to 3 (preferably 1 to 2, more preferably 1) more than, or 1 to 3 (preferably 1 to 2, more preferably 1) less than the number of amino acid residues of the target peptide.

The "analogue peptide" may have basic moiety/moieties (for example, is free at the N-terminus/has at least 1 (for example, 1 to 5, 1 to 4, 1 to 3, 1 to 2, or 1) basic amino acid residue), or may not have such a basic moiety. As described above, in a peptide product obtained through a peptide synthesis, the amount (amount of substance) of a target peptide is usually larger than that of analogue peptide, and when the structures of the target peptide and the analogue peptide are similar, the solubility properties of the target peptide and the analogue peptide in a solvent may usually be similar. Therefore, in the solid obtained after mixing with the sulphonic acid compound, the ratio of the target peptide, which was originally contained more than the analogue peptide, may be increased although when the "analogue peptide" has a basic moiety, a solid may be formed by forming a salt with the sulphonic acid compound. However, the effect of the present invention is not limited to any specific mechanism.

In the present application, a solvent used in mixing with a sulfonic acid compound is not particularly limited, and may be appropriately selected in consideration of the purification efficiency of the target peptide. Examples of the solvent include:

water;

alcohol compounds (for example, $C_{1-4}$ alcohol (for example, isopropyl alcohol, methanol, ethanol));

acetonitrile;

ether compounds (for example, $C_{2-6}$ ether (for example, diethyl ether, MTBE, tetrahydrofuran, 1,4-dioxane, 1,2-dimethoxyethane, and CPME (cyclopentyl methyl ether)));

ketone compounds (for example, $C_{3-6}$ ketone (for example, acetone), MEK (methyl ethyl ketone), methyl isopropyl ketone, MIBK (methyl isobutyl ketone));

ester compounds (for example, $C_{3-6}$ ester (for example ethyl acetate, isopropyl acetate, t-butyl acetate));

hydrocarbon compounds (for example, 06-9 hydrocarbon (for example, toluene));

DMSO;

amide compounds (for example, DMF (N,N-dimethylformamide), DMA (N,N-dimethylacetamide), NMP (N-methylpyrrolidone));

halogenated hydrocarbons (for example, chloroform, dichloromethane, 1,2-dichloroethane); and mixture thereof (wherein the mixture means any combination thereof). The solvent may further contain other substance(s).

Further examples of the solvent include water, isopropyl alcohol (IPA), methanol (MeOH), 1,4-dioxane, 1,2-dimethoxyethane (DME), tetrahydrofuran (THF), acetone, acetonitrile, ethanol, ethyl acetate, toluene, MTBE, DMSO, diethyl ether, and a mixture thereof (where the mixture means any combination thereof). The solvent may further contain other substance(s).

When a peptide product obtained through a peptide synthesis is mixed with a sulfonic acid compound in the presence of a solvent, the amounts of the solvent and the sulfonic acid compound(s) relative to the peptide product are not particularly limited and may be appropriately selected in consideration of the purification efficiency of the target peptide. The solvent may be used at the weight-by-weight ratio to the target peptide obtained by peptide synthesis in the range of 1 to 100000, preferably 1 to 10000, preferably 1 to 2000, and more preferably 10 to 1000, which may be based on the theoretical value of the weight of the target peptide.

For example, the molar ratio of the sulfonic acid compound to the target peptide may be in the range 0.1 to 50, preferably 0.2 to 40, more preferably 0.3 to 30, and even more preferably 0.5 to 20, which may be based on the theoretical value of the amount of substance of the target peptide.

Further, the sulphonic acid compound may be used at the molar ratio to the target peptide, which may be based on the theoretical value of the amount of substance of the target peptide, in the ranges:

when the sulfonic acid compound has one sulfo group, for example, in the range 0.5 to 20, preferably 0.8 to 10, more preferably 1 to 8, even more preferably 1.5 to 7;

when the sulfonic acid compound has 2 sulfo groups, for example, in the range 0.2 to 10, preferably 0.4 to 5, more preferably 0.5 to 4, even more preferably 0.75 to 3.5;

when the sulfonic acid compound has 3 sulfo groups, for example, in the range 0.15 to 6, preferably 0.3 to 3.3, more preferably 0.4 to 2.6, and even more preferably 0.5 to 2.3.

The theoretical value may mean a value calculated by assuming that the purity of the target peptide in the peptide synthesis product is 100%.

The method for separating the resulting solid from the liquid phase to collect the resulting solid (solid-liquid separation) after mixing with the sulfonic acid compound is not particularly limited, and may be appropriately selected depending on the production scale, etc., and for example, includes filtration, centrifugation, decant, etc.

Since the purity of the target peptide in the solid may be increased through solid-liquid equilibrium, the solid-liquid separation is preferably performed after a predetermined time (for example, 1 minute or more, 2 minutes or more, 3 minutes or more, 4 minutes or more, 5 minutes or more, 10 minutes or more, 30 minutes or more, 1 hour or more, 2 hours or more, 3 hours or more) has elapsed after the mixing the peptide product with the sulfonic acid compound and the solvent.

In consideration of operation efficiency, it is preferable that the solid-liquid separation is performed, for example, within one day, within two days, within one week, or within two weeks, but the mixture may be stored without the solid-liquid separation, and then the solid-liquid separation may be performed accordingly.

The temperature at the time of mixing with the sulfonic acid compound and/or the solvent and at the time of separating the resulting solid from the liquid phase to collect the resulting solid (solid-liquid separation) is not particularly limited, and may be appropriately selected in consideration of the purification efficiency of the target peptide, for example. The examples include 0 to 50° C., 0 to 40° C., 0 to 30° C., and 10 to 25° C.

The solid obtained by the solid-liquid separation may be optionally washed. The liquid used for washing (the liquid for washing) is not particularly limited, and may be appropriately selected in consideration of the purification efficiency of the target peptide. Examples of the liquid for washing include:

water;

alcohol compounds (for example, $C_{1-4}$alcohol (for example, isopropyl alcohol, methanol, ethanol));

acetonitrile;

ether compounds (for example, $C_{2-6}$ ether (for example, diethyl ether, MTBE, tetrahydrofuran, 1,4-dioxane, 1,2-dimethoxyethane, CPME (cyclopentyl methyl ether)));

ketone compounds (for example, $C_{3-6}$ ketone (for example, acetone), MEK (methyl ethyl ketone), methyl isopropyl ketone, MIBK (methyl isobutyl ketone));

ester compounds (for example, $C_{3-6}$ester (for example, ethyl acetate, isopropyl acetate, t-butyl acetate));

hydrocarbon compounds (for example, 06-9hydrocarbon (for example, toluene));

DMSO;

amide compounds (for example, DMF (N,N-dimethylformamide), DMA (N,N-dimethylacetamide), NMP (N-methylpyrrolidone));

halogenated hydrocarbons (for example, chloroform, dichloromethane, 1,2-dichloroethane); and mixture thereof (wherein the mixture means any combination thereof). The liquid for washing may further contain other substance(s).

Repeating the purification method of the present application on the solid obtained by the purification method of the present application is one embodiment of the purification method of the present application. The purity of the target peptide may be increased by repeating the purification method of the present application.

The purification method of the present application may be performed in combination with other purification method(s) (for example, preparative HPLC, recrystallization, dispersion and wash). For example, the solid obtained by the method of the present application may be subjected to another purification method, or a peptide product previously purified by another purification method may be subjected to the purification method of the present invention.

It is preferable that the sulfonic acid compound is removed from the solid obtained by the purification method of the present application in a further purification step. The method for removing the sulfonic acid compound is not particularly limited, and may be carried out by a usual method for removing the sulfonic acid compound (for example, an acid or alkali treatment, and a removal method using an ion exchange resin).

In the present application, the term "sulfonic acid compound" means an organic compound having sulfo group(s) (—$SO_3H$). In the present application, the sulfonic acid compound is preferably those where a sulfo group is attached to a moiety having one or more unsaturated bonds through a single bond or a short linker (for example, $C_{1-12}$, $C_{1-6}$, $C_{1-4}$, etc.).

Preferred examples of the sulfonic acid compound include a sulfonic acid compound of formula (I):

(I)

wherein:

A is $C_{6-14}$aryl (for example, $C_{6-13}$aryl, $C_{6-10}$aryl) which may be substituted, a bicyclic heterocyclic group which may be substituted, $C_{2-3}$alkenyl, or $C_{2-3}$alkynyl;

X is (i) a single bond, (ii) $C_{1-6}$alkylene (for example, $C_{1-5}$ alkylene, $C_{1-4}$alkylene) which may be substituted, (iii) —CO—$(CH_2)_n$— wherein the CO binds to the A, or (iv) $C_{2-4}$alkenylene; and n is an integer selected from 1 to 3.

The term "$C_{6-14}$aryl" as used herein alone or as part of another group refers to a 6 to 14 membered monocyclic, bicyclic or tricyclic aromatic hydrocarbon ring group and a ring group wherein one cycloalkane is fused to said aromatic hydrocarbon ring. Examples of $C_{6-14}$aryl include phenyl, naphthyl, indanyl, tetrahydronaphthyl, and fluorenyl.

The term "$C_{6-10}$ aryl" as used herein alone or as part of another group refers to a 6 to 10 membered monocyclic or bicyclic aromatic hydrocarbon ring group, and a ring group wherein one cycloalkane is fused to said aromatic hydrocarbon ring group. Examples of $C_{6-10}$ aryl include phenyl, naphthyl, indanyl, and tetrahydronaphthyl.

Examples of "$C_{6-14}$aryl (or $C_{6-13}$aryl, $C_{6-10}$aryl) which may be substituted" include $C_{6-14}$ aryl (or $C_{6-13}$ aryl, $C_{6-10}$ aryl) which may be substituted with the same or different 1 to 5 (for example, 1 to 3, 1 to 2, and 1) substituents selected from the group consisting of $C_{1-4}$alkyl, —CO—$C_{6-10}$aryl, —OH, —O—$C_{1-3}$alkyl, —$NO_2$, —$CO_2H$, —$CO_2$—$C_{1-4}$alkyl, halogen, —$NH_2$, —$CH_2$—$SO_3H$, —$SO_3H$, —CN, —CO—$C_{1-4}$alkyl, —$CF_3$, and $C_{6-10}$aryl.

The term "a bicyclic heterocyclic group" as used herein means a 8 to 11 membered bicyclic group wherein a monocyclic aromatic ring having 1 to 4 heteroatoms selected from a nitrogen atom, an oxygen atom and a sulfur atom (for example, pyridine, furan, thiophene, imidazole, pyrimidine, oxazole, thiazole, thiazine, triazole) or a monocyclic non-aromatic ring (tetrahydropyran, azepane, piperidine, etc.) is fused to a monocyclic aromatic ring (benzene, pyridine, etc.). The bicyclic heterocyclic group may be attached to another moiety at any heteroatom or carbon atom which results in a stable structure. The bicyclic heterocyclic group may comprise one or more (for example, 1 or 2) oxo groups. Examples of the bicyclic heterocyclic group include:

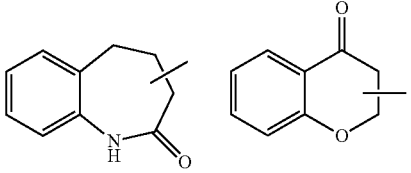

2,3,4,5-tetrahydro-1H-1-benzazepinyl, benzoxanyl, indolinyl, isoindolinyl, phthalazinyl, chromanyl, benzofuranyl, benzothiophenyl, pyrimidinyl, benzothiazolyl, quinolyl, isochromanyl, and benzotriazolyl.

Examples of "a bicyclic heterocyclic group which may be substituted" as used herein include a bicyclic heterocyclic group which may be substituted with the same or different 1 to 5 (for example, 1 to 3, 1 to 2, and 1) substituents selected from the group consisting of $C_{6-10}$aryl, $C_{1-4}$alkyl, —CO—$O_{6-10}$aryl, —OH, —O—$C_{1-3}$alkyl, —$NO_2$, —$CO_2H$, —$CO_2$—$C_{1-4}$alkyl, halogen, —$NH_2$, —$CH_2$—$SO_3H$, —$SO_3H$, —CN, —CO—$C_{1-4}$alkyl, —$CF_3$, and oxo.

As used herein, "$C_{2-3}$alkenyl" means a straight or branched unsaturated hydrocarbon group having 2 to 3 carbon atoms and comprising 1 or 2 double bonds, examples of which include vinyl, allyl, 1-propenyl, isopropenyl, allenyl.

As used herein, "$C_{2-3}$alkynyl" means a straight or branched unsaturated hydrocarbon group having 2 to 3 carbon atoms and comprising one triple bond, examples of which include ethynyl, propynyl (1-propynyl, 2-propynyl).

As used herein, "$C_{1-4}$alkylene" means a divalent group derived from a straight chain $C_{1-4}$alkyl. Examples of $C_{1-4}$alkylene include methylene, ethylene, trimethylene, and tetramethylene.

As used herein, "$C_{1-6}$alkylene" means a divalent group derived from a straight chain $C_{1-6}$alkyl. Examples of $C_{1-6}$alkylene include methylene, ethylene, trimethylene, tetramethylene, and pentamethylene.

As used herein, "$C_{1-3}$alkylene" means a divalent group derived from a straight chain $C_{1-3}$alkyl. Examples of $C_{1-3}$alkylene include methylene, ethylene, and trimethylene.

As used herein, examples of "$C_{1-6}$alkylene (or $C_{1-5}$alkylene, $C_{1-4}$alkylene, $C_{1-3}$ alkylene) which may be substituted" include $C_{1-6}$alkylene (or $C_{1-5}$alkylene, $C_{1-4}$alkylene, $C_{1-3}$alkylene) which may be substituted with the same or different 1 to 3 substituents selected from the group consisting of methyl, benzyl, cyano, and phenyl (for example, $C_{1-6}$alkylene (or $C_{1-5}$alkylene, $C_{1-4}$alkylene, $C_{1-3}$alkylene) which may be substituted with one methyl group, one benzyl group, or one phenyl group)).

In the "—CO—$(CH_2)_n$—" as used herein, n is an integer of 1 to 3 (preferably 1 to 2), and preferred examples of —CO—$(CH_2)_n$— include —CO—$CH_2$—.

As used herein, "$C_{2-4}$alkenylene" means a divalent group derived from a straight chain $C_{2-4}$alkenyl. As used herein, "$C_{2-3}$alkenylene" means a divalent group derived from a straight chain $C_{2-3}$alkenyl. Examples of $C_{2-4}$alkenylene and $C_{2-3}$alkenylene include vinylene(-CH=CH—), and propenylene(-$CH_2$CH=CH—).

The term "$C_{1-4}$alkyl" as used herein alone or as part of another group means a straight or branched saturated hydrocarbon group having 1 to 4 carbon atoms. Examples of $C_{1-4}$alkyl include methyl, ethyl, propyl, isopropyl, butyl, isobutyl, sec-butyl, and tert-butyl.

The term "$C_{1-3}$alkyl" as used herein alone or as part of another group means a straight or branched saturated hydrocarbon group having 1 to 3 carbon atoms. Examples of $C_{1-3}$alkyl include methyl, ethyl, propyl, and isopropyl.

As used herein, examples of a "—CO—$C_{6-10}$aryl" include —CO-phenyl.

As used herein, examples of the halogen include fluorine (F), chlorine (Cl), bromine (Br) and iodine (I).

More preferred examples of the sulfonic acid compound include those listed in [Aspect 21] above.

One aspect of the present invention provides a method for producing a target peptide comprising the purification method of the present application.

One aspect of the present invention provides an agent comprising a target peptide purified by a method comprising the purification method of the present application. The agent may be prepared by a usual method.

One aspect of the present invention provides an agent comprising a sulfonic acid compound for use in the purification method of the present application. The agent may be prepared by a usual method.

Example

The present invention is explained in further detail with reference to Test examples. However, the scope of the invention is not limited to these Examples.

Purification of Target Peptide
Outline of Examinations:

When a target peptide is synthesized by solid phase method, it is expected that analogue peptides are contained in the resulting crude peptide as impurities, but it is difficult to identify what kind of analogue peptides are actually contained. Therefore, the target peptide and the pseudo-analogue peptide having a known sequence as the analogue peptide are synthesized by solid phase method, and the resulting crude target peptide, the resulting crude pseudo-analogue peptide, and each acid compound are dissolved in a solvent, which provides a uniform sample to obtain a value before the treatment by HPLC, followed by lyophilization to remove the solvent. A solvent is added to the residue to provide a solid-liquid mixture, and then the supernatant is removed. The ratio of the amount of substance (mol) of the target peptide in the solid to the sum of the amount of substance (mol) of the target peptide and the amount of substance (mol) of the pseudo-analogue peptide in the solid is determined. Whether the target peptide is purified in the solid is evaluated by the change of the ratios.

1-1: Synthesis of Peptide

The target peptides and the analogue peptides (pseudo) shown in the tables below were respectively synthesized by the solid phase method described below.

TABLE 1-1

| Target peptide | Analogue peptide |
|---|---|
| (1)Ac-YFYPEL-NH$_2$(SEQ ID NO: 1) | (1)Ac-YYPEL-NH$_2$(SEQ ID NO: 16) |
| (27)Ac-YHYPEL-NH$_2$(SEQ ID NO: 62) | |
| (28)Ac-Y(MeK)YPEL-NH$_2$(SEQ ID NO: 63) | |
| (2)H-YFYPEL-NH$_2$(SEQ ID NO: 2) | (2)H-YYPEL-NH$_2$(SEQ ID NO: 17) |
| (3)H-VIRALRRALVALRALR-OH(SEQ ID NO: 3) | (3)H-VIRALRALVALRALR-OH(SEQ ID NO: 18) |
| (4)H-ARLDVASEFRKKWNKALSR-NH$_2$ (SEQ ID NO:4) | (4)H-ARLDVASEFRKKNKALSR-NH$_2$(SEQ ID NO: 19) |
| (5)H-HAEGTFTSDVSSYLEGQAAKEFIAWLVKGRG-OH(SEQ ID NO: 5) | (5)H-HAEGTFTSDVSSYLEGQAAKEFAWLVKGRG-OH(SEQ ID NO: 20) |
| (6)H-AGCKNFFWKTFTSC-OH(SEQ ID NO: 6) | (6)H-AGCKNFFWKTFTS-OH(SEQ ID NO: 21) |
| | (35)H-AGcKNFFWKTFTSC-OH |
| (7)H-AQKLRASD-OH(SEQ ID NO: 7) | (7)H-AQKLRAD-OH(SEQ ID NO: 22) |
| | (8)H-AKLRAD-OH(SEQ ID NO: 23) |
| | (19)H-QKLRASD-OH(SEQ ID NO: 24) |
| | (20)H-AQKLRSD-OH(SEQ ID NO: 25) |
| | (21)H-AQKLRAS-OH(SEQ ID NO: 26) |
| | (24)H-AQKRASD-OH(SEQ ID NO: 27) |
| | (27)H-AQKLASD-OH(SEQ ID NO: 28) |
| (8)H-YERAKSNM-OH(SEQ ID NO: 8) | (9)H-YERAKNM-OH(SEQ ID NO: 29) |
| | (13)H-YERKSNM-OH(SEQ ID NO: 30) |
| | (14)H-YERASNM-OH(SEQ ID NO: 31) |
| | (16)H-YERAKSM-OH(SEQ ID NO: 32) |
| | (22)H-ERAKSNM-OH(SEQ ID NO: 33) |
| | (23)H-YERAKSN-OH(SEQ ID NO: 34) |
| | (28)H-YRAKSNM-OH(SEQ ID NO: 35) |

TABLE 1-2

| Target peptide | Analogue peptide |
|---|---|
| (9)H-FRVDEEFQSPFASQSRGYFLFRPRN-NH2(SEQ ID NO: 9) | (10)H-FRVDEEFQSPFASQSRGYFLFRRN-NH$_2$(SEQ ID NO: 36) |
| (11)H-GGGRG-NH$_2$(SEQ ID NO: 10) | (11)H-GGGG-NH$_2$(SEQ ID NO: 37) |
| (12)Ac-ALRAL-NH$_2$(SEQ ID NO: 11) | (12)Ac-ALAL-NH$_2$(SEQ ID NO: 38) |
| (13)Ac-ALRAL-OH(SEQ ID NO: 12) | (15)Ac-ALAL-OH(SEQ ID NO: 39) |
| (14)H-ALRALRALR-OH(SEQ ID NO: 13) | (17)H-ALALRALR-OH(SEQ ID NO: 40) |
| (15)Ac-GGRGG-NH$_2$(SEQ ID NO: 14) | (18)Ac-GGGG-NH$_2$(SEQ ID NO: 41) |
| (16)H-HSDGTFTSELSRLREGARLQRLLQGLV-NH$_2$(SEQ ID NO: 15) | (30)H-HSDGTFTSELSRLEGARLQRLLQGLV-NH$_2$(SEQ ID NO: 42) |
| (17)Pyr-HWSYlLRP-NH$_2$ | (26)Pyr-HWSYLLRP-NH$_2$(SEQ ID NO: 43) |
| | (31)Pyr-HWSY1LLRP-NH$_2$ |
| (18)H-HVTTV-NH$_2$(SEQ ID NO: 44) | (32)H-VTTV-NH$_2$(SEQ ID NO: 45) |
| | (33)H-hVTTV-NH$_2$ |
| (19)H-YERAKSNM-NH$_2$(SEQ ID NO: 46) | (34)H-YERAKSNL-NH$_2$(SEQ ID NO: 47) |
| (20)H-VKRESYSGVT-NH$_2$(SEQ ID NO: 48) | (36)H-VKRESYSGV-NH$_2$(SEQ ID NO: 55) |
| (21)H-RAVLP-OH(SEQ ID NO: 49) | (37)H-RALP-OH(SEQ ID NO: 56) |
| (22)H-(RC8)RRR((Me)F)R(SC5)-NH$_2$(SEQ ID NO: 50) | (38)H-(RC8)RRRR(SC5)-NH2(SEQ ID NO: 57) |
| (23)Ac-HYFYPEL-NH2(SEQ ID NO: 51) | (39)Ac-HYYPEL-NH$_2$(SEQ ID NO: 58) |
| (24)H-WPVTLNAQTID-NH$_2$(SEQ ID NO: 52) | (40)H-PVTLNAQTID-NH$_2$(SEQ ID NO: 59) |
| (25)H-T((Me)G)RK(Dap)H-OH(SEQ ID NO: 53) | (41)H-((Me)G)RK(Dap)H-OH(SEQ ID NO: 60) |
| (26)Pyr-GPWLEEEEEAYGWMDF-NH$_2$(SEQ ID NO: 54) | (42)Pyr-GPWLEEEEEYGWMDF-NH$_2$(SEQ ID NO: 61) |

The apparatus used in Test examples are as follows.

Peptide synthesizer: "KMS-3" (KOKUSAN CHEMICAL Co., Ltd.).

Mass spectrometer: "6224 TOF LC/MS" and "1260 Infinity series" (Agilent). Ionization condition: ESI (capillary voltage: 3500 V, Fragmentor voltage: 100 V).

HPLC analyzer: "SPD-M20A", "LC-20AD", "SIL-20AC", "DGU-20A", "CTO-20AC", "CBM-20A" (Shimadzu); or "SPD-M20A", "LC-2010C" (Shimadzu); or "1200 series" (Agilent).

(1) Synthesis of Protected Peptide Resin

In syntheses of protected peptide resins, the α-amino group of each constituent amino acid was all protected with a 9-fluorenylmethyloxycarbonyl group (Fmoc group).

Regarding active side chains, the β-carboxyl group of aspartic acid and the γ-carboxyl group of glutamic acid was protected with a tert-butyl group (tBu group); the guanidino group of arginine was protected with a 2,2,4,6,7-pentamethyl-2,3-dihydrobenzofuran-5-ylsulfonyl group (Pbf group); the hydroxyl group of serine and threonine was protected with a tert-butyl group (tBu group); the thiol group of cysteine and the imidazole group of histidine was protected with a trityl group (Trt group); the phenolic hydroxyl group of tyrosine was protected with a tert-butyl group (tBu group); the carboxamide group of asparagine and glutamine was protected with a trityl group (Trt group); the ε-amino group of lysine, the β-amino group of Dap and the indole group of tryptophan were protected with a tert-butyloxycarbonyl group (Boc group).

Regarding resins, (2-chloro)trityl chloride resin (WATANABE CHEMICAL INDUSTRIES, LTD., approx. 1.6 mmol/g) was used for synthesizing a peptide sequence having a C-terminal carboxylic acid; and Fmoc-NH-SAL resin (WATANABE CHEMICAL INDUSTRIES, LTD., approx. 0.43 mmol/g) was used for synthesizing a peptide sequence having a C-terminal carboxamide. In the case of synthesizing the peptide sequence having the C-terminal carboxylic acid, in order to introduce the C-terminal amino acid, a solution of Fmoc amino acid (2.5 equivalents relative to the resin) in DMF, and N,N-diisopropylethylamine (2.5 equivalents relative to the resin) were added to the resin, followed by shaking and stirring for 2 hours or longer. In the case of synthesizing the peptide sequence having the C-terminal carboxamide, to remove the Fmoc group from the resin, a solution of 20% piperidine in DMF was added to the resin, followed by shaking and stirring for not less than 10 minutes and washing the resin 3 to 5 times with DMF, and then to introduce the C-terminal amino acid, a solution of Fmoc amino acid (2.5 equivalents relative to the resin) in DMF, a solution of 1-hydroxybenzotriazole (2.5 equivalents relative to the resin) in DMF, and DIC (2.5 equivalents relative to the resin) were added thereto, followed by shaking and stirring for not less than 40 minutes.

After the C-terminal amino acid was introduced to the resin, the excess amounts of reagents were removed by washing the resin 3 to 5 times with DMF, and then the Fmoc group, the protecting group of the terminal amino group, was removed by shaking and stirring with 20% piperidine at room temperature for 10 minutes or more. The piperidine was removed by washing the resin with DMF 3 to 5 times and then a condensation with the carboxyl group of the Fmoc-protected derivative of the next amino acid in the amino acid sequence of the peptide to be produced was performed. The condensation was performed by adding a solution of the Fmoc-amino acid (2.5 equivalents relative to the resin) in DMF, a solution of 1-hydroxybenztriazole (2.5 equivalents relative to the resin) in DMF, and DIC (2.5 equivalents relative to the resin). Removals of Fmoc group and condensation reactions with Fmoc amino acid were repeated in a similar way until the amino acid sequence of the peptide to be produced was formed to synthesize the protected peptide resin with amino acid sequence of the peptide to be produced.

In a case of synthesizing a peptide having a free amino group at the N-terminus, after the condensation of the Fmoc amino acid of the N-terminus, the Fmoc group was removed by shaking and stirring in a solution of 20% piperidine in DMF at room temperature for 10 minutes or more, and then the piperidine was removed by washing the resin 3 to 5 times with DMF to complete the synthesis of the protected peptide resin. In a case of synthesizing a peptide sequence whose N-terminus was protected by an Ac group, after the N-terminus was converted to a free amino group as described above, a condensation reaction was performed by adding acetic acid (5 equivalents), a solution of N-hydroxysuccinic acid (4.95 equivalents) in DMF, and DIC (5 equivalents) to introduce an Ac group to the N-terminus to synthesize the protected peptide resin having the amino acid sequence of the peptide to be produced. When the N-terminal amino acid residue was (S)- or (R)-pyroglutamic acid, a condensation reaction was carried out by shaking and stirring with (S)- or (R)-Fmoc-pyroglutamic acid chloride (5 equivalents) corresponding to the N-terminal Fmoc amino acid and pyridine (10 equivalents) for at least 40 minutes, and then the Fmoc group was removed by shaking and stirring with a solution of 20% piperidine in DMF for at least 10 minutes at room temperature, and then the piperidine was removed by washing the resin 3 to 5 times with DMF to complete the synthesis of the protected peptide resin.

(2) Synthesis of Crude Peptide Product

In a synthesis of the crude peptide product, the above protected peptide resin having the amino acid sequence of the peptide to be produced was subjected to deprotection and excision from the resin by treating with an acid. When the peptide to be produced had a peptide sequence comprising an amino acid(s) having a sulfur atom, such as cysteine or methionine, the deprotection and excision from the resin were performed by shaking and stirring with TFA/water/ethanedithiol/TIS (94/2.5/2.5/1) for 30 minutes or more at a temperature from cooling with ice to room temperature. When the peptide to be produced had a peptide sequence not comprising an amino acid having a sulfur atom, such as cysteine or methionine, the deprotection and excision from the resin were performed by shaking and stirring with TFA/water/TIS (95/2.5/2.5) for 30 minutes or more at a temperature from cooling with ice to room temperature. After the completion of the reaction, the resin was removed by filtration and washed 3 to 5 times with the solution for deprotection, and the filtrate combined with the washings was concentrated by an evaporator. MTBE was added to the residue, and the resulting precipitates were subjected to a solid-liquid separation by filtration or centrifugation, followed by multiple washes with MTBE to provide the crude peptide product of interest.

Method for Producing (8) H-YERAKSNM-OH (Method A)
(1) To a column made of PP, attached to the peptide synthesizer "KMS-3" was added 187.5 mg (0.30 mmol) of (2-chloro) trityl chloride resin (WATANABE CHEMICAL INDUSTRIES, LTD., approx. 1.6 mmol/g). Five milliliters of DMF was added thereto, and the mixture was shaken and stirred overnight. After removal of the DMF by suction filtration, to the residue were added 2 mL of a solution of Fmoc-Met-OH in DMF (375 mM) (0.75 mmol; 2.5 equivalents), 128 µL of N,N-diisopropylethylamine (0.75 mmol; 2.5 equivalents), and 1 mL of DMF. The resulting mixture was shaken and stirred for 6 hours. After removal of the liquid by suction filtration, the residue was washed with 3 mL of DMF (5 times). To the residue was added 3 mL of a solution of 20% piperidine in DMF, and the mixture was shaken and stirred for 35 minutes. The reaction mixture was filtered by suction, and the residue was washed 5 times with 3 mL of DMF.

(2) To the residue were added 2 mL of a solution of Fmoc-Asn(Trt)-OH in DMF (375 mM) (0.75 mmol; 2.5 equivalents), 1 mL of a solution of 1-hydroxybenzotriazole in DMF (750 mM) (0.75 mmol; 2.5 equivalents), and 116 µL of DIC (0.75 mmol; 2.5 equivalents), and then the mixture was shaken and stirred overnight. After removal of the liquid by suction filtration, the residue was washed 5 times with 3 mL of DMF. To the residue was added 3 mL of a solution of 20% piperidine in DMF, and the mixture was shaken and stirred for 35 minutes. The mixture was filtered by suction, and the residue was washed 5 times with 3 mL of DMF.

(3) With Reference to the step (2) above, the subsequent amino acids were sequentially combined. The order and reaction time of the subsequent amino acids were Fmoc-Ser(tBu)-OH 20 h, Fmoc-Lys(Boc)-OH 45 min, Fmoc-Ala-OH 3 h, Fmoc-Arg(Pbf)-OH 16 h, Fmoc-Glu(tBu)-OH 2.5 h, and Fmoc-Tyr(tBu)-OH 15 h.

(4) To the resulting protected peptide resin was added 3 mL of a solution for deprotection (TFA/water/ethanedithiol/TIS=94/2.5/2.5/1) under ice cooling, and the ice bath was removed and the mixture was shaken and stirred at ambient temperature for 3 hours. The resin was filtered off and washed three times with the solution for deprotection. The filtrate combined with the washings was concentrated by an evaporator. To the residue was added 5 mL of MTBE, and the mixture was stirred overnight under ice cooling. The entire amount of the mixture was transferred to a centrifuge tube, and centrifuged at 3000 rpm for 1 minute, and then the supernatant was removed. To the precipitate was added 2 mL of MTBE, and the mixture was shaken and stirred for 3 minutes, centrifuged at 3000 rpm for 1 minute, and then the supernatant was removed, which was repeated 3 times. The precipitate was dried in vacuo to give 179.5 mg of a crude peptide product of the desired sequence (H-YERAKSNM-OH). The resulting crude peptide product was subjected to confirmation by HPLC and mass spectrometry with an ESI-TOF/MS instrument.

ESI-MS: Calcd. for M: $[M+H]^+=998.47$,
Found M: (m/z): $[M+H]^+=998.4739$
HPLC condition (Condition A)
Column: YMC-triart C18 3 µm, 50×3.0 mm
Mobile phase: A=0.1% aqueous solution of TFA; B=0.1% TFA in acetonitrile
Flow rate: 0.7 mL/min, Temperature: 30° C.
Detection wavelength: 205 nm for target peptide (8) and analogue peptide (22) in [Table 14-2], or 274 nm
Gradient: 2% B (0 min)→2% B (0.2 min)→6.4% B (0.5 min)→6.4% B (11 min)→95% B (15.5 min)→95% B (20.5 min)→2% B (20.6 min)→2% B (29 min) Retention time: around 13.3 min Method for producing (12) Ac-ALRAL-NH$_2$ (Method B)
(1) To a column made of PP, attached to the peptide synthesizer "KMS-3" was added 348.8 mg (0.15 mmol) of Fmoc-NH-SAL resin (WATANABE CHEMICAL INDUS- TRIES, LTD., approx. 0.43 mmol/g). Five milliliters of DMF was added thereto, and the mixture was shaken and stirred for 1 minute, and allowed to stand overnight. After removal of the DMF by suction filtration, to the residue was added 3 mL of a solution of 20% piperidine in DMF, and the mixture was shaken and stirred for 35 minutes. The liquid was filtered off by suction, and the residue was washed 5 times with 3 mL of DMF.

(2) To the residue were added 2 mL of a solution of Fmoc-Leu-OH in DMF (187.5 mM)(0.375 mmol; 2.5 equivalents), 1 mL of a solution of 1-hydroxybenzotriazole in DMF (375 mM) (0.375 mmol; 2.5 equivalents), and 58 µL of DIC (0.375 mmol; 2.5 equivalents), and then the mixture was shaken and stirred for 3 hours. After removal of the liquid by suction filtration, the residue was washed 5 times with 3 mL of DMF. To the residue was added 3 mL of a solution of 20% piperidine in DMF, and the mixture was shaken and stirred for 35 minutes. The liquid was filtered off by suction, and the residue was washed 5 times with 3 mL of DMF.

(3) With Reference to the step (2) above, the subsequent amino acids were sequentially coupled. The order and reaction time of the subsequent amino acids were Fmoc-Ala-OH 2.5 h, Fmoc-Arg(Pbf)-OH 15.5 h, Fmoc-Leu-OH 2.5 h, and Fmoc-Ala-OH 2.5 h. After synthesis of the protected peptide resin whose N-terminus is free amino group, 3 mL of a solution of N-hydroxysuccinic acid in DMF (0.744 mmol; 4.96 equivalents) (248 mM), 43 µL of acetic acid (0.75 mmol; 5 equivalents) and 116 µL of DIC (0.75 mmol; 5 equivalents) were added, and the mixture was shaken and stirred for 16 hours. The liquid was filtered off by suction, and the residue was washed 5 times with 3 mL of DMF and then washed 3 times with 3 mL of MTBE.

(4) To the resulting protected peptide resin was added 3 mL of a solution for deprotection (TFA/water/TIS=95/2.5/2.5) under ice cooling, and the ice bath was removed and the mixture was shaken and stirred at ambient temperature for 4 hours. The resin was filtered off and washed three times with the solution for deprotection. The filtrate combined with the washings was concentrated by an evaporator. To the residue was added 5 mL of MTBE, and the mixture was stirred overnight under ice cooling. The entire amount of the mixture was transferred to a centrifuge tube, and centrifuged at 3000 rpm for 1 minute, and then the supernatant was removed. To the precipitate was added 2 mL of MTBE, and the mixture was shaken and stirred for 3 minutes, centrifuged at 3000 rpm for 1 minute, and then the supernatant was removed, which was repeated 3 times. The precipitate was dried in vacuo to give 90.6 mg of a crude peptide product of the desired sequence (Ac-ALRAL-NH$_2$). The resulting crude peptide product was subjected to confirmation by HPLC and mass spectrometry with an ESI-TOF/MS instrument.

ESI-MS: Calcd. for M: [M+H]$^+$=584.39,
Found M: (m/z): [M+H]$^+$=584.3879

HPLC condition (Condition B)
Column: YMC-PackProC18 3 µm, 50×3.0 mm
Mobile phase: A=0.1% aqueous solution of TFA; B=0.1% TFA in acetonitrile
Flow rate: 0.5 mL/min, Temperature: 30° C.
Detection wavelength: 205 nm
Gradient: 5% B (0 min)→5% B (5 min)→95% B (17 min)→5% B (17.1 min)→5% B (20.1 min)→5% B (24 min)
Retention time: around 10.6 min Method for Producing (1) Ac-YFYPEL-NH$_2$ According to the procedures of Method B, Fmoc-Leu-OH, Fmoc-Glu(tBu)-OH, Fmoc-Pro-OH, Fmoc-Tyr(tBu)-OH, Fmoc-Phe-OH, and Fmoc-Tyr(tBu)-OH were sequentially coupled to 233 mg of Fmoc-NH-SAL resin (0.1 mmol), followed by the Ac protection of the free amino group at the N-terminus to provide a protected peptide resin. Excision from the resin was performed using a solution for deprotection (TFA/Water/TIS=95/2.5/2.5), followed by a similar way to Method B to provide 90.6 mg of a crude peptide product of the desired sequence (Ac-YFYPEL-NH$_2$). The resulting crude peptide product was subjected to confirmation by HPLC and mass spectrometry with an ESI-TOF/MS instrument.

EST-MS: Calcd. for M: [M+H]$^+$=872.42,
Found M: (m/z): [M+H]$^+$=872.4203

HPLC condition (Condition C)
Column: Waters Xbridge C18 3.5 µm, 50×3.0 mm
Mobile phase: A=0.1% aqueous solution of TFA; B=0.1% TFA in acetonitrile
Flow rate: 0.5 mL/min, Temperature: 30° C.
Detection wavelength: 205 nm
Gradient: 20% B (0 min)→20% B (12 min)→95% B (15 min)→95% B (19 min)→20% B (20 min)→20% B (28 min)
Retention time: around 10.2 min Using the methods A or B described above, the target peptides in the tables below were synthesized by solid phase method, respectively. The HPLC analyses were performed with the following conditions in addition to the above HPLC conditions (Conditions A-C).

HPLC condition (Condition D)
Column: Waters Xbridge C18 3.5 µm, 150×4.6 mm
Mobile phase: A=0.1% aqueous solution of TFA; B=0.1% TFA in acetonitrile
Flow rate: 0.5 mL/min, Temperature: 30° C.
Detection wavelength: 275 nm
Gradient: 15% B (0 min)→25% B (1 min)→25% B (12 min)→95% B (14.5 min)→95% B (17 min)→15% B (17.5 min)→15% B (28 min)

HPLC condition (Condition E)
Column: Waters Xbridge C18 3.5 µm, 50×3.0 mm
Mobile phase: A=0.1% aqueous solution of TFA; B=0.1% TFA in acetonitrile
Flow rate: 0.7 mL/min, Temperature: 30° C.
Detection wavelength: 205 nm
Gradient: 20% B (0 min)→35% B (17 min)→95% B (18 min)→95% B (20 min)→20% B (20.5 min)→20% B (28 min)

HPLC condition (Condition F)
Column: Waters Xbridge C18 3.5 µm, 150×4.6 mm
Mobile phase: A=0.1% aqueous solution of TFA; B=0.1% TFA in acetonitrile
Flow rate: 0.5 mL/min, Temperature: 30° C.
Detection wavelength: 279 nm
Gradient: 36% B (0 min)→36% B (12.5 min)→95% B (13 min)→95% B (14.5 min)→36% B (15 min)→36% B (27 min)

HPLC condition (Condition G)
Column: Waters Xbridge C18 3.5 µm, 150×4.6 mm
Mobile phase: A=0.1% aqueous solution of TFA; B=0.1% TFA in acetonitrile
Flow rate: 0.5 mL/min, Temperature: 30° C.
Detection wavelength: 281 nm
Gradient: 22% B (0 min)→25% B (2 min)→25% B (14 min)→95% B (17 min)→95% B (18.5 min)→22% B (19 min)→22% B (30 min)

HPLC condition (Condition H)
Column: Waters Xbridge C18 3.5 µm, 50×3.0 mm
Mobile phase: A=0.1% aqueous solution of TFA; B=0.1% TFA in acetonitrile Flow rate: 0.65 mL/min, Temperature: 30° C.
Detection wavelength: 205 nm
Gradient: 2% B (0 min)→2% B (3 min)→5% B (12 min)→5% B (14 min)→8% B (16 min)→95% B (19 min)→95% B (19.9 min)→2% B (20 min)→2% B (28 min)
HPLC condition (Condition I)
Column: Waters Xbridge C18 3.5 μm, 50×3.0 mm
Mobile phase: A=0.1% aqueous solution of TFA; B=0.1% TFA in acetonitrile
Flow rate: 0.5 mL/min, Temperature: 30° C.
Detection wavelength: 205 nm
Gradient: 23% B (0 min)→25% B (2 min)→25% B (10 min)→35% B (15 min)→95% B (17 min)→95% B (19 min)→23% B (20 min)→23% B (28 min)
HPLC condition (Condition J)
Column: Waters Atlantis T3 3 μm, 150×4.6 mm
Mobile phase: A=0.1% aqueous solution of TFA; B=0.1% TFA in acetonitrile
Flow rate: 1.0 mL/min, Temperature: 30° C.
Detection wavelength: 205 nm
Gradient: 20% B (0 min)→20% B (12 min)→95% B (17 min)→95% B (19 min)→20% B (19.1 min)→20% B (28 min)
HPLC condition (Condition K)
Column: Waters Xbridge Phenyl 3.5 μm, 150×4.6 mm
Mobile phase: A=0.1% aqueous solution of TFA; B=0.1% TFA in acetonitrile
Flow rate: 1.0 mL/min, Temperature: 30° C.
Detection wavelength: 205 nm
Gradient: 5% B (0 min)→5% B (3 min)→95% B (20 min)→5% B (20.1 min)→5% B (26 min)
HPLC condition (Condition L)
Column: Waters Xbridge C18 3.5 μm, 50×3.0 mm
Mobile phase: A=0.1% aqueous solution of TFA; B=0.1% TFA in acetonitrile
Flow rate: 0.5 mL/min, Temperature: 30° C.
Detection wavelength: 205 nm
Gradient: 28% B (0 min)→38% B (12 min)→95% B (15 min)→95% B (19 min)→28% B (20 min)→28% B (28 min)
HPLC condition (Condition M)
Column: Waters Xbridge C18 3.5 μm, 150×4.6 mm
Mobile phase: A=0.1% aqueous solution of TFA; B=0.1% TFA in acetonitrile
Flow rate: 0.65 mL/min, Temperature: 30° C.
Detection wavelength: 205 nm
Gradient: 4% B (0 min)→4% B (3 min)→7% B (8 min)→95% B (15 min)→95% B (15.9 min)→4% B (16 min)→4%
 B (28 min)
HPLC condition (Condition N)
Column: Waters Xbridge C18 3.5 μm, 150×4.6 mm
Mobile phase: A=0.1% aqueous solution of TFA; B=0.1% TFA in acetonitrile
Flow rate: 1.0 mL/min, Temperature: 30° C.
Detection wavelength: 205 nm
Gradient: 0% B (0 min)→3% B (8 min)→95% B (25 min)→95% B (28 min)→0% B (28.5 min)→0% B (35 min)
HPLC condition (Condition 0)
Column: Waters Xbridge C18 3.5 μm, 150×4.6 mm
Mobile phase: A=0.1% aqueous solution of TFA; B=0.1% TFA in acetonitrile
Flow rate: 0.5 mL/min, Temperature: 30° C.
Detection wavelength: 205 nm
Gradient: 25% B (0 min)→25% B (14 min)→95% B (17 min)→95% B (21 min)→0% B (22 min)→0% B (32 min)
HPLC condition (Condition P)
Column: Waters Xbridge C18 3.5 μm, 50×3.0 mm
Mobile phase: A=0.1% aqueous solution of TFA; B=0.1% TFA in acetonitrile
Flow rate: 0.5 mL/min, Temperature: 30° C.
Detection wavelength: 205 nm
Gradient: 20% B (0 min)→25% B (12 min)→25% B (14 min)→95% B (17 min)→95% B (18.5 min)→20% B (19 min)→20% B (28 min)
HPLC condition (Condition Q)
Column: Waters Xbridge C18 3.5 μm, 50×3.0 mm
Mobile phase: A=0.1% aqueous solution of TFA; B=0.1% TFA in acetonitrile
Flow rate: 0.5 mL/min, Temperature: 30° C.
Detection wavelength: 205 nm
Gradient: 3% B (0 min)→5% B (5 min)→5% B (16 min)→95% B (17 min)→95% B (19 min)→3% B (19.1 min)→3% B (28 min)
HPLC condition (Condition R)
Column: Waters Xbridge C18 3.5 μm, 150×4.6 mm
Mobile phase: A=0.1% aqueous solution of TFA; B=0.1% TFA in acetonitrile
Flow rate: 0.6 mL/min, Temperature: 30° C.
Detection wavelength: 275 nm
Gradient: 11% B (0 min)→11% B (10 min) 20% B (12 min)→95% B (15 min)→95% B (17.5 min)→11% B (18 min)→11% B (28 min)
HPLC condition (Condition S)
Column: Waters Xbridge C18 3.5 μm, 150×4.6 mm
Mobile phase: A=0.1% aqueous solution of TFA; B=0.1% TFA in acetonitrile
Flow rate: 0.6 mL/min, Temperature: 30° C.
Detection wavelength: 281 nm
Gradient: 29% B (0 min)→29% B (10 min)→40% B (12 min)→95% B (15 min)→95% B (17.5 min) 29% B (18 min)→29% B (28 min)
HPLC condition (Condition T)
Column: Waters Xbridge C18 3.5 μm, 150×4.6 mm
Mobile phase: A=0.1% aqueous solution of TFA; B=0.1% TFA in acetonitrile
Flow rate: 0.7 mL/min, Temperature: 30° C.
Detection wavelength: 276 nm
Gradient: 10.5% B (0 min)→10.5% B (10 min)→95% B (14 min)→95% B (17 min)→10.5% B (17.1 min)→10.5% B (28 min)
HPLC condition (Condition U)
Column: Waters Xbridge C18 3.5 μm, 150×4.6 mm
Mobile phase: A=0.1% aqueous solution of TFA; B=0.1% TFA in acetonitrile
Flow rate: 0.65 mL/min, Temperature: 30° C.
Detection wavelength: 205 nm
Gradient: 15% B (0 min)→15% B (10 min)→30% B (12 min)→95% B (15 min)→95% B (17.5 min)→15% B (17.6 min)→15% B (29 min)
HPLC condition (Condition V)
Column: Waters Xbridge C18 3.5 μm, 150×4.6 mm
Mobile phase: A=0.1% aqueous solution of TFA; B=0.1% TFA in acetonitrile
Flow rate: 1 mL/min, Temperature: 30° C.
Detection wavelength: 205 nm
Gradient: 17% B (0 min)→17% B (12 min)→95% B (17 min)→95% B (19 min)→17% B (19.1 min)→17% B (26 min)
HPLC condition (Condition W)
Column: YMC Triart C18 3 μm, 50×3.0 mm
Mobile phase: A=0.1% aqueous solution of TFA; B=0.1% TFA in acetonitrile
Flow rate: 0.5 mL/min, Temperature: 30° C.
Detection wavelength: 205 nm Gradient: 5% B (0 min)→95% B (17 min)→5% B (17.1 min)→5% B (23.5 min)
HPLC condition (Condition X)
Column: YMC-PackproC18RS 3 μm, 50×3 mm
Mobile phase: A=0.1% aqueous solution of TFA; B=0.1% TFA in acetonitrile
Flow rate: 0.5 mL/min, Temperature: 30° C.
Detection wavelength: 205 nm
Gradient: 5% B (0 min)→95% B (12 min)→95% B (18 min) 5% B (18.5 min)→5% B (25 min)
HPLC condition (Condition Y)
Column: YMC Triart C18 3 μm, 50×3.0 mm
Mobile phase: A=0.1% aqueous solution of TFA; B=0.1% TFA in acetonitrile
Flow rate: 0.65 mL/min, Temperature: 30° C.
Detection wavelength: 205 nm
Gradient: 2% B (0 min)→2% B (6 min)→5% B (8 min)→8% B (16 min)→95% B (19 min)→95% B (22 min)→2% B (22.1 min)→2% B (28 min)
HPLC condition (Condition Z)
Column: Waters Xbridge C18 3.5 μm, 150×4.6 mm
Mobile phase: A=0.1% aqueous solution of TFA; B=0.1% TFA in acetonitrile
Flow rate: 0.7 mL/min, Temperature: 30° C.
Detection wavelength: 205 nm
Gradient: 10% B (0 min)→10% B (0.2 min)→34% B (0.5 min)→34% B (14 min)→95% B (16 min)→95% B (19 min)→10% B (19.1 min)→10% B (29 min)

TABLE 2-1

| Target peptide | Resin used / Amount of resin | Synthesis method | Yield | ESI-MS Found M | ESI-MS Calcd. for M | HPLC Analysis condition | RT |
|---|---|---|---|---|---|---|---|
| (1) Ac—YFYPEL—NH$_2$ | Resin B 233 mg | Method B | 78 mg | [M+H]$^+$ 872.4203 | [M+H]$^+$ 872.42 | Condition C | around 10.2 min |
| (2) H—YFYPEL—NH$_2$ | Resin B 233 mg | Method B | 83 mg | [M+H]$^+$ 830.4064 | [M+H]$^+$ 830.41 | Condition D | around 11.8 min |
| (3) H—VIRALRRALVALR ALR—OH | Resin A 187.5 mg | Method A | 366 mg | [M+2H]$^{2+}$ 924.1176 | [M+2H]$^{2+}$ 924.11 | Condition E | around 14.5 min |
| (4) H—ARLDVASEFRKKW NKALSR—NH$_2$ | Resin B 233 mg | Method B | 267 mg | [M+3H]$^{3+}$ 820.8034 | [M+3H]$^{3+}$ 820.80 | Condition C | around 9.2 min |
| (5) H—HAEGTFTSDVSSY LEGQAAKEFIAWLVKGRG—OH | Resin A 125 mg | Method A | 440 mg | [M+3H]$^{3+}$ 1118.8891 | [M+3H]$^{3+}$ 1118.90 | Condition F | around 10.4 min |
| (6) H—AGCKNFFWKTFTS C—OH | Resin A 125 mg | Method A | 206 mg | [M+2H]$^{2+}$ 820.3680 [M+2H]$^{2+}$ 820.3734 | [M+2H]$^{2+}$ 820.37 [M+2H]$^{2+}$ 820.37 | Condition G Condition S | around 16.6 min around 8.4 min |
| (7) H—AQKLRASD—OH | Resin A 187.5 mg | Method A | 183 mg | [M+H]$^+$ 888.4879 | [M+H]$^+$ 888.49 | Condition H Condition M | around 17.2 min around 9.2 min |
| (8) H—YERAKSNM—OH | Resin A 187.5 mg | Method A | 179 mg | [M+H]$^+$ 888.4879 | [M+H]$^+$ 888.49 | Condition A | around 13.4 min |
| (9) H—FRVDEEFQSPFAS QSRGYFLFRPRN—NH$_2$ | Resin B 233 mg | Method B | 313 mg | [M+3H]$^{3+}$ 1027.1906 | [M+3H]$^{3+}$ 1027.18 | Condition I | around 9.8 min |
| (12) Ac—ALRAL—NH$_2$ | Resin B 348.8 mg | Method B | 105 mg | [M+H]$^+$ 584.3876 | [M+H]$^+$ 584.39 | Condition B | around 10.4 min |
| (13) Ac—ALRAL—OH | Resin A 187.5 mg | Method A | 124 mg | [M+H]$^+$ 585.3720 | [M+H]$^+$ 585.37 | Condition B | around 10.6 min |

TABLE 2-2

| Target peptide | Resin used / Amount of resin | Synthesis method | Yield | ESI-MS Found M | ESI-MS Calcd. for M | HPLC Analysis condition | RT |
|---|---|---|---|---|---|---|---|
| (14) H—ALRALRALR—OH | Resin A 187.5 mg | Method A | 213 mg | [M+H]$^+$ 1039.6851 | [M+H]$^+$ 1039.68 | Condition J | around 9.7 min |
| (15) Ac—GGRGG—NH$_2$ | Resin B 348.8 mg | Method B | 115 mg | [M+H]$^+$ 444.2319 | [M+H]$^+$ 444.23 | Condition K | around 2.2 min |
| (16) H—HSDGTFTSELSRL REGARLQRLLQGLV—NH$_2$ | Resin B 233 mg | Method B | 313 mg | [M+3H]$^{3+}$ 1013.5576 | [M+3H]$^{3+}$ 1013.56 | Condition L | around 7.2 min |
| (11) H—GGGRG—NH$_2$ | Resin B 348.8 mg | Method B | 72 mg | [M+H]$^+$ 402.2181 | [M+H]$^+$ 402.22 | Condition N | around 3.2 min |
| (17) Pyr—HWSYILRP—NH$_2$ | Resin B 233 mg | Method B | 134 mg | [M+2H]$^{2+}$ 591.3131 | [M+2H]$^{2+}$ 591.31 | Condition O Condition P | around 13.4 min around 7.9 min |

TABLE 2-2-continued

| Target peptide | Resin used Amount of resin | Synthesis method | Yield | ESI-MS Found M | Calcd. for M | HPLC Analysis condition | RT |
|---|---|---|---|---|---|---|---|
| (18) H—HVTTV—NH$_2$ | Resin B 189 mg | Method B | 67 mg | [M +H]$^+$ 555.3249 | [M +H]$^+$ 555.32 | Condition Q | around 8.7 min |
| (19) H—YERAKSNM—NH$_2$ | Resin B 222 mg | Method B | 134 mg | [M +H]$^+$ 997.4871 | [M +H]$^+$ 997.49 | Condition R | around 4.8 min |

TABLE 2-3

| Target peptide | Resin used Amount of resin | Synthesis method | Yield | ESI-MS Found M | Calcd. for M | HPLC Analysis condition | RT |
|---|---|---|---|---|---|---|---|
| (20) H—VKRESYSGVT—NH$_2$ | Resin B 189 mg | Method B | 101 mg | [M +H]$^+$ 1124.6058 | [M +H]$^+$ 1124.61 | Condition T | around 10.1 min |
| (21) H—RAVLP—OH | Resin A 187.5 mg | Method A | 52.5 mg | [M +H]$^+$ 555.3611 | [M +H]$^+$ 555.36 | Condition U | around 14.4 min |
| (22) H—(RC8)RRR((Me)F)R(SC5)—NH$_2$ | Resin B 222 mg | Method B | 99 mg | [M +H]$^+$ 1123.7689 | [M +H]$^+$ 1123.77 | Condition W | around 7.6 min |
| (27) Ac—YHYPEL—NH$_2$ | Resin B 222 mg | Method B | 79 mg | [M +H]$^+$ 862.4088 | [M +H]$^+$ 862.41 | Condition V | around 12.8 min |
| (28) Ac—Y(MeK)YPEL—NH$_2$ | Resin B 222 mg | Method B | 93 mg | [M +H]$^+$ 867.4607 | [M +H]$^+$ 867.46 | Condition V | around 11.7 min |
| (23) Ac—HYFYPEL—NH$_2$ | Resin B 222 mg | Method B | 106 mg | [M +H]$^+$ 1009.4756 | [M +H]$^+$ 1009.48 | Condition X | around 7.5 min |
| (24) H—WPVTLNAQTID—NH$_2$ | Resin B 222 mg | Method B | 114 mg | [M +H]$^+$ 1256.6613 | [M +H]$^+$ 1256.66 | Condition X | around 7.3 min |
| (25) H—T((Me)G)RK(Dap)H—OH | Resin A 125 mg | Method A | 163 mg | [M +H]$^+$ 698.4059 | [M +H]$^+$ 698.41 | Condition Y | around 9.7 min |
| (26) Pyr—GPWLEEEEAYGWMDF—NH$_2$ | Resin B 233 mg | Method B | 215 mg | [M +2H]$^{2+}$ 1049.4321 | [M +2H]$^{2+}$ 1049.43 | Condition Z | around 16.0 min |

Similarly, the analogue peptides shown in the tables below were synthesized by solid phase method using the above methods.

TABLE 3-1

| Analogue peptide | Resin used Amount of resin | Synthesis method | Yield | ESI-MS Found M | Calcd. for M | HPLC Analysis condition | RT |
|---|---|---|---|---|---|---|---|
| (1) Ac—YYPEL—NH$_2$ | Resin B 233 mg | Method B | 65 mg | [M +H]$^+$ 725.3501 | [M +H]$^+$ 725.35 | Condition C Condition V | around 1.9 min around 16.0 min |
| (2) H—YYPEL—NH$_2$ | Resin B 233 mg | Method B | 80 mg | [M +H]$^+$ 683.3391 | [M +H]$^+$ 683.34 | Condition D | around 8.5 min |
| (3) H—VIRALRALVALRALR—OH | Resin A 187.5 mg | Method A | 354 mg | [M +2H]$^{2+}$ 846.0698 | [M +2H]$^{2+}$ 846.07 | Condition E | around 13.6 min |
| (4) H—ARLDVASEFRKKNKALSR—NH$_2$ | Resin B 233 mg | Method B | 258 mg | [M +3H]$^{3+}$ 758.7746 | [M +3H]$^{3+}$ 758.77 | Condition C | around 2.3 min |
| (5) H—HAEGTFTSDVSSYLEGQAAKEFAWLVKGRG—OH | Resin A 125 mg | Method A | 464 mg | [M +3H]$^{3+}$ 1081.2033 | [M +3H]$^{3+}$ 1081.20 | Condition F | around 5.7 min |
| (6) H—AGCKNFFWKTFTS—OH | Resin A 125 mg | Method B | 382 mg | [M +2H]$^{2+}$ 768.8683 | [M +2H]$^{2+}$ 768.87 | Condition G | around 14.2 min |
| (7) H—AQKLRAD—OH | Resin A 187.5 mg | Method A | 127 mg | [M +H]$^+$ 801.4588 | [M +H]$^+$ 801.46 | Condition H | 17.0 min |
| (8) H—AKLRAD—OH | Resin A 187.5 mg | Method A | 115 mg | [M +H]$^+$ 673.4015 | [M +H]$^+$ 673.40 | Condition H | around 15.7 min |
| (19) H—QKLRASD—OH | Resin A 187.5 mg | Method A | 45 mg | [M +H]$^+$ 817.4480 | [M +H]$^+$ 817.45 | Condition M | around 11.5 min |

TABLE 3-1-continued

| Analogue peptide | Resin used | | | Confirmation test | | | |
|---|---|---|---|---|---|---|---|
| | | | | ESI-MS | | HPLC | |
| | Amount of resin | Synthesis method | Yield | Found M | Calcd. for M | Analysis condition | RT |
| (20) H—AQKLRSD—OH | Resin A 187.5 mg | Method A | 151 mg | [M +H]$^+$ 817.4547 | [M +H]$^+$ 817.45 | Condition M | around 5.2 min |
| (21) H—AQKLRAS—OH | Resin A 187.5 mg | Method A | 201 mg | [M +H]$^+$ 773.4053 | [M +H]$^+$ 773.46 | Condition M | around 7.3 min |

TABLE 3-2

| Analogue peptide | Resin used | | | Confirmation test | | | |
|---|---|---|---|---|---|---|---|
| | | | | ESI-MS | | HPLC | |
| | Amount of resin | Synthesis method | Yield | Found M | Calcd. for M | Analysis condition | RT |
| (24) H—AQKRASD—OH | Resin A 187.5 mg | Method A | 42 mg | [M +H]$^+$ 775.4053 | [M +H]$^+$ 775.41 | Condition M | around 5.2 min |
| (9) H—YERAKNM—OH | Resin A 187.5 mg | Method A | 152 mg | [M +H]$^+$ 911.4377 | [M +H]$^+$ 911.44 | Condition A | around 7.3 min |
| (13) H—YERKSNM—OH | Resin A 187.5 mg | Method A | 124 mg | [M +H]$^+$ 927.4348 | [M +H]$^+$ 927.44 | Condition A | around 11.4 min |
| (14) H—YERASNM—OH | Resin A 187.5 mg | Method A | 147 mg | [M +H]$^+$ 870.3745 | [M +H]$^+$ 870.38 | Condition A | around 12.4 min |
| (16) H—YERAKSM—OH | Resin A 187.5 mg | Method A | 150 mg | [M +H]$^+$ 884.4260 | [M +H]$^+$ 884.43 | Condition A | around 6.9 min |
| (22) H—ERAKSNM—OH | Resin A 187.5 mg | Method A | 90 mg | [M +H]$^+$ 835.4087 | [M +H]$^+$ 835.41 | Condition A | around 4.3 min |
| (23) H—YERAKSN—OH | Resin A 187.5 mg | Method A | 175 mg | [M +H]$^+$ 867.4312 | [M +H]$^+$ 867.43 | Condition A | around 14.0 min |
| (10) H—FRVDEEFQSPFASQSRGYFLFRRN—NH$_2$ | Resin B 233 mg | Method B | 289 mg | [M +3H]$^{3+}$ 994.8306 | [M +3H]$^{3+}$ 994.83 | Condition I | around 8.8 min |
| (12) Ac—ALAL—NH$_2$ | Resin B 348.8 mg | Method B | 67 mg | [M +H]$^+$ 428.2874 | [M +H]$^+$ 428.29 | Condition B | around 10.6 min |
| (15) Ac—ALAL—OH | Resin A 1258 mg | Method A | 30 mg | [M +H]$^+$ 429.2710 | [M +H]$^+$ 429.27 | Condition B | around 11.0 min |
| (17) H—ALALRALR—OH | Resin A 187.5 mg | Method A | 224 mg | [M +H]$^+$ 883.5824 | [M +H]$^+$ 883.58 | Condition J | around 12.0 min |
| (18) Ac—GGGG—NH$_2$ | Resin B 233 mg | Method B | 30 mg | [M +H]$^+$ 288.1300 | [M +H]$^+$ 288.13 | Condition K | around 2.3 min |
| (30) H—HSDGTFTSELSRLEGARLQRLLQGLV—NH$_2$ | Resin B 233 mg | Method B | 289 mg | [M +3H]$^{3+}$ 961.5224 | [M +3H]$^{3+}$ 961.52 | Condition L | around 9.7 min |
| (11) H—GGGG—NH$_2$ | Resin B 348.8 mg | Method B | 69 mg | [M +H]$^+$ 246.1180 | [M +H]$^+$ 246.12 | Condition N | around 1.9 min |
| (26) Pyr—HWSYLLRP—NH$_2$ | Resin B 233 mg | Method B | 143 mg | [M +2H]$^{2+}$ 591.3136 | [M +2H]$^{2+}$ 591.31 | Condition O | around 10.0 min |

TABLE 3-3

| Analogue peptide | Resin used | | | Confirmation test | | | |
|---|---|---|---|---|---|---|---|
| | | | | ESI-MS | | HPLC | |
| | Amount of resin | Synthesis method | Yield | Found M | Calcd. for M | Analysis condition | RT |
| (31) Pyr—HWSYILLRP—NH$_2$ | Resin B 233 mg | Method B | 129 mg | [M +H]$^+$ 1294.7055 | [M +H]$^+$ 1294.72 | Condition P | around 14.2 min |
| (32) H—VTTV—NH$_2$ | Resin B 233 mg | Method B | 49 mg | [M +H]$^+$ 418.2660 | [M +H]$^+$ 418.28 | Condition Q | around 5.2 min |
| (33) H—hVTTV—NH$_2$ | Resin B 233 mg | Method B | 61 mg | [M +H]$^+$ 555.3249 | [M +H]$^+$ 555.32 | Condition Q | around 10.9 min |
| (34) H—YERAKSNL—NH$_2$ | Resin B 222 mg | Method B | 119 mg | [M +H]$^+$ 979.5310 | [M +H]$^+$ 979.53 | Condition R | around 6.8 min |
| (35) H—AGcKNFFWKTPTSC—OH | Resin A 125 mg | Method A | 129 mg | [M +2H]$^{2+}$ 820.3865 | [M +2H]$^{2+}$ 820.37 | Condition S | around 7.4 min |

TABLE 3-4

| Analogue peptide | Resin used Amount of resin | Synthesis method | Yield | ESI-MS Found M | Calcd. for M | HPLC Analysis condition | RT |
|---|---|---|---|---|---|---|---|
| (36) H—VKRESYSGV—NH$_2$ | Resin B 233 mg | Method B | 105 mg | [M +H]$^+$ 1023.5577 | [M +H]$^+$ 1023.56 | Condition T | around 8.8 min |
| (37) H—RALP—OH | Resin A 187.5 mg | Method A | 45 mg | [M +H]$^+$ 456.2926 | [M +H]$^+$ 456.29 | Condition U | around 5.8 min |
| (38) H—(RC8)RRRR(SC5)—NH$_2$ | Resin B 222 mg | Method B | 119 mg | [M +H]$^+$ 962.6858 | [M +H]$^+$ 962.68 | Condition W | around 6.6 min |
| (39) Ac—HYYPEL—NH$_2$ | Resin B 222 mg | Method B | 93 mg | [M +H]$^+$ 862.4114 | [M +H]$^+$ 862.41 | Condition X | around 6.9 min |
| (40) H—PVTLNAQTID—NH$_2$ | Resin B 233 mg | Method B | 119 mg | [M +H]$^+$ 1070.5823 | [M +H]$^+$ 1070.58 | Condition X | around 6.6 min |
| (41) H—((Me)G)RK(Dap)H—OH | Resin A 125 mg | Method A | 134 mg | [M +H]$^+$ 597.3584 | [M +H]$^+$ 597.36 | Condition Y | around 6.8 min |
| (42) Pyr—GPWLEEEEYGWMDF—NH$_2$ | Resin B 233 mg | Method B | 222 mg | [M +2H]$^{2+}$ 1013.9123 | [M +2H]$^{2+}$ 1013.91 | Condition Z | around 14.2 min |

1-2: Acid Compound

The following acid compounds were purchased to use.

Sulfuric acid: NACALAI TESQUE, INC., special grade;
Hydrochloric acid: NACALAI TESQUE, INC., 0.1 N special grade;

Tokyo Chemical Industry Co., Ltd.;

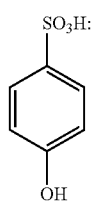

Tokyo Chemical Industry Co., Ltd.;

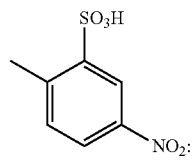

Tokyo Chemical Industry Co., Ltd.;

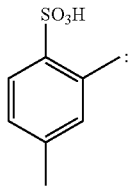

Tokyo Chemical Industry Co., Ltd.;

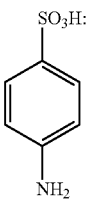

Tokyo Chemical Industry Co., Ltd.;

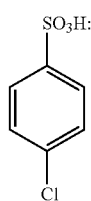

Tokyo Chemical Industry Co., Ltd.;

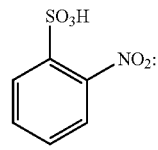

Tokyo Chemical Industry Co., Ltd.;

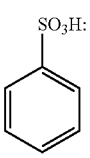

Tokyo Chemical Industry Co., Ltd.;

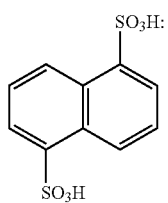

Tokyo Chemical Industry Co., Ltd.;

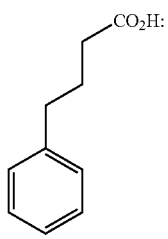

Tokyo Chemical Industry Co., Ltd.;

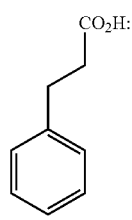

Tokyo Chemical Industry Co., Ltd.;

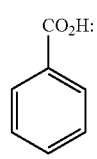

NACALAI TESQUE, INC., special grade;

Wako Pure Chemical, special grade;

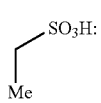

Tokyo Chemical Industry Co., Ltd.;

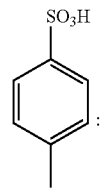

NACALAI TESQUE, INC., first grade;

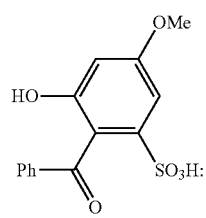

Tokyo Chemical Industry Co., Ltd.;

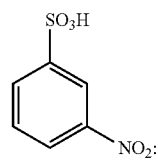

Tokyo Chemical Industry Co., Ltd.;

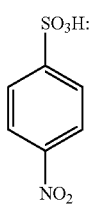

Tokyo Chemical Industry Co., Ltd.

Unless otherwise stated, the following sulfonic acids were synthesized by reacting the corresponding halides with sodium sulfite and subjecting the resulting sulfonic acid sodium salts to acidification with hydrochloric acid.

As a specific example, the synthesis of p-methylbenzyl sulfonic acid is described below:

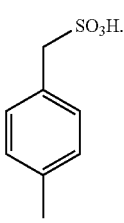

p-Methylbenzyl bromide 1.55 g (7 mmol) was dissolved in 4 mL of ethanol. To the mixture was added 0.97 g of sodium sulfite (7.7 mmol; 1.1 equivalents) and 8 mL of water. The mixture was heated at reflux overnight. After the reaction, the mixture was concentrated by an evaporator to remove ethanol, and the precipitated solid was filtered to give 1.09 g of p-methylbenzylsulfonic acid sodium salt. To 625 mg of the resulting solid were added 1 mL of concentrated hydrochloric acid and 1.5 mL of water, and the mixture was stirred overnight. The liquid was filtered off. The residue was washed 2 times with 0.5 mL of water to give 448 mg of p-methylbenzyl sulfonic acid. $^1$H NMR (400 MHz, D$_2$O) 7.25 (d, J=8.0 Hz, 2H), 7.19 (d, J=7.9 Hz, 2H), 4.07 (s, 2H), 2.28 (s, 3H).

reaction was completed, the reaction mixture was concentrated by an evaporator to remove ethanol, and the precipitated solid was filtered off. To the filtrate was added 1 mL of concentrated hydrochloric acid, and the mixture was evaporated to dryness. To the residue was added 2 mL of water, and the mixture was suspended for 1 hour, and filtered, and the resulting residue was washed with 0.5 mL of water 2 times to give 310 mg of 9-fluorenylmethylsulfonic acid ($^1$H NMR (400 MHz) (CD$_3$OD) 7.91 (d, J=7.6 Hz, 2H), 7.78 (d, J=7.6 Hz, 2H), 7.34 (m, 4H), 4.44 (t, J=6.0 Hz, 1H), 3.28 (m, 2H)).

According to the above synthesis of

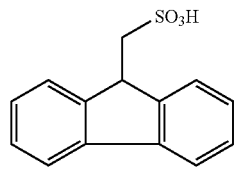 [SMILES: O=S(=O)(O)CC1c2ccccc2-c2ccccc21]

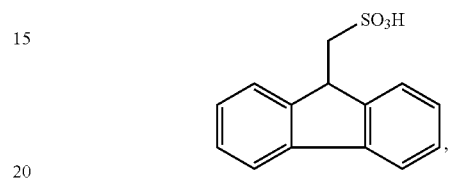

was prepared from the corresponding alcohol compound as follows.

1. In a 50 mL 3-necked flask, 1.18 g (6 mmol) of 9-fluorenyl methanol was dissolved in 9 mL of ethyl acetate, and cooled to 0° C. in an ice bath. To the mixture was added 488 μL (6.3 mmol; 1.05 eq) of methanesulfonyl chloride. 920 μL (6.6 mmol; 1.05 eq) of triethylamine was added dropwise thereto at an internal temperature of 0 to 10° C. After stirring at 0° C. for 26 hours, 10 mL of water and 10 mL of MTBE were added to quench the reaction. The separated organic layer was washed sequentially with 15 mL of saturated aqueous sodium hydrogen carbonate, 15 mL of 0.5 M aqueous sodium hydrogen sulfate, and 15 mL of water. Then the resulting organic layer was concentrated to give 1.28 g of a crude 9-fluorenylmethoxymethanesulfonate. $^1$H NMR (400 MHz, CDCl$_3$) δ:7.78 (d, J=7.8 Hz, 2H), 7.62 (d, J=7.8 Hz, 2H), 7.43 (m, 4H), 4.50 (d, J=7.6 Hz, 2H), 4.31 (t, J=7.6 Hz, 1H), 2.91 (s, 3H).

2. To 1.28 g of the resulting crude 9-fluorenylmethoxymethanesulfonate was added 3 mL of ethanol, and then to the resulting solution were added 7 mL of water and 1.01 g (8 mmol) of sodium sulfite. The mixture was heated and stirred at an internal temperature of 80° C. for 90 h. After the 805 mg of 2-indanol (6 mmol) was used as a starting material to give 1.26 g of 2-indanyloxymethanesulfonate ($^1$H NMR (400 MHz, CDCl$_3$) δ:7.22 (m, 4H), 5.53 (m, 1H), 3.37 (m, 1H), 3.21 (m, 2H), 3.02 (s, 3H)), and 1.26 g of the resulting 2-indanyloxymethanesulfonate was used to give 131 mg of 2-indanylsulfonic acid:

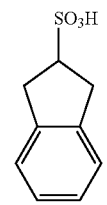 [SMILES: O=S(=O)(O)C1Cc2ccccc2C1]

($^1$H NMR (400 MHz) (CD$_3$OD) 7.19 (m, 2H), 7.12 (m, 2H), 3.80 (m, 1H), 3.34 (m, 3H)).

According to the above procedure for the synthesis of p-methylbenzylsulfonic acid, the sulfonic acids shown in the tables below were synthesized using the corresponding halides.

TABLE 4-1

| Sulfonic acid | Halide | Yield | $^1$H NMR (400 MHz) |
|---|---|---|---|
| ![benzoyl benzyl sulfonic acid] | ![benzoyl benzyl bromide] | 0.15 g | (D$_2$O) 7.71 (m, 4H), 7.66 (t, J = 7.6 Hz, 1H), 7.50 (m, 4H), 4.22 (s, 2H) |
| ![phenylpropyl sulfonic acid] | ![phenylpropyl bromide] | 0.95 g | (CD$_3$OD) 7.23 (m, 4H), 7.15 (t, J = 7.0 Hz, 1H), 2.75 (m, 4H), 2.09 (m, 2H) |

TABLE 4-1-continued

| Sulfonic acid | Halide | Yield | ¹H NMR (400 MHz) |
|---|---|---|---|
| 4-methylphenyl-C(O)-CH₂-SO₃H | 4-methylphenyl-C(O)-CH₂-Br | 0.21 g | (CD$_3$OD) 8.02 (d, J = 8.2 Hz, 2H), 7.33 (d, J = 7.9 Hz, 2H), 4.48 (s, 2H), 2.43 (s, 3H) |
| 3-methoxybenzyl-SO₃H | 3-methoxybenzyl-Br | 0.26 g | (CD$_3$OD) 7.20 (t, J = 7.9 Hz, 1H), 7.00 (m, 2H), 6.81 (m, 1H), 4.02 (s, 2H), 3.79 (s, 3H) |
| 4-nitrobenzyl-SO₃H | 4-nitrobenzyl-Br | 0.47 g | (CD$_3$OD) 8.18 (d, J = 9.2 Hz, 2H), 7.65 (d, J = 9.2 Hz, 2H), 4.17 (s, 2H) |

TABLE 4-2

| Sulfonic acid | Halide | Yield | ¹H NMR (400 MHz) |
|---|---|---|---|
| 4-(CO₂Me)benzyl-SO₃H | 4-(CO₂Me)benzyl-Br | 0.32 g | (CD$_3$OD) 7.96 (d, J = 8.2 Hz, 2H), 7.54 (d, J = 8.3 Hz, 2H), 4.12 (s, 2H), 3.89 (s, 3H) |
| 2-naphthylmethyl-SO₃H | 2-naphthylmethyl-Br | 0.46 g | (CD$_3$OD) 7.87 (m, 4H), 7.61 (m, 1H), 7.46 (m, 2H), 4.24 (s, 2H) |
| 1-naphthylmethyl-SO₃H | 1-naphthylmethyl-Br | 0.16 g | (D$_2$O) 8.17 (d, J = 7.6 Hz, 1H), 7.92 (t, J = 8.0 Hz, 2H), 7.55 (m, 4H), 4.66 (s, 2H) |

TABLE 4-2-continued

| Sulfonic acid | Halide | Yield | NMR |
|---|---|---|---|
| 2-phenylethanesulfonic acid | (2-bromoethyl)benzene | 0.24 g | (D₂O) 7.26 (m, 4H), 7.18 (m, 1H), 3.05 (m, 4H) |
| [4-(sulfomethyl)phenyl]methanesulfonic acid | 1,4-bis(bromomethyl)benzene | 0.13 g | (D₂O) 7.33 (s, 4H), 4.09 (s, 4H) |
| hept-6-yne-1-sulfonic acid | 7-chlorohept-1-yne | 0.53 g | (CD₃OD) 2.81 (t, J = 7.8 Hz, 2H), 2.21 (m, 3H), 1.90 (m, 2H), 1.64 (m, 2H) |

TABLE 4-3

| Sulfonic acid | Halide | Yield | NMR |
|---|---|---|---|
| 2-oxo-2,3,4,5-tetrahydro-1H-benzo[b]azepine-3-sulfonic acid | 3-bromo-4,5-dihydro-1H-benzo[b]azepin-2(3H)-one | 0.15 g | (DMSO-d₆) 9.40 (s, 1H), 7.17 (m, 2H), 7.05 (t, J = 7.4 Hz, 1H), 6.92 (t, J = 7.6 Hz, 1H), 3.32 (dd, J = 8.6 Hz, 11.0 Hz, 1H), 2.67 (m, 2H), 2.39 (m, 2H) |
| 3,3-diphenylpropane-1-sulfonic acid | (3-bromopropane-1,1-diyl)dibenzene | 1.50 g | (CD₃OD) 7.27 (m, 8H), 7.16 (m, 2H), 4.07 (t, J = 8.0 Hz, 1H), 2.72 (m, 2H), 2.53 (m, 2H) |
| [4-(sulfomethyl)-2,3,5-trimethyl-6-(sulfomethyl)phenyl]methanesulfonic acid | 1,3,5-tris(bromomethyl)-2,4,6-trimethylbenzene | 0.19 g | (DMSO-d₆) 3.13 (s, 6H), 2.43 (s, 9H) |

TABLE 4-3-continued
| | | | |
|---|---|---|---|
| 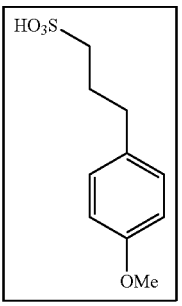 [SMILES: COc1ccc(CCCS(=O)(=O)O)cc1] | 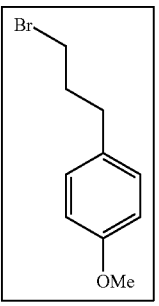 [SMILES: COc1ccc(CCCBr)cc1] | 67 mg | (CD$_3$OD) 7.12 (d, J = 6.4 Hz, 2H), 6.82 (d, J = 6.8 Hz, 2H), 3.75 (s, 3H), 2.77 (m, 2H), 2.66 (t, J = 7.5 Hz, 2H), 2.05 (m, 2H) |
| 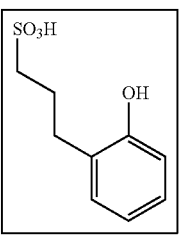 [SMILES: O=S(=O)(O)CCCc1ccccc1O] | 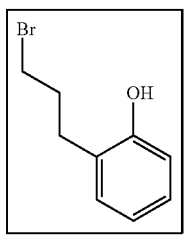 [SMILES: Oc1ccccc1CCCBr] | 0.18 g | (CD$_3$OD) 7.07 (d, J = 7.7 Hz, 1H), 6.99 (t, J = 7.8 Hz, 1H), 6.72 (m, 2H), 2.80 (m, 2H), 2.71 (t, J = 7.4 Hz, 2H), 2.08 (m, 2H) |
TABLE 4-4
| | | | |
|---|---|---|---|
| 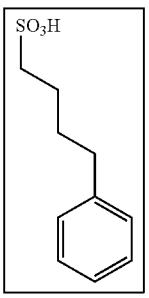 [SMILES: O=S(=O)(O)CCCCc1ccccc1] | 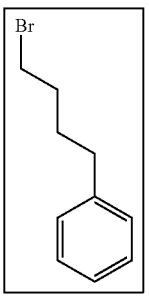 [SMILES: BrCCCCc1ccccc1] | 0.84 g | (CD$_3$OD) 7.23 (m, 4H), 7.15 (t, J = 7.1 Hz, 1H), 6.72 (m, 2H), 2.83 (dd, J = 8.0 Hz, 7.4 Hz, 1H), 2.65 (t, J = 7.4 Hz, 2H), 1.86-1.73 (m, 4H) |
| 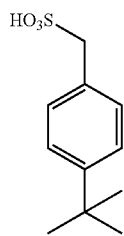 | 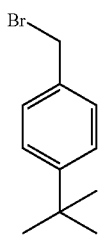 | 1.05 g | (CD$_3$OD) 7.33 (m, 4H), 4.01 (s, 2H), 1.30 (s, 9H) |
| 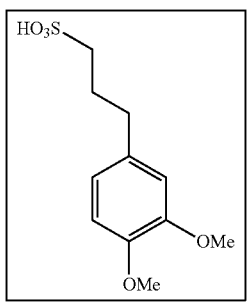 [SMILES: COc1ccc(CCCS(=O)(=O)O)cc1OC] | 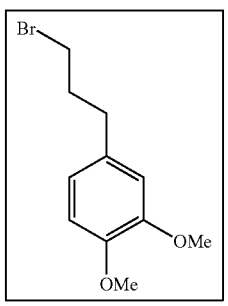 [SMILES: COc1ccc(CCCBr)cc1OC] | 67 mg | (CD$_3$OD) 6.75 (m, 2H), 6.67 (m, 1H), 3.70 (s, 3H), 3.67 (s, 3H), 2.55 (m, 4H), 1.88 (m, 2H) |

TABLE 4-4-continued

| | | | |
|---|---|---|---|
| (3,5-di-t-Bu-4-OMe-phenyl)propyl-SO3H | (3,5-di-t-Bu-4-OH-phenyl)propyl-Br | 6 mg | (DMSO-d$_6$) 6.98 (s, 2H), 5.06 (s, 1H), 2.85 (m, 2H), 2.68 (t, J = 7.3 Hz, 2H), 2.14 (m, 2H) |

15

TABLE 4-5

| | | | |
|---|---|---|---|
| HO$_3$S-CH$_2$CH$_2$-C(Ph)(Ph)-CN | Br-CH$_2$CH$_2$-C(Ph)(Ph)-CN | 7 mg | (CD$_3$OD) 7.42 (m, 8H), 7.34 (m, 2H), 2.91 (m, 2H), 2.81 (m, 2H) |
| Ph$_2$C(SO$_3$H)(2-Cl-C$_6$H$_4$) | Ph$_2$CCl(2-Cl-C$_6$H$_4$) | 126 mg | (DMSO-d$_6$) 8.74 (dd, J = 8.1 Hz, 1.2 Hz, 1H), 7.48 (m, 4H), 7.30 (t, J = 6.4 Hz, 1H), 7.22 (t, J = 6.0 Hz, 1H), 7.12 (m, 7H) |
| HO$_3$S-propyl-(2-OH-4-NO$_2$-phenyl) | Br-propyl-(2-OH-4-NO$_2$-phenyl) | 21 mg | (CD$_3$OD) 8.03 (s, 1H), 7.99 (dd, J = 9.0 Hz, 2.7 Hz, 1H), 6.88 (d, J = 9.0 Hz, 1H), 4.30 (t, J = 5.2 Hz, 2H), 2.89 (t, J = 6.4 Hz, 2H), 2.05 (m, 2H) |
| HO$_3$S-propyl-(4-Br-phenyl) | Br-propyl-(4-Br-phenyl) | 345 mg | (CD$_3$OD) 7.43 (d, J = 8.2 Hz, 2H), 7.17 (d, J = 8.2 Hz, 2H), 2.74 (m, 4H), 2.09 (m, 2H) |

TABLE 4-6

| Product | Starting material | Yield | NMR |
|---|---|---|---|
| HO₃S-(CH₂)₃-C₆H₄-3-NO₂ | Br-(CH₂)₃-C₆H₄-3-NO₂ | 302 mg | (CD₃OD) 8.15 (t, J = 1.8 Hz, 1H), 8.09 (m, 1H), 7.69 (d, J = 7.5 Hz, 1H), 7.55 (t, J = 7.9 Hz, 1H), 2.93 (t, J = 7.8 Hz, 2H), 2.85 (t, J = 7.6 Hz, 2H), 2.16 (m, 2H) |
| HO₃S-(CH₂)₃-C₆H₄-3-CF₃ | Br-(CH₂)₃-C₆H₄-3-CF₃ | 338 mg | (CD₃OD) 7.55 (s, 1H), 7.50 (m, 3H), 2.85 (m, 4H), 2.13 (m, 2H) |
| 1,3,5-tris(SO₃H-CH₂)-benzene | 1,3,5-tris(Br-CH₂)-benzene | 85 mg | (CD₃OD) 7.43 (s, 3H), 4.13 (s, 6H) |
| 4-NC-C₆H₄-CH₂-SO₃H | 4-NC-C₆H₄-CH₂-Br | 833 mg | (CD₃OD) 7.70 (dd, J = 6.5 Hz, 1.9 Hz, 2H), 7.50 (dd, J = 6.5 Hz, 1.9 Hz, 2H), 4.15 (s, 2H) |

40

TABLE 4-7

| Product | Starting material | Yield | NMR |
|---|---|---|---|
| PhCH₂CH₂CH(SO₃H)CH₃ | PhCH₂CH₂CH(Br)CH₃ | 80 mg | (CD₃OD) 7.25 (m, 4H), 7.16 (t, J = 6.8 Hz, 1H), 2.83 (m, 3H), 2.35 (m, 1H), 1.76 (m, 1H), 1.37 (d, J = 6.8 Hz, 3H) |
| CH₂=CH-CH₂CH₂CH₂-SO₃H | CH₂=CH-CH₂CH₂CH₂-Br | 40 mg | (CD₃OD) 5.84 (m, 1H), 5.03 (m, 2H), 2.81 (t, J = 9.8 Hz, 2H), 2.20 (m, 2H), 1.90 (m, 2H) |

TABLE 4-7-continued

| | | 424 mg | (CD$_3$OD) 7.44 (d, J = 7.2 Hz, 2H), 7.32 (m, 2H), 7.22 (m, 1H), 6.64 (d, J = 15.8 Hz, 1H), 6.40 (dd, J = 15.8 Hz, 7.8 Hz, 1H), 3.70 (d, J = 7.8 Hz, 2H) |
|---|---|---|---|

TABLE 4-8

| | | 361 mg | (CD$_3$OD) 7.32 (m, 4H), 7.24 (m, 6H), 4.74 (m, 1H), 2.93 (m, 4H) |
|---|---|---|---|

Synthesis of Benzylsulfonic Acid:

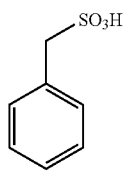

To 1.71 g (10 mmol) of benzyl bromide were added 10 mL of ethanol and 0.76 g (10 mmol) of thiourea, and heated at reflux overnight. After the disappearance of the starting materials was confirmed by TLC, the mixture was concentrated and dried by an evaporator. To the residue was added 10 mL of acetonitrile to give a solution, and the solution was cooled in an ice bath. To the solution were added 2 mL of 2N hydrochloric acid (4 mmol) and 5.34 g of N-chlorosuccinimide (40 mmol) under ice cooling, and the mixture was stirred at room temperature for 1 hour. The reaction mixture was concentrated by an evaporator, and to the residue was added 5 mL of ethyl acetate, and the separated organic layer was concentrated by an evaporator. To the residue were added 5 mL of MTBE and 5 mL of heptane, the precipitated solid was filtered off, and the filtrate was concentrated by an evaporator. The residue was purified by silica gel column chromatography (Silica gel: Fuji SILYSIA CHEMICAL LTD, PSQ-100B, 50 g; Mobile phase: hexane/ethyl acetate=20/1) to give 0.64 g of benzylsulfonyl chloride. To 0.59 g of the resulting benzylsulfonyl chloride was added 5.9 mL of water, and the mixture was heated at reflux for 5 days. The reaction mixture was concentrated to dryness and dried by a vacuum pump to give 0.39 g of benzylsulfonic acid. $^1$H NMR (400 MHz, CD$_3$OD) 7.42 (m, 2H), 7.28 (m, 3H), 4.05 (s, 2H)

Synthesis of p-Carboxybenzylsulfonic Acid

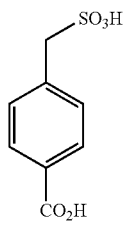

To 0.50 g of p-methoxycarbonylbenzylsulfonic acid synthesized above, 0.6 mL of concentrated hydrochloric acid and 0.6 mL of water were added and the mixture was heated to 90° C. The mixture was heated with stirring at 90° C. overnight, then cooled to room temperature, and then filtered under reduced pressure to collect the precipitated solid to give 0.37 g of p-carboxybenzylsulfonic acid. $^1$H NMR (400 MHz, CD$_3$OD) 7.97 (d, J=8.3 Hz, 2H), 7.53 (d, J=8.2 Hz, 2H), 4.12 (s, 2H)

Abbreviations

TFA: trifluoroacetic acid
IPA: isopropyl alcohol
DMSO: dimethyl sulfoxide
DIC: diisopropylcarbodiimide
TIS: triisopropylsilane
MTBE: methyl tert-butyl ether Test Example 1: Purification of Target Peptide—1
(for Removal of Analogue Peptide)

A crude target peptide and a crude analogue peptide prepared in the above 1-1 were dissolved in 1% TFA in water/acetonitrile=100 to 70/0 to 30, to give 20 mM crude target peptide solution and 20 mM crude analogue peptide solution, respectively (assuming 100% purity of each peptide). Poorly soluble peptides were diluted to about 5 mM (assuming 100% purity of each peptide) and dissolved.

Each acid compound was dissolved in water, or in 10% IPA aqueous solution or 10% DMSO aqueous solution in case where it was difficult to dissolve in water, to give 50 mM acid compound solution.

The crude target peptide solution (1 μmol, assuming 100% purity of the target peptide) and the crude analogue peptide solution (0.1 μmol, assuming 100% purity of the analogue peptide) were mixed. The mixture was mixed with an acid compound solution (1.5 μmol) (the resulting mixture was analyzed by HPLC to provide the value of "before treatment"). The mixture was dried by lyophilization.

To the residue was added 100 μL of IPA, and the mixture was shaken overnight at room temperature.

The resulting slurry was centrifuged (5000 to 15000 rpm, 1 to 5 min), and the resulting cake was washed with 150 μL of IPA 2 times. The filtrate and the washings were combined.

The resulting solid and the filtrate combined with the washings were analyzed by HPLC to provide the values of "solid obtained after treatment" and "filtrate obtained after treatment".

HPLC instruments were the same as those described above.

Measurement conditions: the same as the HPLC conditions A to Z for peptide synthesis.

For peptides comprising aromatic amino acid residue(s), long-wavelength ultraviolet absorption can be attributed exclusively to the aromatic side chain(s). The HPLC detection wavelengths for analyzing such peptides were Condition A (for detection at 274 nm), Condition D, Conditions F to G, and Conditions R to T. Under condition A (for detection at 274 nm), condition R, and condition T, both of the target and analogue peptides had 1 aromatic amino acid residue each. Under condition F, both of the target and analogue peptides had 5 aromatic amino acid residues each. Under condition G and condition S, both of the target and analogue peptides had 4 aromatic amino acid residues each. Under condition D, the target peptide had 3 aromatic amino acid residues, and the analogue peptide had 2 aromatic amino acid residues. That is, the number of aromatic side chains contributing to the long-wavelength ultraviolet absorption at 274 to 281 nm was the same or 1 difference between the target peptide and the analogue peptide, and the ratio of the HPLC area values can be regarded as an approximate molar ratio.

On the other hand, a peptide not comprising an aromatic amino acid residue has no ultraviolet absorption on a long wavelength side, and a short wavelength ultraviolet absorption (205 nm) attributed to a carbonyl group can be used for detection. For example, the target peptide had 10 carbonyl groups and the analogue peptide had 9 carbonyl groups in condition A (for detection at 205 nm) and condition J. Similarly, the target peptide has 6 carbonyl groups and the analogue peptide has 5 carbonyl groups in condition B and condition K, the target peptide has 8 carbonyl groups and the analogue peptide has 7 carbonyl groups in condition C, the target peptide has 16 carbonyl groups and the analogue peptide has 15 carbonyl groups in condition E, the target peptide has 9 carbonyl groups and the analogue peptide has 6 or 8 carbonyl groups in condition H, the target peptide has 31 carbonyl groups and the analogue peptide has 30 carbonyl groups in condition I, the target peptide has 32 carbonyl groups and the analogue peptide has 31 carbonyl groups in condition L, the target peptide has 9 carbonyl groups and the analogue peptide has 8 carbonyl groups in condition M. The number of carbonyl groups that contribute to the short-wavelength ultraviolet absorption at 205 nm is only 1 to 3 different between the target peptide and the analogue peptide, accordingly the ratio of the HPLC area values of the target peptide and the analogue peptide can be regarded as the approximate molar ratio. Although the target peptides (9) and (10) have aromatic side chain(s), they are sufficiently long and contain a large number of carbonyl groups, so they were detected by ultraviolet absorption (205 nm) of carbonyl group in condition I, but can also be detected at the long wavelength side (Both of the target peptide and analogue peptide have six aromatic amino acid residues). Similarly, the target peptide (16) and the analogue peptide (25), each of which has 2 aromatic side chains, were detected at 205 nm.

In condition N, condition O, condition P, condition Q, condition U, condition V, condition W, condition X, condition Y, and condition Z, the short-wavelength ultraviolet absorption (205 nm) of carbonyl group was similarly used for detection.

As shown in the following Equation 1), the ratio (%) of the area of the target peptide to the total area of the target peptide and the analogue peptide was calculated using the HPLC measurement values (Area). The above ratio was regarded as the approximate ratio (%) of the amount of substance (mol) of the target peptide to the total amounts of substance (mol) of the target peptide and the analogue peptide (hereinafter, referred to as "target peptide ratio").

$$\text{Target peptide ratio (\%)} = \frac{\text{Area of target peptide}}{\text{Area of target peptide} + \text{Area of analogue peptide}} \times 100 \quad \text{Equation 1)}$$

$$\approx \frac{\text{Target peptide (mol)}}{\text{Target peptide (mol)} + \text{Analogue peptide (mol)}} \times 100$$

Examination 1: Investigation of Salt Formation

When a peptide is mixed with an acid compound, the N-terminal amino group or a side chain moiety in a basic amino acid (lysine K, arginine R, histidine H etc.) and the acid compound may form a salt.

Based on the change of target peptide ratio (%) in the solid using the following peptides, whether a salt with the peptide and the acid compound is formed was examined.

Target peptide H-YFYPEL-NH$_2$, which does not comprise a basic amino acid, and its analogue peptide H-YYPEL-NH$_2$ having one residue deletion; and The corresponding peptides which are N-terminally protected with an acetyl group (Ac), target peptide Ac-YFYPEL-NH$_2$, and analogue peptide Ac-YYPEL-NH$_2$ having one residue deletion.

In addition, the change of target peptide ratio (%) in the solid was examined using the following peptides, which comprise neither a basic amino acid nor functional group capable of forming a salt:

Target peptide Pyr-GPWLEEEEEAYGWMDF-NH$_2$ and its analogue peptide Pyr-GPWLEEEEEYGWMDF-NH$_2$ having one residue deletion.

The change in the ratio of the target peptide (%) was calculated as "Increased point of target peptide ratio (%)" using Equation 2 below.

Increased point of target peptide ratio (%)=target peptide ratio (%) in the solid obtained after treatment−target peptide ratio (%) of before treatment.     Equation 2):

The results are shown in the tables below.

TABLE 5-1

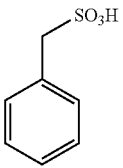 [SMILES: O=S(=O)(O)Cc1ccccc1]

| Target peptide | Analogue peptide | | | No acid compound | Sulfuric acid | |
| --- | --- | --- | --- | --- | --- | --- |
| (1) Ac-YF YPEL—NH₂ | (1) Ac-YYP EL—NH₂ | Before treatment | Area of target peptide | 3778581 | 3778581 | 3778581 |
| | | | Area of analogue peptide | 280840 | 280840 | 280840 |
| | | | Target peptide ratio (%) | 93.1% | 93.1% | 93.1% |
| | | Solid obtained after treatment | Area of target peptide | 1214330 | 938194 | 1191857 |
| | | | Area of analogue peptide | 70516 | 48524 | 59848 |
| | | | Target peptide ratio (%) | 94.5% | 95.1% | 95.2% |
| | | Increased point of target Deotide ratio (%) | | 1.4 | 2.0 | 2.1 |
| (2) H-YFY PEL—NH₂ | (2) H-YYPE L—NH₂ | Before treatment | Area of target peptide | 638016 | 441924 | 464222 |
| | | | Area of analogue peptide | 64491 | 45406 | 47540 |
| | | | Target peptide ratio (%) | 90.8% | 90.7% | 90.7% |
| | | Solid obtained after treatment | Area of target peptide | 41395 | 102094 | 58715 |
| | | | Area of analogue peptide | 4325 | 10239 | 3880 |
| | | | Target peptide ratio (%) | 90.5% | 90.9% | 93.8% |
| | | Increased point of target oeotide ratio (%) | | -0.3 | 0.2 | 3.1 |

TABLE 5-2

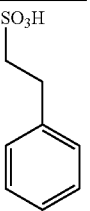

| Target peptide | Analogue peptide | | | No acid compound | Hydrochlonic acid | |
| --- | --- | --- | --- | --- | --- | --- |
| (26) Pyr-GPWLEEEEA YGWMDF—NH₂ | (42) Pyr-GPWLEEEEYG WMDF—NH₂ | Before treatment | Target peptide ratio (%) | 89.1% | 87.5% | 88.9% |
| | | Solid obtained after treatment | Target peptide ratio (%) | 89.0% | 87.5% | 88.9% |
| | | Increased point of target peptide ratio (%) | | -0.1 | 0 | 0 |

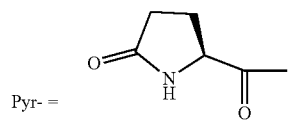

Pyr- =

Regarding Table 5-1:

Regarding the target peptide Ac-YFYPEL-NH₂ and its analogue peptide Ac-YYPEL-NH₂, wherein the N-terminuses are protected with Ac group, the increased points of target peptide ratio (%) are 1.4 points in the case of no acid compound, 2.0 points in the case of sulfuric acid, 2.1 points in the case of the sulfonic acid compound, indicating that there was no large difference in the increased points of target peptide rate (%) in the presence or absence of an acid compound.

On the other hand, regarding the target peptide: H-YFY-PEL-NH₂ and its analogue peptide: H-YYPEL-NH₂, wherein the N-terminuses are free, the increased points of target peptide ratio (%) are -0.3 points in the case of no acid compound, 0.2 points in the case of sulfuric acid, and 3.1 points in the case of the sulfonic acid compound, indicating that the increased point for the sulfonic acid compound was greater than the increased points for no acid compound and sulfuric acid.

When structures of a target peptide and its analogue peptide are similar, the solubility properties of the target peptide and the analogue peptide in a solvent are usually similar. When a peptide forms a solid by forming a salt with a sulfonic acid compound, the solubility property of the solid in the solvent greatly changes as compared with that of the original peptide. Accordingly, in a case where the target peptide exists more than its analogue peptide, the possibility that the target peptide ratio in the solid separated by solid-liquid separation is increased is remarkably increased.

Thus, these results suggest that the sulfonic acid compound formed a salt with the N-terminal amino group of the peptides.

Regarding the case of the target peptide Ac-YFYPEL-NH$_2$ and its analogue peptide Ac-YYPEL-NH$_2$, wherein the N-terminuses are protected with Ac group, it is considered that the increase in target peptide ratio (%), regardless of the presence or absence of the acid compound, was caused by the difference in the dissolution behavior of these peptides in IPA.

Regarding Table 5-2

Regarding the case of the target peptide Pyr-GPWLEEEEAYGWMDF-NH$_2$ and its analogue peptide Pyr-GPWLEEEEYGWMDF-NH$_2$, both of which have no moiety capable of forming a salt, there is no difference of the increased points of target peptide ratio (%) between use of the acid compound and no use of the acid compound.

Examination 2: Effect of Sulfonic Acid Compound

The increased points of the target peptide ratio (%) in the obtained solid were calculated in the same way as described above, using the acid compounds, the target peptides, and the analogue peptides shown in the table below.

The results are shown in the table below.

TABLE 6

| Target peptide | Analogue peptide | | | No acid compound | 2,4-dimethylbenzenesulfonic acid (SO$_3$H, with methyl groups) | 2-nitrobenzenesulfonic acid (SO$_3$H, NO$_2$) |
|---|---|---|---|---|---|---|
| (3) H-VIRALRR ALVALRALR—OH | (3) H-VIRALRAL VALRALR—OH | Before treatment | Target peptide ratio (%) | 88.8% | 89.0% | 88.6% |
| | | Solid obtained after treatment | Target peptide ratio (%) | 88.6% | 89.3% | 89.0% |
| | | Increased point of target peptide ratio (%) | | −0.2 | 0.3 | 0.4 |
| (4) H-ARLDVA SEFRKKWNKA LSR—NH$_2$ | (4) H-ARLDVASE FRKKNKALSR—NH$_2$ | Before treatment | Target peptide ratio (%) | 88.5% | 88.5% | 88.5% |
| | | Solid obtained after treatment | Target peptide ratio (%) | 90.1% | 91.9% | 92.5% |
| | | Increased point of target peptide ratio (%) | | 1.6 | 3.4 | 4.0 |
| (5) H-HAEGTFT SDVSSYLEGQA AKEFIAWLVKG RG—OH | (5) H-HAEGTFTS DVSSYLEGOAAKE FAWLVKGRG—OH | Before treatment | Target peptide ratio (%) | 80.8% | 81.2% | 81.5% |
| | | Solid obtained after treatment | Target peptide ratio (%) | 80.7% | 82.4% | 81.7% |
| | | Increased point of target peptide ratio (%) | | −0.1 | 1.2 | 0.2 |
| (6) H-AGCKNFF WKTFTSC—OH | (6) H-AGCKNFFW KTFTS—OH | Before treatment | Target peptide ratio (%) | 89.9% | 90.4% | 90.6% |
| | | Solid obtained after treatment | Target peptide ratio (%) | 90.0% | 92.5% | 93.4% |
| | | Increased point of target peptide ratio (%) | | 0.1 | 2.1 | 2.8 |

In comparison with the case where no acid compound was used, use of the sulfonic acid compounds increased the increased points of the target peptide ratio (%). These results showed that the sulfonic acid compounds have excellent effects in separating the target peptide and the analogue peptide.

It is considered that this is because the dissolution behavior was changed by the salt formation with the sulfonic acid compounds, as suggested in the Examination 1.

Examination 3: Comparison with Inorganic Acids

The increased points of the ratio (%) of the target peptide in the obtained solid was calculated in the same way as described above, using the acid compounds, the target peptides, and the analogue peptides shown in the table below.

The results are shown in the table below.

TABLE 7

| Target peptide | Analogue peptide | | | Hydrochloric compound | Sulfuric acid | naphthalene-CH₂-SO₃H | 4-(CO₂Me)-C₆H₄-CH₂-SO₃H |
|---|---|---|---|---|---|---|---|
| (7) H-AQK LRASD—OH | (7) H-AQKL RAD—OH | Before treatment | Target peptide ratio (%) | 86.3% | 86.4% | 89.6% | 87.1% |
| | | Solid obtained after treatment | Target peptide ratio (%) | 85.4% | 84.8% | 89.9% | 87.5% |
| | | Increased point of target peptide ratio (%) | | −0.9 | −1.6 | 0.3 | 0.4 |
| | (8) H-AKLR AD—OH | Before treatment | Target peptide ratio (%) | 91.2% | 91.2% | 94.5% | 90.9% |
| | | Solid obtained after treatment | Target peptide ratio (%) | 91.2% | 91.7% | 97.1% | 94.4% |
| | | Increased point of target peptide ratio (%) | | 0.0 | 0.5 | 2.6 | 3.5 |
| (8) H-YER AKSNM—OH | (5) H-YERA KNM—OH | Before treatment | Target peptide ratio (%) | 91.5% | 91.2% | 90.9% | 91.0% |
| | | Solid obtained after treatment | Target peptide ratio (%) | 90.4% | 89.0% | 94.2% | 93.0% |
| | | Increased point of target peptide ratio (%) | | −1.1 | −2.2 | 3.3 | 2.0 |
| (9) H-FRVDEEF QSPFASQSRGY FLFRPRN—NH₂ | (10) H-FRVDEEF QSPFASQSRGYF LFRRN—NH₂ | Before treatment | Target peptide ratio (%) | 93.6% | 94.3% | 85.2% | 93.7% |
| | | Solid obtained after treatment | Target peptide ratio (%) | 92.9% | 95.3% | 96.8% | 97.7% |
| | | Increased point of target peptide ratio (%) | | −0.7 | 1.0 | 11.6 | 4.0 |

The increase points of the target peptide ratio (%) were larger in the cases where the sulfonic acid compounds were used than in the cases where the hydrochloric acid and sulfuric acid were used, which indicates that the sulfonic acid compounds showed an excellent effect in the purification of the target peptide.

Examination 4: Comparison with Carboxylic Acid Compounds

Using the sulfonic acid compounds or carboxylic acid compounds and the target peptides and analogue peptides, shown in the tables below, the increased points of the target peptide ratio (%) in the obtained solid were calculated in the same way as described above.

The results are shown in the tables below.

TABLE 8

| Target peptide | Analogue peptide | | | Ph-(CH₂)₃-SO₃H | Ph-(CH₂)₃-CO₂H | Ph-(CH₂)₂-SO₃H | Ph-(CH₂)₂-CO₂H |
|---|---|---|---|---|---|---|---|
| (9) H-FRVD EEFQSPFA SQSRGYFL FRPRN—NH₂ | (10) H-FRVD EEFQSPFAS QSRGYFLFR RN—NH₂ | Before treatment | Target peptide ratio (%) | 92.2% | 95.0% | 92.3% | 95.6% |
| | | Solid obtained after treatment | Target peptide ratio (%) | 96.5% | 93.6% | 97.1% | 93.3% |
| | | Increased point of target peptide ratio (%) | | 4.3 | −1.4 | 4.8 | −2.3 |

TABLE 9

| Target peptide | Analogue peptide | | | SO₃H-phenyl | CO₂H-phenyl |
|---|---|---|---|---|---|
| (9) H-FRVDEEF QSPFASOSRGYF LFRPRN—NH₂ | (10) H-FRVDEEF QSPFASOSRGYFL FRRN—NH₂ | Before treatment | Target peptide ratio (%) | 91.8% | 94.8% |
| | | Solid obtained after treatment | Target peptide ratio (%) | 96.2% | 93.4% |
| | | Increased point of target peptide ratio (%) | | 4.4 | −1.4 |

The increased points of the target peptide ratio (%) were larger in the cases where the sulfonic acid compounds were used than in the cases where the carboxylic acid compounds were used, which indicates that the sulfonic acid compounds showed an excellent effect in the purification of the target peptide.

Examination 5: Effects of Various Sulfonic Acid Compounds—(1)

When the sulfonic acid compounds, target peptides, and analogue peptides shown in the tables below were used, the target peptide ratio (%) in some of the solids could not be calculated due to analytical problems. Therefore, the change in the target peptide ratio (%) in the filtrate combined with the washings obtained after treatment was calculated as "decreased point of target peptide ratio (%)" using the following Equation (3). Since the concentrations of the target peptide and analogue peptide before and after the treatment are unknown, and the HPLC sensitivities of the target peptide and analogue peptide are not the same, it is not possible to convert the decreased point of target peptide ratio (%) in the filtrate to the increased point of the target peptide ratio (%) in the solid. However, the decrease of the target peptide ratio in the filtrate means the increase of the target peptide ratio in the solid.

$$\text{Decreased point of target peptide ratio (\%)} = (\text{Target peptide ratio (\%) in filtrate obtained after treatment}) - (\text{Target peptide ratio (\%) of before treatment}) \quad \text{Equation 3}$$

The results are shown in the table below.

TABLE 10

| Target peptide | Analogue peptide | | | 3-OMe-benzyl-SO₃H | 4-NO₂-benzyl-SO₃H | 4-CO₂Me-benzyl-SO₃H |
|---|---|---|---|---|---|---|
| (11) H-GGGRG—NH₂ | (11) H-GGGG—NH₂ | Before treatment | Target peptide ratio (%) | 77.0% | 69.7% | 72.9% |
| | | Filtrate obtained after treatment | Target peptide ratio (%) | 70.2% | 69.4% | 67.0% |
| | | Decreased point of target peptide ratio (%) | | 6.8 | 0.3 | 5.9 |
| (12) Ac-ALRAL—NH₂ | (12) Ac-ALAL—NH₂ | Before treatment | Target peptide ratio (%) | 94.5% | 94.4% | 92.4% |
| | | Filtrate obtained after treatment | Target peptide ratio (%) | 86.4% | 79.2% | 82.4% |
| | | Decreased point of target peptide ratio (%) | | 8.1 | 15.2 | 10.0 |
| (8) H-YERAKSN M—OH | (13) H-YERKSN M—OH | Before treatment | Target peptide ratio (%) | 91.1% | 91.8% | 91.8% |
| | | Filtrate obtained after treatment | Target peptide ratio (%) | 75.8% | 76.5% | 72.8% |
| | | Decreased point of target peptide ratio (%) | | 15.3 | 15.3 | 19.0 |
| | (14) H-YERASN M—OH | Before treatment | Target peptide ratio (%) | 89.8% | 90.7% | 90.5% |
| | | Filtrate obtained after treatment | Target peptide ratio (%) | 78.3% | 82.5% | 83.0% |
| | | Decreased point of target peptide ratio (%) | | 11.5 | 8.2 | 7.5 |

TABLE 11

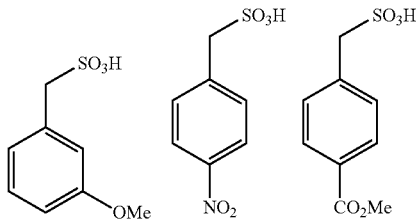

| Target peptide | Analogue peptide | | | OMe | NO2 | CO2Me |
|---|---|---|---|---|---|---|
| (5) H-HAEG TFTSDVSSY LEGQAAKEF IAWLVKGRG—OH | (5) H-HAEG TFTSDVSSY LEGQAAKEF AWLVKGRG—OH | Before treatment | Target peptide ratio (%) | 80.9% | 81.2% | 80.8% |
| | | Filtrate obtained after treatment | Target peptide ratio (%) | 80.2% | 79.9% | 79.6% |
| | | Decreased point of target peptide ratio (%) | | 0.7 | 1.3 | 1.2 |
| (6) H-AGCK NFFWKTFTSC—OH | (6) H-AGCK NFFWKTFTS—OH | Before treatment | Target peptide ratio (%) | 89.4% | 88.0% | 89.4% |
| | | Filtrate obtained after treatment | Target peptide ratio (%) | | | |
| | | Decreased point of target peptide ratio (%) | | 1.1 | 2.0 | 1.2 |

TABLE 12

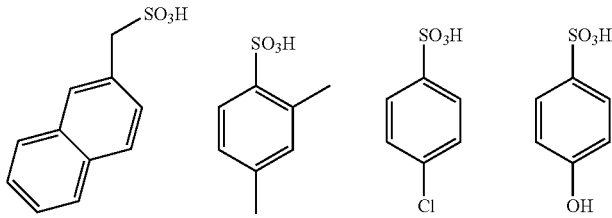

| Target peptide | Analogue peptide | | | naphthyl | 2,4-dimethyl | Cl | OH |
|---|---|---|---|---|---|---|---|
| (12) Ac-ALRAL—NH2 | (12) Ac-ALAL—NH2 | Before treatment | Target peptide ratio (%) | 84.0% | 82.6% | 82.6% | 79.0% |
| | | Filtrate obtained after treatment | Target peptide ratio (%) | 73.5% | 8.0% | 4.5% | 18.4% |
| | | Decreased point of target peptide ratio (%) | | 10.5 | 74.6 | 78.1 | 60.6 |
| (13) Ac-ALRAL—OH | (15) Ac-ALAL—OH | Before treatment | Target peptide ratio (%) | 83.9% | 81.2% | 82.3% | 82.5% |
| | | Filtrate obtained after treatment | Target peptide ratio (%) | 73.1% | 77.5% | 76.7% | 76.6% |
| | | Decreased point of target peptide ratio (%) | | 5.8 | 3.7 | 5.6 | 5.9 |
| (8) H-YERAKSNM—OH | (13) H-YERKSNM—OH | Before treatment | Target peptide ratio (%) | 90.9% | 91.9% | 91.9% | 91.8% |
| | | Filtrate obtained after treatment | Target peptide ratio (%) | 78.3% | 80.9% | 77.3% | 77.3% |
| | | Decreased point of target peptide ratio (%) | | 12.6 | 11.0 | 14.6 | 14.5 |
| | (14) H-YERASNM—OH | Before treatment | Target peptide ratio (%) | 92.3% | 90.7% | 91.0% | 91.1% |
| | | Filtrate obtained after treatment | Target peptide ratio (%) | 84.7% | 84.0% | 83.7% | 81.6% |
| | | Decreased point of target peptide ratio (%) | | 7.6 | 6.7 | 7.3 | 9.5 |
| | (16) H-YERAKSM—OH | Before treatment | Target peptide ratio (%) | 91.3% | 91.3% | 92.1% | 92.0% |
| | | Filtrate obtained after treatment | Target peptide ratio (%) | 80.1% | 89.5% | 89.6% | 87.0% |
| | | Decreased point of target peptide ratio (%) | | 11.2 | 1.8 | 2.5 | 5.0 |

TABLE 13

| Target peptide | Analogue peptide | | | 2-methyl-5-nitro-benzenesulfonic acid | 4-aminobenzenesulfonic acid | naphthalen-1-ylmethanesulfonic acid | 4-(sulfomethyl)benzoic acid |
|---|---|---|---|---|---|---|---|
| (8) H-YER AKSNM—OH | (13) H-YER KSNM—OH | Before treatment | Target peptide ratio (%) | 91.9% | 91.8% | 91.6% | 91.9% |
| | | Filtrate obtained after treatment | Target peptide ratio (%) | 84.6% | 71.3% | 65.4% | 75.5% |
| | | Decreased point of target peptide ratio (%) | | 7.3 | 20.5 | 26.2 | 16.4 |
| | (14) H-YER ASN—OH | Before treatment | Target peptide ratio (%) | 90.4% | 90.5% | 92.5% | 91.0% |
| | | Filtrate obtained after treatment | Target peptide ratio (%) | 88.4% | 79.5% | 74.1% | 82.4% |
| | | Decreased point of target peptide ratio (%) | | 2.0 | 11.0 | 18.4 | 8.6 |
| (14) H-ALR ALRALR—OH | (17) H-ALA LRALR—OH | Before treatment | Target peptide ratio (%) | 89.5% | 90.9% | 90.0% | 90.7% |
| | | Filtrate obtained after treatment | Target peptide ratio (%) | 88.8% | 85.7% | 88.9% | 85.9% |
| | | Decreased point of target peptide ratio (%) | | 1.2 | 5.2 | 1.1 | 4.8 |
| (6) H-AGCK NFFWKTFT SC—OH | (6) H-AGC KNFFWK TFTS—OH | Before treatment | Target peptide ratio (%) | 90.0% | 90.5% | 89.8% | 90.5% |
| | | Filtrate obtained after treatment | Target peptide ratio (%) | 85.9% | 90.4% | 88.9% | 89.9% |
| | | Decreased point of target peptide ratio (%) | | 4.1 | 0.1 | 0.9 | 0.6 |

TABLE 14-1

| Target peptide | Analogue peptide | | | p-methylbenzylsulfonic acid | 4-benzoylbenzylsulfonic acid | benzylsulfonic acid |
|---|---|---|---|---|---|---|
| (15) Ac-GGRGG—NH₂ | (5) Ac-GG GG—NH₂ | Before treatment | Target peptide ratio (%) | 93.7% | 92.6% | 91.2% |
| | | Filtrate obtained after treatment | Target peptide ratio (%) | 74.0% | 69.3% | 67.9% |
| | | Decreased point of target peptide ratio (%) | | 19.7 | 23.3 | 23.3 |
| (7) H-AQKLRASD—OH | (19) H-QKLRA SD—OH | Before treatment | Target peptide ratio (%) | 92.8% | 92.5% | 91.8% |
| | | Filtrate obtained after treatment | Target peptide ratio (%) | 36.5% | 40.2% | 20.6% |
| | | Decreased point of target peptide ratio (%) | | 56.3 | 52.3 | 71.2 |
| | (20) H-AQKLR SD—OH | Before treatment | Target peptide ratio (%) | 82.8% | 92.1% | 92.5% |
| | | Filtrate obtained after treatment | Target peptide ratio (%) | 74.3% | 73.3% | 26.6% |
| | | Decreased point of target peptide ratio (%) | | 18.5 | 18.8 | 65.9 |

TABLE 14-1-continued

| Target peptide | Analogue peptide | | | 4-methylbenzyl-SO₃H | 4-(benzoyl)benzyl-SO₃H | benzyl-SO₃H |
|---|---|---|---|---|---|---|
| | (21) H-AQKLRAS—OH | Before treatment | Target peptide ratio (%) | 91.4% | 91.0% | 90.7% |
| | | Filtrate obtained after treatment | Target peptide ratio (%) | 66.8% | 65.9% | 46.6% |
| | | Decreased point of target peptide ratio (%) | | 24.6 | 25.1 | 44.1 |

TABLE 14-2

| Target peptide | Analogue peptide | | | 4-methylbenzyl-SO₃H | 4-(benzoyl)benzyl-SO₃H | benzyl-SO₃H |
|---|---|---|---|---|---|---|
| (8) H-YERAKSNM—OH | (22) H-ERAKSNM—OH | Before treatment | Target peptide ratio (%) | 94.3% | 94.2% | 94.0% |
| | | Filtrate obtained after treatment | Target peptide ratio (%) | 91.7% | 91.8% | 93.7% |
| | | Decreased point of target peptide ratio (%) | | 2.6 | 2.4 | 0.3 |
| | (13) H-YERKSNM—OH | Before treatment | Target peptide ratio (%) | 91.8% | 91.9% | 90.6% |
| | | Filtrate obtained after treatment | Target peptide ratio (%) | 71.6% | 75.7% | 79.4% |
| | | Decreased point of target peptide ratio (%) | | 20.2 | 16.2 | 11.2 |
| | (23) H-YERAKSN—OH | Before treatment | Target peptide ratio (%) | 87.8% | 87.1% | 84.8% |
| | | Filtrate obtained after treatment | Target peptide ratio (%) | 86.6% | 85.5% | 77.7% |
| | | Decreased point of target peptide ratio (%) | | 1.2 | 1.6 | 7.1 |
| (6) H-AGCKNFFWATFTSC—OH | (6) H-AGCKNFFWKTFTS—OH | Before treatment | Target peptide ratio (%) | 90.3% | 90.4% | 90.20% |
| | | Filtrate obtained after treatment | Target peptide ratio (%) | 89.2% | 87.2% | 90.16% |
| | | Decreased point of target peptide ratio (%) | | 1.1 | 3.2 | 0.04 |

TABLE 15-1

| Target peptide | Analogue peptide | | | 3-phenylpropane-1-sulfonic acid | 2-(4-methylphenyl)-2-oxoethanesulfonic acid | 4-hydroxybenzenesulfonic acid |
|---|---|---|---|---|---|---|
| (13) Ac-ALRAL—OH | (15) Ac-ALAL—OH | Before treatment | Target peptide ratio (%) | 82.3% | 81.4% | 82.5% |
| | | Filtrate obtained after treatment | Target peptide ratio (%) | 78.3% | 76.8% | 76.6% |
| | | Decreased point of target peptide ratio (%) | | 4.0 | 4.6 | 5.9 |
| (12) Ac-ALRAL—NH$_2$ | (19) Ac-ALAL—NH$_2$ | Before treatment | Target peptide ratio (%) | 81.5% | 82.3% | 79.0% |
| | | Filtrate obtained after treatment | Target peptide ratio (%) | 50.4% | 63.4% | 18.4% |
| | | Decreased point of target peptide ratio (%) | | 31.1 | 18.9 | 60.6 |
| (7) H-AQKLRASD—OH | (24) H-AQKRASD—OH | Before treatment | Target peptide ratio (%) | 89.4% | 89.9% | 96.5% |
| | | Filtrate obtained after treatment | Target peptide ratio (%) | 82.9% | 78.1% | 74.5% |
| | | Decreased point of target peptide ratio (%) | | 6.5 | 11.8 | 22.0 |
| (8) H-YERAKSNM—OH | (13) H-YERKSNM—OH | Before treatment | Target peptide ratio (%) | 91.5% | 91.8% | 91.8% |
| | | Filtrate obtained after treatment | Target peptide ratio (%) | 76.1% | 76.8% | 77.3% |
| | | Decreased point of target peptide ratio (%) | | 15.4 | 15.0 | 14.5 |
| | (14) H-YERASNM—OH | Before treatment | Target peptide ratio (%) | 90.7% | 90.6% | 91.1% |
| | | Filtrate obtained after treatment | Target peptide ratio (%) | 83.8% | 83.7% | 81.6% |
| | | Decreased point of target peptide ratio (%) | | 6.9 | 6.9 | 9.5 |

TABLE 15-2

| Target peptide | Analogue peptide | | | 3-phenylpropane-1-sulfonic acid | 2-(4-methylphenyl)-2-oxoethanesulfonic acid | 4-hydroxybenzenesulfonic acid |
|---|---|---|---|---|---|---|
| (3) H-VIRALRR ALVALRALR—OH | (3) H-VIRALRA LVALRALR—OH | Before treatment | Target peptide ratio (%) | 89.2% | 89.4% | 88.9% |
| | | Filtrate obtained after treatment | Target peptide ratio (%) | 87.8% | 89.0% | 87.5% |
| | | Decreased point of target peptide ratio (%) | | 1.4 | 0.4 | 1.4 |
| (16) H-HSDGTF TSELSRLREGAR LQRLLQGLV—NH$_2$ | (30) H-HSDGTF TSELSRLEGARL QRLLQGLV—NH$_2$ | Before treatment | Target peptide ratio (%) | 87.1% | 87.3% | 82.9% |
| | | Filtrate obtained after treatment | Target peptide ratio (%) | 36.5% | 64.4% | 74.6% |
| | | Decreased point of target peptide ratio (%) | | 50.6 | 22.9 | 8.3 |

TABLE 15-2-continued

| Target peptide | Analogue peptide | | | 3-phenylpropane-SO₃H | 2-(4-methylphenyl)-2-oxoethane-SO₃H | 4-hydroxybenzene-SO₃H |
|---|---|---|---|---|---|---|
| (6) H-AGCKNFF WKTFTSC—OH | (6) H-AGCKNFF WKTFTS—OH | Before treatment | Target peptide ratio (%) | 91.5% | 90.2% | 90.309% |
| | | Filtrate obtained after treatment | Target peptide ratio (%) | 85.0% | 87.6% | 90.307% |
| | | Decreased point of target peptide ratio (%) | | 6.5 | 2.6 | 0.002 |

TABLE 16-1

| Target peptide | Analogue peptide | | | 4-methylbenzene-SO₃H | 2-OH-4-OMe-6-SO₃H-benzoyl-Ph | 3-NO₂-benzene-SO₃H | 4-NO₂-benzene-SO₃H |
|---|---|---|---|---|---|---|---|
| (13) Ac-ALRAL—OH | (15) Ac-ALAL—OH | Before treatment | Target peptide ratio (%) | 81.3% | 78.6% | — | 82.6% |
| | | Filtrate obtained after treatment | Target peptide ratio (%) | 78.5% | 67.6% | — | 76.6% |
| | | Decreased point of target peptide ratio (%) | | 2.8 | 11.0 | — | 6.0 |
| (15) Ac-GGRGG—NH₂ | (19) Ac-GGGG—NH₂ | Before treatment | Target peptide ratio (%) | 93.0% | 93.5% | 93.8% | 92.7% |
| | | Filtrate obtained after treatment | Target peptide ratio (%) | 43.8% | 77.9% | 51.7% | 56.8% |
| | | Decreased point of target peptide ratio (%) | | 49.2 | 15.6% | 42.1 | 35.9 |

TABLE 16-2

| Target peptide | Analogue peptide | | | 4-methylbenzene-SO₃H | 2-OH-4-OMe-6-SO₃H-benzoyl-Ph | 3-NO₂-benzene-SO₃H | 4-NO₂-benzene-SO₃H |
|---|---|---|---|---|---|---|---|
| (7)H-AQKLRASD-OH | (24)H-AQKRASD-OH | Before treatment | Target peptide ratio (%) | — | 90.5% | — | 88.5% |
| | | Filtrate obtained after treatment | Target peptide ratio (%) | — | 60.0% | — | 82.0% |
| | | Decreased point of target peptide ratio (%) | | — | 30.5% | — | 6.5% |

TABLE 16-2-continued

| Target peptide | Analogue peptide | | | 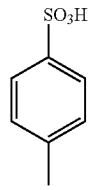 | 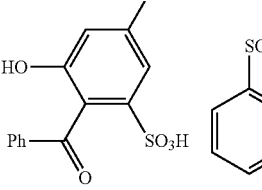 |  | 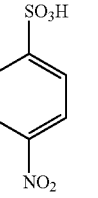 |
|---|---|---|---|---|---|---|---|
| | (27)H-AQKLASD-OH | Before treatment | Target peptide ratio (%) | 94.2% | 91.7% | 90.2% | 91.0% |
| | | Filtrate obtained after treatment | Target peptide ratio (%) | 83.3% | 84.5% | 77.2% | 76.2% |
| | | Decreased point of target peptide ratio (%) | | 10.9 | 7.2 | 13.0 | 14.8 |
| | (20)H-AQKLASD-OH | Before treatment | Target peptide ratio (%) | 92.0% | — | 92.3% | 92.1% |
| | | Filtrate obtained after treatment | Target peptide ratio (%) | 85.5% | — | 76.7% | 85.8% |
| | | Decreased point of target peptide ratio (%) | | 6.5 | — | 15.6% | 6.3 |
| | (21)H-AQKLRAS-OH | Before treatment | Target peptide ratio (%) | 90.7% | 90.5% | 90.5% | 90.7% |
| | | Filtrate obtained after treatment | Target peptide ratio (%) | 66.2% | 48.9% | 74.1% | 59.3% |
| | | Decreased point of target peptide ratio (%) | | 24.5 | 41.6 | 16.4 | 31.4 |
| | (8)H-AKLRAD-OH | Before treatment | Target peptide ratio (%) | 90.9% | 92.2% | 92.3% | 92.5% |
| | | Filtrate obtained after treatment | Target peptide ratio (%) | 40.2% | ≤88.5% | 76.7% | 50.4% |
| | | Decreased point of target peptide ratio (%) | | 50.7 | ≥3.7 | 15.6 | 42.1 |

TABLE 16-3

| Target peptide | Analogue peptide | | | 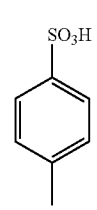 | 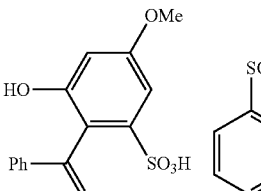 | 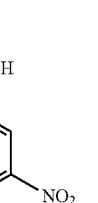 | 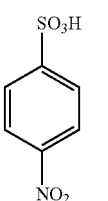 |
|---|---|---|---|---|---|---|---|
| (8)H-YERAKSNM-OH | (28)H-YRAKSNM-OH | Before treatment | Target peptide ratio (%) | 91.0% | 91.4% | 91.7% | 91.3% |
| | | Filtrate obtained after treatment | Target peptide ratio (%) | 87.2% | ≤66.4% | 87.4% | 82.1% |
| | | Decreased point of target peptide ratio (%) | | 3.8% | ≥25.0% | 4.3% | 9.2% |
| | (13)H-YERKSNM-OH | Before treatment | Target peptide ratio (%) | 91.8% | 91.9% | 91.7% | 91.5% |
| | | Filtrate obtained after treatment | Target peptide ratio (%) | 81.4% | 81.6% | 81.8% | 79.9% |
| | | Decreased point of target peptide ratio (%) | | 10.4 | 10.3 | 9.9 | 11.6 |

TABLE 16-3-continued

| Target peptide | Analogue peptide | | | 4-methylbenzenesulfonic acid (SO₃H on toluene) | 2-hydroxy-4-methoxy-6-benzoyl-benzenesulfonic acid | 3-nitrobenzenesulfonic acid | 4-nitrobenzenesulfonic acid |
|---|---|---|---|---|---|---|---|
| | (16)H-YERAKSM-OH | Before treatment | Target peptide ratio (%) | 92.8% | 90.7% | 95.0% | — |
| | | Filtrate obtained after treatment | Target peptide ratio (%) | ≤89.6% | ≤63.4% | 93.6% | — |
| | | Decreased point of target peptide ratio (%) | | ≥3.2 | ≥27.3 | 1.4 | — |
| | (23)H-YERAKSN-OH | Before treatment | Target peptide ratio (%) | 88.3% | 88.4% | — | 88.6% |
| | | Filtrate obtained after treatment | Target peptide ratio (%) | 76.1% | ≤84.8% | — | 86.8% |
| | | Decreased point of target peptide ratio (%) | | 12.2 | ≥3.6 | — | 1.8 |

TABLE 16-4

| Target peptide | Analogue peptide | | | 4-methylbenzenesulfonic acid | 2-hydroxy-4-methoxy-6-benzoyl-benzenesulfonic acid | 3-nitrobenzenesulfonic acid | 4-nitrobenzenesulfonic acid |
|---|---|---|---|---|---|---|---|
| (4)H-ARLDVASEFRKKWNKALSR-NH₂ | (4)H-ARLDVASEFRKKWKALSR-NH₂ | Before treatment | Target peptide ratio (%) | 88.5% | — | — | — |
| | | Filtrate obtained after treatment | Target peptide ratio (%) | 87.8% | — | — | — |
| | | Decreased point of target peptide ratio (%) | | 0.7% | — | — | — |
| (16)H-HSDGTFTSELSRLREGARLQRLLQGLV-NH₂ | (30)H-HSDGTFTSELSRLEGARLQRLLQGLV-NH₂ | Before treatment | Target peptide ratio(%) | 90.8% | — | 83.6% | — |
| | | Filtrate obtained after treatment | Target peptide ratio (%) | ≤86.1% | — | 83.4% | — |
| | | Decreased point of target peptide ratio (%) | | ≥4.7 | — | 0.2 | — |
| (5)H-HAEGTFTSDVSSYLEGQAAKEFIAWLVKGRG-OH | (5)H-HAEGTFTSDVSSYLEGQAAKEFAWLVKGRG-OH | Before treatment | Target peptide ratio(%) | 81.9% | 81.2% | — | 80.5% |
| | | Filtrate obtained after treatment | Target peptide ratio (%) | 74.9% | 80.7% | — | 80.1% |
| | | Decreased point of target peptide ratio (%) | | 7.0 | 0.5 | — | 0.4 |
| (6)H-AGCKNFFWKTFTSC-OH | (6)H-AGCKNFFWKTFTS-OH | Before treatment | Target peptide ratio (%) | 90.9% | 90.7% | 90.3% | 90.3% |
| | | Filtrate obtained after treatment | Target peptide ratio (%) | 89.2% | 88.6% | 85.3% | 88.6% |
| | | Decreased point of target peptide ratio (%) | | 1.7 | 2.1 | 5.0% | 1.7 |
| (17)Pyr-HWSYILRP-NH₂ | (17)Pyr-HWSYILRP-NH₂ | Before treatment | Target peptide ratio (%) | — | 89.9% | 89.0% | 89.0% |
| | | Filtrate obtained after treatment | Target peptide ratio (%) | — | 89.7% | 87.5% | 86.9% |
| | | Decreased point of target peptide ratio (%) | | — | 0.2 | 1.5 | 2.1 |

TABLE 17

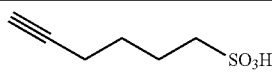

|  |  | Target peptide ratio (%) | | |
|---|---|---|---|---|
| Target peptide | Analogue peptide | Before treatment | Filtrate obtained after treatment | Decreased point of target peptide ratio (%) |
| (5)H-HAEGIFTSDVSSYLEGQAA KEFIAWLVKGRG-OH | (5)H-HAEGTFTSDVSSYLEGQAA KEFAWLVKGRG-OH | 80.6% | 80.3% | 0.3 |
| (6)H-AGCKNFFWKIFTSC-OH | (6)H-AGCKNFFWKIFTS-OH | 90.3% | 89.7% | 0.6 |
| (7)H-AQKLRASD-OH | (20)H-AQKLRSD-OH | 92.4% | 77.9% | 14.5 |
|  | (21)H-AQKLRAS-OH | 90.1% | 68.3% | 21.8 |
| (8)H-YERAKSNM-OH | (13)H-YERKSNM-OH | 91.3% | 73.8% | 17.5 |
|  | (14)H-YERASNM-OH | 90.5% | 82.3% | 8.2 |
|  | (16)H-YERAKSM-OH | 92.0% | 88.3% | 3.7 |
|  | (22)H-ERAKSNM-OH | 94.3% | 90.8% | 3.5 |
| (11)H-GGGRG-NH$_2$ | (11)H-GGGG-NH$_2$ | 74.7% | 72.3% | 2.4 |

Examination 6: Effects of Various Sulfonic Acid Compounds—(2)

The increased points of the target peptide ratio (%) in the obtained solid were calculated in the same way as described above using the acid compounds, the target peptides, and the analogue peptides shown in the tables below.

The results are shown in the tables below.

| Target peptide | Analogue peptide | | | benzenesulfonic acid (PhSO$_3$H) | methylsulfonic acid (MeSO$_3$H) | benzyl sulfonic acid (PhCH$_2$SO$_3$H) | ethanesulfonic acid (MeCH$_2$SO$_3$H) |
|---|---|---|---|---|---|---|---|
| (9)H-FRVD EEFQSPFAS QSRGYFLFR PRN-NH$_2$ | (10)H-FRVDEE FQSPFASQSRGY FLFRRM-NH$_2$ | Before treatment | Target peptide ratio (%) | 91.8% | 93.0% | 91.8% | 94.6% |
|  |  | Solid obtained after treatment | Target peptide ratio (%) | 96.2% | 94.9% | 96.9% | 94.8% |
|  |  | Increased point of target peptide ratio (%) |  | 4.4 | 1.9 | 5.1 | 0.2 |
| (4)H-ARLD VASEFRKKW NKALSE-NH$_2$ | (4)H-ARLDVAS EFRKKNKALSR-NH$_2$ | Before treatment | Target peptide ratio (%) | 88.5% | 88.5% | 88.5% | 88.5% |
|  |  | Solid obtained after treatment | Target peptide ratio (%) | 92.6% | 90.8% | 92.5% | 89.3% |
|  |  | Increased point of target peptide ratio (%) |  | 4.1 | 2.3 | 4.0 | 0.8 |
| (6)H-AGCK NFFWKTFTS C-OH | (6)H-AGCKNFF WKTFTS-OH | Before treatment | Target peptide ratio (%) | 90.5% | 89.9% | 90.2% | 90.3% |
|  |  | Solid obtained after treatment | Target peptide ratio (%) | 93.0% | 90.4% | 93.6% | 90.3% |
|  |  | Increased point of target peptide ratio (%) |  | 2.5 | 0.5 | 3.4 | 0.0 |

TABLE 19

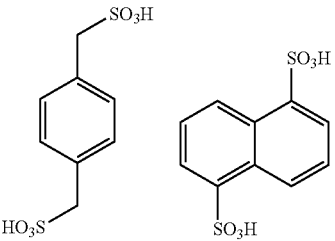

| Target peptide | Analogue peptide | | | p-xylene-α,α'-disulfonic acid | naphthalene-1,5-disulfonic acid |
|---|---|---|---|---|---|
| (6)H-AGCKNFFWKTFTSC-OH | (6)H-AGCKNFFWKTFTS-OH | Before treatment | Target peptide ratio (%) | 91.8% | 90.3% |
| | | Solid obtained after treatment | Target peptide ratio (%) | 91.9% | 93.7% |
| | | Increased point of target peptide ratio (%) | | 0.1 | 3.4 |

TABLE 20

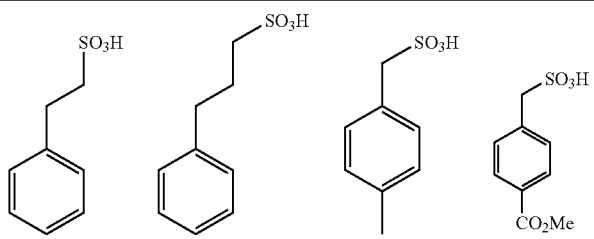

| Target peptide | Analogue peptide | | | 2-phenylethanesulfonic acid | 3-phenylpropanesulfonic acid | p-toluenemethanesulfonic acid | methyl 4-(sulfomethyl)benzoate | 5-hexyne-1-sulfonic acid |
|---|---|---|---|---|---|---|---|---|
| (17)Pyr-HWSYILRP-NH$_2$ | (26) Pyr-HW SYLLR P-NH$_2$ | Before treatment | Target peptide ratio (%) | 90.0% | 88.8% | 89.1% | 89.5% | 89.3% |
| | | Solid obtained after treatment | Target peptide ratio (%) | 95.0% | 93.6% | 96.6% | 93.4% | 90.6% |
| | | Increased point of target peptide ratio (%) | | 5.0 | 4.8 | 7.5 | 3.9 | 1.3 |

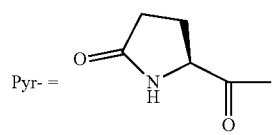

Pyr- = l = D-Leu

TABLE 21

| Target peptide | Analogue peptide | | | Structure 1: phenyl-CH2CH2-SO3H | Structure 2: phenyl-CH2CH2CH2-SO3H | Structure 3: HC≡C-(CH2)4-SO3H |
|---|---|---|---|---|---|---|
| (17)Pyr-HWSYILRP-NH2 | (31)Pyr-HWYILLRP-NH2 | Before treatment | Target peptide ratio (%) | 89.1% | 88.7% | 89.7% |
| | | Solid obtained after treatment | Target peptide ratio (%) | 94.8% | 93.0% | 92.9% |
| | | Increased point of target peptide ratio (%) | | 5.7% | 4.3% | 3.2% |

TABLE 22

| Target peptide | Analogue peptide | | | 1,4-bis(SO3H-CH2)-benzene | 4-CH3-C6H4-CO-CH2-SO3H | 4-NH2-C6H4-SO3H | 4-(PhCO)-C6H4-CH2-SO3H |
|---|---|---|---|---|---|---|---|
| (18)H-HVTTV-NH2 | (32)H-VTTV-NH2 | Before treatment | Target peptide ratio (%) | 94.7% | 95.3% | 94.8% | 95.2% |
| | | Solid obtained after treatment | Target peptide ratio (%) | 98.5% | 99.3% | 97.6% | 98.4% |
| | | Increased point of target peptide ratio (%) | | 3.8 | 4.0 | 2.8 | 3.2 |
| | (33)H-hVTTV-NH2 | Before treatment | Target peptide ratio (%) | 89.3% | 88.9% | 90.0% | 93.4% |
| | | Solid obtained after treatment | Target peptide ratio (%) | 91.2% | 92.6% | 93.8% | 98.0% |
| | | Increased point of target peptide ratio (%) | | 1.9 | 3.7 | 3.8 | 4.6 | h = D-His

TABLE 23

| Target peptide | Analogue peptide | | | 2-methyl-5-nitrobenzenesulfonic acid | 4-methylphenacylsulfonic acid | 3-methoxybenzylsulfonic acid | 4-(carboxy)benzylsulfonic acid |
|---|---|---|---|---|---|---|---|
| (19)H-YERAK SNM-NH$_2$ | (34)H-YERAK SNL-NH$_2$ | Before treatment | Target peptide ratio (%) | 91.2% | 91.2% | 90.7% | 91.1% |
| | | Solid obtained after treatment | Target peptide ratio (%) | 92.2% | 91.3% | 93.5% | 91.4% |
| | | Increased point of target peptide ratio (%) | | 1.0 | 0.1 | 2.8 | 0.3 |
| (6)H-GCKNF FWKT FTSC-OH | (35)H-AGcKN FFWK TFTSC-OH | Before treatment | Target peptide ratio (%) | 74.5% | 76.6% | 76.6% | 74.0 |
| | | Solid obtained after treatment | Target peptide ratio (%) | 76.6% | 76.8% | 76.6% | 74.0% |
| | | Increased point of target peptide ratio (%) | | 2.1 | 0.2 | 0.5 | 4.1 | c = D-Cys

TABLE 24

| Target peptide | Analogue peptide | | | benzazepinone sulfonic acid | 4-tert-butylbenzylsulfonic acid | 3-(2-hydroxyphenyl)propanesulfonic acid | 3-(4-methoxyphenyl)propanesulfonic acid |
|---|---|---|---|---|---|---|---|
| (19)H-YERAK SNM-NH$_2$ | (34)H-YERAK SNL-NH$_2$ | Before teatment | Target peptide ratio (%) | 91.3 | 91.1 | 91.2 | 92.0 |
| | | Solid obtained after treatment | Target peptide ratio (%) | 92.3 | 91.4 | 92.2 | 92.2 |
| | | Increased point of ratio of target peptide ratio (%) | | 1.0 | 0.3 | 1.0 | 0.2 |
| (6)H-A GCKNF FWKT FTSC-OH | (35)H-AGcKN FFWK TFTSC-OH | Before teatment | Target peptide ratio (%) | 76.1 | 74.0 | 74.0 | 76.6 |
| | | Solid obtained after treatment | Target peptide ratio (%) | 76.8 | 78.1 | 77.7 | 77.2 |
| | | Increased point of ratio of target peptide ratio (%) | | 0.7 | 4.1 | 3.7 | 0.6 |

TABLE 25

| Target peptide | Analogue peptide | | | 4-phenylbutane-1-sulfonic acid | 3-(3,5-di-tert-butyl-4-hydroxyphenyl)propane-1-sulfonic acid | 3-(3,4-dimethoxyphenyl)propane-1-sulfonic acid |
|---|---|---|---|---|---|---|
| (19)H-YERAK SNM-NH₂ | (34)H-YERAK SNL-NH₂ | Before teatment | Target peptide ratio (%) | 91.2 | 91.1 | 91.3 |
| | | Solid obtained after treatment | Target peptide ratio (%) | 91.5 | 91.2 | 92.3 |
| | | Increased point of target peptide ratio (%) | | 0.3 | 0.1 | 1.0 |
| (6)H-GCKNF FWKT FTSC-OH | (35)H-AGcKN FFWK TFTSC-OH | Before teatment | Target peptide ratio (%) | 74.2 | 75.6 | 76.6 |
| | | Solid obtained after treatment | Target peptide ratio (%) | 77.2 | 79.2 | 77.8 |
| | | Increased point of target peptide ratio (%) | | 3.0 | 3.6 | 1.2 |

TABLE 26

| Target peptide | Analogue peptide | | | 4,4-diphenylbutane-1-sulfonic acid | 2,4,6-trimethyl-1,3,5-tris(sulfomethyl)benzene |
|---|---|---|---|---|---|
| (6)H-A GCKNF FWKT FTSC-OH | (35)H-AGcKN FFWK TFTSC-OH | Before teatment | Target peptide ratio (%) | 76.9 | 74.9 |
| | | Solid obtained after treatment | Target peptide ratio (%) | 77.1 | 75.3 |
| | | Increased point of target peptide ratio (%) | | 0.2 | 0.4 |

TABLE 27

| Target peptide | Analogue peptide | | | HO3S-CH2CH2-C(Ph)(Ph)-CN (sulfonic acid) | Ph,Ph-C(2-Cl-C6H4)-SO3H | Naphthalene-1,5-disulfonic acid |
|---|---|---|---|---|---|---|
| (20)H-VKRES YSGVT-NH2 | (36)H-VKRES YSGV-NH2 | Before treatment | Target peptide ratio (%) | 79.8% | 80.2% | 78.8% |
| | | Solid obtained after treatment | Target peptide ratio (%) | 88.1% | 80.8% | 84.5% |
| | | Increased point of target peptide ratio (%) | | 8.3 | 0.6 | 5.7 |
| (21)H-RAVLP-OH | (37)H-RALP-OH | Before treatment | Target peptide ratio (%) | 92.9% | 92.9% | 93.0% |
| | | Solid obtained after treatment | Target peptide ratio (%) | 93.7% | 96.2% | 95.1% |
| | | Increased point of target peptide ratio (%) | | 0.8 | 3.3 | 2.1 |
| (27)Ac-YHYPEL-NH2 | (1)Ac-YYPEL-NH2 | Before treatment | Target peptide ratio (%) | 92.3% | 91.7% | 93.5% |
| | | Solid obtained after treatment | Target peptide ratio (%) | 99.1% | 93.8% | 99.0% |
| | | Increased point of target peptide ratio (%) | | 6.8 | 2.1 | 5.5 |
| (28)Ac-Y(MeK)YPEL-NH2 | (1)Ac-YYPEL-NH2 | Before treatment | Target peptide ratio (%) | 90.7% | 91.2% | 90.9% |
| | | Solid obtained after treatment | Target peptide ratio (%) | 93.0% | 93.2% | 98.1% |
| | | Increased point of target peptide ratio (%) | | 2.3 | 2.0 | 7.2 |

MeK = α-Methyllysine

TABLE 28

| Target peptide | Analogue peptide | | | 3-(2-hydroxy-4-nitrophenyl)propane-1-sulfonic acid | 2-benzoyl-3-hydroxy-5-methoxybenzenesulfonic acid | 2-(4-methylphenyl)-2-oxoethanesulfonic acid | 1,4-phenylenedimethanesulfonic acid |
|---|---|---|---|---|---|---|---|
| (21)H-RAVLP-OH | (37)H-RALP-OH | Before treatment | Target peptide ratio (%) | 92.9% | 92.7% | 94.5% | 93.0% |

TABLE 28-continued

| Target peptide | Analogue peptide | | | 3-(2-hydroxy-4-nitrophenyl)propane-1-sulfonic acid | 2-benzoyl-3-hydroxy-5-methoxybenzenesulfonic acid | 2-(4-methylphenyl)-2-oxoethanesulfonic acid | 1,4-bis(sulfomethyl)benzene |
|---|---|---|---|---|---|---|---|
| | | Solid obtained after treatment | Target peptide ratio (%) | 94.0% | 96.8% | 98.2% | 94.3% |
| | | Increased point of target peptide ratio (%) | | 1.1 | 4.1 | 3.7 | 1.3 |
| (27)Ac-YHYPEL-NH$_2$ | (1)Ac-YYPEL-NH$_2$ | Before treatment | Target peptide ratio (%) | 92.3% | 93.5% | 93.5% | 93.7% |
| | | Solid obtained after treatment | Target peptide ratio (%) | 94.1% | 95.4% | 94.4% | 95.9% |
| | | Increased point of target peptide ratio (%) | | 1.8 | 1.9 | 0.9 | 2.2 |
| (28)Ac-Y(MeK)YPEL-NH$_2$ | (1)Ac-YYPEL-NH$_2$ | Before treatment | Target peptide ratio (%) | 91.0% | 90.2% | 90.7% | 91.1% |
| | | Solid obtained after treatment | Target peptide ratio (%) | 91.5% | 92.3% | 92.0% | 94.1% |
| | | Increased point of target peptide ratio (%) | | 0.5 | 2.1 | 1.3 | 3.0 |

MeK = α-Methyllysine

TABLE 29

| Target peptide | Analogue peptide | | | 3-(4-bromophenyl)propane-1-sulfonic acid | 2-(3-nitrophenyl)ethanesulfonic acid | 3-(3,5-di-tert-butyl-4-hydroxyphenyl)propane-1-sulfonic acid |
|---|---|---|---|---|---|---|
| (22)H-(RC8)RRR((Me)F)R(SC5)-NH$_2$ | (38)H-(RC8)RRRR(SC5)-NH$_2$ | Before treatment | Target peptide ratio (%) | 55.7% | 66.6% | 66.2% |
| | | Solid obtained after treatment | Target peptide ratio (%) | 67.7% | 68.2% | 77.3% |
| | | Increased point of target peptide ratio (%) | | 12.0 | 1.6 | 11.1 |

TABLE 29-continued

| Target peptide | Analogue peptide | | | HO₃S-(CH₂)₃-C₆H₄-Br | HO₃S-(CH₂)₃-C₆H₄-NO₂ | HO₃S-(CH₂)₃-(di-tBu)C₆H₂-OH |
|---|---|---|---|---|---|---|
| (27) Ac-YHYPEL-NH₂ | (1)Ac-YYPEL-NH₂ | Before treatment | Target peptide ratio (%) | 92.3% | 92.7% | 92.8% |
| | | Solid obtained after treatment | Target peptide ratio (%) | 93.7% | 93.2% | 94.2% |
| | | | Increased point of target peptide ratio (%) | 1.4 | 0.5 | 1.4 |
| (28) Ac-Y(MeK)YPE-NH₂ | (1)Ac-YYPEL-NH₂ (1)Ac- | Before treatment | Target peptide ratio (%) | 91.3% | 91.1% | 91.0% |
| | | Solid obtained after treatment | Target peptide ratio (%) | 91.8% | 91.5% | 94.5% |
| | | | Increased point of target peptide ratio (%) | 0.5 | 0.4 | 3.5 |

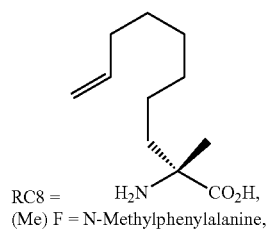

RC8 =
(Me)F = N-Methylphenylalanine,

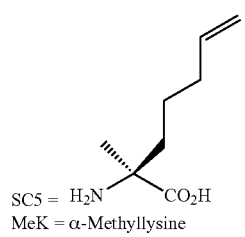

SC5 =
MeK = α-Methyllysine

TABLE 30

| Target peptide | Analogue peptide | | | 3-(trifluoromethyl)phenylpropyl sulfonic acid | benzene-1,3,5-triyltrimethyl trisulfonic acid | 4-cyanobenzyl sulfonic acid | indane-2-sulfonic acid |
|---|---|---|---|---|---|---|---|
| (27) Ac-YHYPEL-NH$_2$ | (1)Ac-YYPEL-NH$_2$ | Before treatment | Target peptide ratio (%) | 92.5% | 92.3% | 92.8% | 92.5% |
| | | Solid obtained after treatment | Target peptide ratio (%) | 96.6% | 98.7% | 96.7% | 95.7% |
| | | | Increased point of target peptide ratio (%) | 3.1 | 6.4 | 3.9 | 3.2 |

TABLE 31

| Target peptide | Analogue peptide | | | hex-5-yne-1-thiosulfonic acid | 4-phenylbutan-2-thiosulfonic acid | 5-phenylpent-4-ene-1-sulfonic acid | cinnamyl thiosulfonic acid |
|---|---|---|---|---|---|---|---|
| (28) Ac-Y(MeK)YPE-NH$_2$ | (1)Ac-YYPEL-NH$_2$ (1)Ac- | Before treatment | Target peptide ratio (%) | 91.9% | 91.2% | 91.1% | 91.0% |
| | | Solid obtained after treatment | Target peptide ratio (%) | 99.2% | 95.0% | 94.4% | 96.3% |
| | | | Increased point of target peptide ratio (%) | 7.3 | 3.8 | 3.3 | 5.3 |

MeK = α-Methyllysine

TABLE 32

| Target peptide | Analogue peptide | | | 2,4-dimethylbenzenesulfonic acid | 6-phenylhexane-1-thiosulfonic acid | 1,3-diphenylpropan-2-sulfonic acid | fluoren-9-ylmethanesulfonic acid |
|---|---|---|---|---|---|---|---|
| (27)Ac-YHYPEL-NH$_2$ | (1)Ac-YYPEL-NH$_2$ | Before treatment | Target peptide ratio (%) | 93.6% | 92.3% | 92.5% | 92.3% |

TABLE 32-continued

| Target peptide | Analogue peptide | | | 2,4-dimethylbenzenesulfonic acid | 5-phenylpentanesulfonic acid derivative | 1,3-diphenylpropane-2-sulfonic acid | fluorene-9-methanesulfonic acid |
|---|---|---|---|---|---|---|---|
| | | Solid obtained after treatment | Target peptide ratio (%) | 94.7% | 94.1% | 92.9% | 93.8% |
| | | Increased point of target peptide ratio (%) | | 1.1 | 1.8 | 0.4 | 1.5 |
| (28) Ac-Y(MeK)YPEL-NH₂ | (1)Ac-YYPEL-NH₂ | Before treatment | Target peptide ratio (%) | 90.8% | 92.4% | 91.1% | 91.9% |
| | | Solid obtained after treatment | Target peptide ratio (%) | 91.3% | 92.6% | 91.3% | 92.1% |
| | | Increased point of target peptide ratio (%) | | 0.5 | 0.2 | 0.2 | 0.2 |
| (23) Ac-HYFYPEL-NH₂ | (39)Ac-HYYPEL-NH₂ | Before treatment | Target peptide ratio (%) | 93.1% | 92.3% | 92.4% | 92.7% |
| | | Solid obtained after treatment | Target peptide ratio (%) | 95.2% | 99.7% | 95.0% | 94.4% |
| | | Increased point of target peptide ratio (%) | | 2.1 | 7.4 | 2.6 | 1.7 |

MeK = α-Methyllysine

TABLE 33

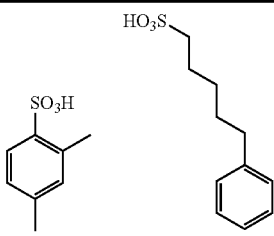

| Target peptide | Analogue peptide | | | naphthalene-2-methanesulfonic acid | substituted benzoyl phenol sulfonic acid | cinnamyl sulfonic acid |
|---|---|---|---|---|---|---|
| (24)H-WPVTLNAQTI-NH₂ | (40)Ac-PVTLNAQTID-NH₂ | Before treatment | Target peptide ratio (%) | 93.7% | 92.8% | 92.4% |
| | | Solid obtained after treatment | Target peptide ratio (%) | 94.2% | 93.2% | 93.3% |
| | | Increased point of target peptide ratio (%) | | 0.5 | 0.4 | 0.9 |

TABLE 34

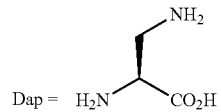

| Target peptide | Analogue peptide | | | 95.5% | 92.6% | 92.9% |
|---|---|---|---|---|---|---|
| (25)H-T((Me)G)RK(Dap)H-OH | (41)H-((Me)G)RK(Dap)H-OH | Before treatment | Target peptide ratio (%) | 95.5% | 92.6% | 92.9% |
| | | Solid obtained after treatment | Target peptide ratio (%) | 96.7% | 94.3% | 94.9% |
| | | | Increased point of target peptide ratio (%) | 1.2 | 1.7 | 2.0 |

(Me)G = N-Methylglycine

Dap = 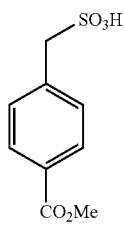

As shown in Tables 5 to 34, the target peptide ratios in the obtained solid were increased (or the target peptide ratios in the obtained filtrate were decreased), and the sulfonic acid compounds showed excellent effects in the purification of various target peptides.

Test Example 2: Evaluation of Solvent—1

The crude target peptide ((8)H-YERAKSNM-OH) and the crude analogue peptide ((13)H-YERKSNM-OH) obtained in the above 1-1 were each dissolved in water/acetonitrile=1/2 to give a crude target peptide solution or a crude analogue peptide solution (10 mM, assuming 100% purity of each peptide).

The acid compound:

was dissolved in water to give a 30 mM acid compound solution.

The crude target peptide solution (1 μmol, assuming 100% purity of the target peptide) and the crude analogue peptide solution (0.1 μmol, assuming 100% purity of the analogue peptide) were mixed.

The mixture was mixed with the acid compound solution (0.9 μmol) (the resulting mixture was subjected to HPLC analysis to give a measurement value of before treatment), and then the mixture was dried by lyophilization.

To the residue was added 100 μL of the solvent shown in the tables below and shaken overnight at room temperature. The resulting slurry was subjected to centrifugal filtration (14000 rpm, 1 min), and the cake was washed with 100 μL of the solvent 2 times. The filtrate was combined with the washings.

The resulting solid and the filtrate combined with the washings were analyzed by HPLC to give the values of "solid obtained after treatment" and "filtrate obtained after treatment".

In the same manner as described above, the decreased points of target peptide ratio (%) in the obtained filtrate combined with the washings was calculated.

In addition, the HPLC area percentage of the target peptide was calculated using the HPLC analysis results of before treatment and the solid obtained after treatment, while the peak of sulfonic acid compound was excluded from the total area.

TABLE 35

| Target peptide | (8)H-YERAKSNM-OH |  |  |
|---|---|---|---|
| Analogue peptide | (13)H-YERKSNM-OH |  |  |
| Solvent | Before treatment Target peptide ratio (%) | Filtrate obtained after treatment Target peptide ratio (%) | Decreased point of target peptide ratio (%) |
| IPA | 91.6% | 64.9% | 26.7 |
| MeOH | 91.8% | 91.5% | 0.3 |
| 1,4-Dioxane/Water (20/1) | 91.2% | 60.1% | 31.1 |
| DME/Water(20/1) | 91.8% | 74.9% | 16.9 |
| THF/Water(20/1) | 91.8% | 48.2% | 43.6 |
| IPA/Water(20/1) | 91.7% | 71.9% | 19.8 |
| Acetone/Water(20/1) | 92.2% | 70.3% | 21.9 |
| Acetonitrile/Water(20/1) | 91.1% | 64.4% | 26.7 |

TABLE 36

| Solvent | Before treatment Area of target peptide (%) | Solid obtained after treatment Area of target peptide (%) |
|---|---|---|
| IPA | 47.13 | 65.29 |
| MeOH | 47.47 | 54.74 |
| 1,4-Dioxane/Water(20/1) | 49.07 | 70.66 |
| DME/Water(20/1) | 49.56 | 72.53 |
| THF/Water(20/1) | 49.61 | 68.26 |
| IPA/Water(20/1) | 49.47 | 66.80 |
| Acetone/Water(20/1) | 48.86 | 65.58 |
| Acetonitrile/water(20/1) | 48.44 | 64.83 |

Area of target peptide (%) = Peak area of target peptide/(Total area − Peak area of sulfonic acid compound) × 100

As shown in Tables 35 and 36, the absolute purity and relative purity of the target peptide were increased. The results show that the sulfonic acid compound is effective in the purification of the target peptide using any of the solvents. That is, a solvent suitable for removing an analogue peptide can be selected by examining a constitution of solvents within the extent reasonably expected to do so.

Test Example 3: Scale-Up

The same target peptide, analogue peptide, and sulfonic acid compound as in Test Example 2 were used.

The crude target peptide, the crude analogue peptide, the sulfonic acid compound were each dissolved in water/acetonitrile=1/2 to give a crude target peptide solution (50 mM, assuming 100% purity of peptide), a crude analogue peptide solution (50 mM, assuming 100% purity of peptide), and a sulfonic acid compound solution (75 mM). The crude target peptide solution 1 mL (50 µmol), and the crude analogue peptide solution 0.1 mL (5 µmol) were mixed.

One milliliter of the sulfonic acid compound solution (75 µmol) was added thereto (the resulting mixture was subjected to HPLC analysis (Condition A) to give a measurement value of before treatment), and then the mixture was dried by lyophilization. To the residue was added 1 mL of IPA, the mixture was dispersed, and then lyophilized again to obtain a residue (67.35 mg).

To the residue was added 2 mL of IPA, the mixture was shaken at 700 rpm for 3 hours, and subjected to centrifugation (14000 rpm, 1 min). The solid and the supernatant were separated and each was lyophilized to give 60.74 mg of a residue derived from the solid portion, and 5.84 mg of a residue derived from the supernatant portion. Each was analyzed by HPLC (Condition A) to give the values of "after treatment". The results are shown in the table below.

TABLE 37

| Target peptide | (8)H-YERAKSNM-OH | | |
|---|---|---|---|
| Analogue peptide | (13)H-YERKSNM-OH | | |
| Solvent | Before treatment Target peptide ratio (%) | Filtrate obtained after treatment Target peptide ratio (%) | Decreased point of target peptide ratio (%) |
| IPA | 91.4% | 63.5% | 27.9 |

Even when the scale was increased, similar results as in Test example 2 were obtained.

Test Example 4: Removal of Sulfonic Acid Compound

The same target peptide, analogue peptide, and sulfonic acid compound as in Test example 3 were used.

The crude target peptide, the crude analogue peptide, the sulfonic acid compound were each dissolved in water/acetonitrile=1/2 to give a crude target peptide solution (50 mM, assuming 100% purity of peptide), a crude analogue peptide solution (50 mM, assuming 100% purity of peptide), and a sulfonic acid compound solution (75 mM). One milliliter of the crude target peptide solution (50 µmol) and 0.1 mL of the crude analogue peptide (5 µmol) were mixed.

One milliliter of the sulfonic acid compound solution (75 µmol) was added thereto (the resulting mixture was subjected to HPLC analysis (Condition A) to give a measurement value of before treatment), and then the mixture was dried by lyophilization. To the residue was added 1 mL of IPA, the mixture was dispersed, and then lyophilized again to give a residue (70.93 mg).

To the residue was added 5 mL of IPA, the mixture was shaken at 700 rpm for 3.5 hours, and subjected to centrifugation (14000 rpm, 1 min). The solid and the supernatant were separated. The solid was washed with 1 mL of IPA. The solid and the supernatant combined with the washing were respectively lyophilized to give 59.58 mg of a residue derived from the solid portion, and 5.40 mg of a residue derived from the supernatant portion.

Oasis WAX Cartridge (6 cc/150 mg) (Waters) was pretreated with 1 mL of 1N aqueous solution of sodium hydroxide, 7 mL of water (purified water), and 2 mL of water/MeOH (10/1) in this order.

Fifteen point seven four milligrams of the residue derived from the solid was dissolved in 1 mL of water/MeOH (10/1), (the resulting mixture was subjected to HPLC analysis (Condition A) to give a measurement value of after treatment, where the sulfonic acid was eluted at around 5.1 min). The mixture was loaded onto the pretreated Oasis WAX Cartridge (6 cc/150 mg), and 9 mL of water/MeOH (10/1) was passed through the cartridge. The solution passed through the cartridge was analyzed by HPLC (Condition A) to confirm removal of the sulfonic acid compound and give a measurement value after removal of sulfonic acid. The solution was lyophilized to give 9.47 mg of a residue.

The following table shows the HPLC area percentage of the target peptide in the HPLC analysis of the solution before the treatment with the sulfonic acid compound, of the solid obtained after the treatment, and of the sample after removal of the sulfonic acid compound.

TABLE 38

| Area of Target peptide (%) | | |
|---|---|---|
| Before treatment | After treatment | After removal of sulfonic acid compound |
| 42.85 | 61.59 | 76.44 |

Area of target peptide (%) =

$$\frac{\text{Peak area of target peptide}}{\text{(Total area} - \text{Peak area of sulfonic acid compound)}} \times 100$$

Test Example 5: Evaluation of Solvent-2

The crude target peptide ((8)H-YERAKSNM-OH) and the crude analogue peptide ((23)H-YERAKSN-OH) obtained in the above 1-1 were each dissolved in water/acetonitrile=1/2 to give a crude target peptide solution and a crude analogue peptide solution (10 mM, assuming 100% purity of each peptide).

The sulfonic acid compound:

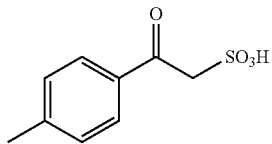

was dissolved in water to give a 50 mM sulfonic acid compound solution.

The crude target peptide solution (1 μmol, assuming 100% purity of the target peptide) and the crude analogue peptide solution (0.1 μmol, assuming 100% purity of the analogue peptide) were mixed.

The mixture was mixed with the sulfonic acid compound solution (1.5 μmol) (the resulting mixture was subjected to HPLC analysis to give a measurement value of before treatment), and then the mixture was dried by lyophilization.

To the residue was added 100 μL of the solvent shown in the tables below and the mixture was shaken overnight at room temperature. The resulting slurry was subjected to centrifugal filtration (14000 rpm, 1 min), and the cake was washed with 100 μL of the solvent 2 times. The filtrate was combined with the washings.

The resulting solid and the filtrate combined with the washings were analyzed by HPLC to give the values of "solid obtained after treatment" and "filtrate obtained after treatment".

In the same manner as described above, the decreased points of target peptide ratio (%) in the obtained filtrate combined with the washings were calculated.

In addition, the HPLC area percentage of the target peptide was calculated using the HPLC analysis results of before treatment and the solid obtained after treatment, while regarding the solid obtained after treatment the peak of sulfonic acid compound was excluded from the total area.

The results are shown in the tables below.

As shown in the tables below, the absolute purity and relative purity of the target peptide were increased. The results show that the sulfonic acid compound is effective in the purification of the target peptide using any of the solvents.

TABLE 39

| Target peptide | (8)H-YERAKSNM-OH | | |
|---|---|---|---|
| Analogue peptide | (23)H-YERAKSN-OH | | |
| Solvent | Before treatment Target peptide ratio (%) | Filtrate obtained after treatment Target peptide ratio (%) | Decreased point of target peptide ratio (%) |
| IPA | 93.2% | 61.3% | 31.9 |
| MeOH | ≥92.4% | 89.8% | ≥2.6 |
| 1,4-Dioxane/Water(20/1) | ≥92.9% | 77.3% | ≥15.6 |
| DME/Water(20/1) | ≥92.5% | 70.3% | ≥22.2 |
| IPA/Water(20/1) | ≥92.7% | 76.5% | ≥16.2 |
| Acetone/Water(20/1) | ≥92.7% | 47.1% | ≥45.6 |
| Acetonitrile/Water(20/1) | ≥91.9% | 32.4% | ≥59.5 |

TABLE 40

| Solvent | Before treatment Area of target peptide (%) | Solid obtained after treatment Area of target peptide (%) |
|---|---|---|
| IPA | 45.99 | 64.44 |
| MeOH | 43.91 | 51.47 |
| 1,4-Dioxane/Water(20/1) | 46.03 | 65.65 |
| DME/Water(20/1) | 44.24 | 65.46 |
| THF/Water(20/1) | 46.08 | 62.48 |
| IPA/Water(20/1) | 45.20 | 64.40 |
| Acetone/Water(20/1) | 46.07 | 60.27 |
| Acetonitrile/Water(20/1) | 43.31 | 62.53 |

Area of target peptide (%) = Peak area of target peptide/(Total area − Peak area of sulfonic acid compound) × 100

Test Example 6: Purification of Target Peptide—2

With respect to the target peptides, analogue peptides, and sulfonic acid compounds shown in the table below, the HPLC area percentage of the target peptide in the solution before treatment and in the solid obtained after treatment was calculated based on the results of the HPLC analysis performed in Test example 1, while the peak of sulfonic acid compound was excluded from the total area.

TABLE 41

| Target peptide | Analogue peptide | Sulfonic acid compound | HPLC condition | Area of target peptide (%) Before treatment | Area of target peptide (%) Solid obtained after treatment |
|---|---|---|---|---|---|
| (14)H-ALRALRALR-OH | (17)H-ALALRALR-OH | 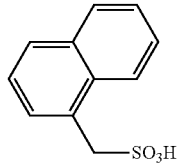 | J | 60.35 | 71.05 |
| (8)H-YERAKSNM-OH | (23)H-YERAKSN-OH | 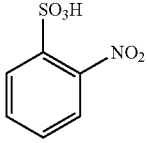 | A | 41.50 | 61.69 |
| (8)H-YERAKSNM-OH | (23)H-YERAKSN-OH | 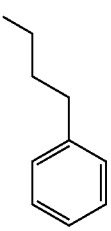 | A | 42.88 | 61.75 |

Area of target peptide (%) = Peak area of target peptide/(Total area-Peak area of sulfonic acid compound) × 100

Test Example 7: Purification of Target Peptide—3

(1) This test was performed in the same manner as Test Example 1, using H-AQKLRASD-OH (referred to as target peptide (7) in Table 1) as a crude analogue peptide, H-QKL-RASD-OH (referred to as analogue peptide (19) in Table 1) as a crude target peptide, and the same sulfonic acid compounds as Table 14-1. The peptides were obtained in "1-1: Synthesis of Peptide".

The results are shown in the table below.

TABLE 42

| Target peptide | Analogue peptide | | | 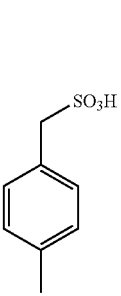 | 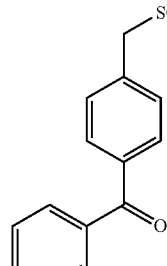 | 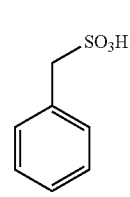 [SMILES: O=S(=O)(O)Cc1ccccc1] |
|---|---|---|---|---|---|---|
| H-QKLRASD-OH | H-AQKLRASD-OH | Before treatment | Target peptide ratio (%) | 83.3% | 90.3% | 91.3% |
| | | Filtration obtained after treatment | Target peptide ratio (%) | 83.0% | 77.7% | 32.5% |
| | | Decreased point of target peptide ratio (%) | | 0.3 | 12.6 | 58.8 |

(2) Similarly, this test was performed in the same manner as Test example 1, using H-AQKLRASD-OH (referred to as target peptide (7) in Table 1) as a crude analogue peptide, H-AQKLRSD-OH (referred to as analogue peptide (20) in Table 1) as a crude target peptide, and the same sulfonic acid compound as Table 16-2. The results are shown in the table below.

TABLE 43

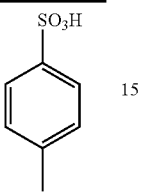

| Target peptide | Analogue peptide | | | |
|---|---|---|---|---|
| H-AQKLRSD-OH | H-AQKLRASD-OH | Before treatment | Target peptide ratio (%) | 76.6 |
| | | Filtration obtained after treatment | Target peptide ratio (%) | 74.5 |
| | | Decreased point of target peptide ratio (%) | | 2.1 |

(3) Similarly, this test was performed in the same manner as Test example 1, using H-YERAKSNM-OH (referred to as target peptide (8) in Table 1) as a crude analogue peptide, H-YERAKNM-OH (referred to as analogue peptide (9) in Table 1) as a crude target peptide, and the same sulfonic acid compounds as Table 7. The results are shown in the table below.

TABLE 44

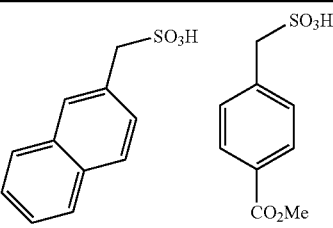

| Target peptide | Analogue peptide | | | | |
|---|---|---|---|---|---|
| H-YERAKNM-OH | H-YERAKSNM-OH | Before treatment | Target peptide ratio (%) | 89.7 | 89.8 |
| | | Solid obtained after treatment | Target peptide ratio (%) | 91.1 | 91.3 |
| | | Increased point of target peptide ratio (%) | | 1.4 | 1.5 |

(4) Similarly, this test was performed in the same manner as Test example 1, using H-YERAKSNM-OH (referred to as target peptide (8) in Table 1) as a crude analogue peptide, H-YERAKSN-OH (referred to as analogue peptide (23) in Table 1) as a crude target peptide, and the same sulfonic acid compounds as Table 14-2. The results are shown in the table below.

TABLE 45

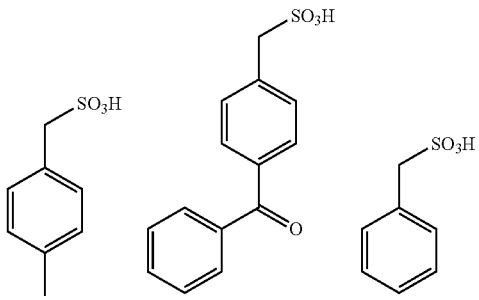

| Target peptide | Analogue peptide | | | SO3H-CH2-C6H4-CH3 (benzyl) | SO3H-CH2-C6H4-CO-C6H5 | SO3H-CH2-C6H5 |
|---|---|---|---|---|---|---|
| H-YERAKSN-OH | H-YERAKSNM-OH | Before treatment | Target peptide ratio (%) | 91.7 | 92.9 | 93.1 |
| | | Filtration obtained after treatment | Target peptide ratio (%) | 81.5 | 91.3 | 92.5 |
| | | Decreased point of target peptide ratio (%) | | 10.2 | 1.6 | 0.6 |

(5) Similarly, this test was performed in the same manner as Test example 1, using H-AQKLRASD-OH (referred to as target peptide (7) in Table 1) as a crude analogue peptide, H-AQKRASD-OH (referred to as analogue peptide (24) in Table 1) as a crude target peptide, and the same sulfonic acid compound as Table 16-2. The results are shown in the table below.

TABLE 46

| Target peptide | Analogue peptide | | | 3-NO2-C6H4-SO3H |
|---|---|---|---|---|
| H-AQKLRSD-OH | H-AQKLRASD-OH | Before treatment | Target peptide ratio (%) | 88.5 |
| | | Filtration obtained after treatment | Target peptide ratio (%) | 79.1 |
| | | Decreased point of target peptide ratio (%) | | 9.4 |

In Test Example 7, in order to further prove that the method of the present invention is a highly versatile peptide purification method, the molar ratio of the target peptide to the analogue peptide of Test Example 1 was reversed, that is, the analogue peptide of Test example 1 was used as a target peptide, and the target peptide of Test example 1 was used as an analogue peptide.

Specifically, Test example 1, Table 14-1, shows the results of a model in which the target peptide (7)H-AQKLRASD-OH and analogue peptide (19)H-QKLRASD-OH were mixed in a molar ratio of about 10:1. On the other hand, Test example 7 was performed using the same sulfonic acid compounds, with a model of reversed molar ratio (theoretical value), i.e. (7)H-AQKLRASD-OH:(19)H-QKLRASD-OH=about 1:10.

In addition, regarding the following combinations of target peptide and analogue peptide in Test example 1, Test example 7 was performed using the reversed molar ratio (theoretical value), with the same sulfonic acid compounds as Test example 1:

target peptide (7)H-AQKLRASD-OH and analogue peptide (20)H-AQKLRSD-OH in Table 16-2;

target peptide (8)H-YERAKSNM-OH and analogue peptide (9)H-YERAKNM-OH in Table 7;

target peptide (8)H-YERAKSNM-OH and analogue peptide (23)H-YERAKSN-OH in Table 14-2;

target peptide (7)H-AQKLRASD-OH and analogue peptide (24)H-AQKLRSD-OH in Table 16-2.

The results of Test Example 7 clearly show that even when the mixing ratio was reversed, that is, even when the analogue peptide of Test Example 1 was used as a target peptide and the target peptide of Test Example 1 was used as an analogue peptide, the relative purity of the target peptide relative to the analogue peptide in the solid was increased (or reduced in the liquid).

Test Example 8: Effects of Various Sulfonic Acid Compounds (Removal of Multiple Analogue Peptides)

Using multiple crude analogue peptide solutions (0.1 μmol each, assuming 100% purity of peptide), the increased point of target peptide ratio (%) to each analogue peptide in the obtained solid was calculated in the same manner as in Test Example 1.

The results are shown in the tables below.

TABLE 47

| Target peptide | Analogue peptide | | | 2-phenylethyl-SO₃H | naphthalen-1-ylmethyl-SO₃H | 4-benzoylbenzyl-SO₃H (Ph-CO-) | 3-methoxybenzyl-SO₃H (MeO-) |
|---|---|---|---|---|---|---|---|
| H-AQKLRASD-OH | H-QKLRASD-OH | Before treatment | Target peptide ratio (%) | 95.4 | 95.8 | 95.8 | 96.0 |
| | | Solid obtained after treatment | Target peptide ratio (%) | 95.7 | 96.8 | 96.6 | 96.4 |
| | | | Increased point of target peptide ratio (%) | 0.3 | 1.0 | 0.8 | 0.4 |
| | H-AQKLRSD-OH | Before treatment | Target peptide ratio (%) | 98.7 | 95.7 | 95.8 | 95.4 |
| | | Solid obtained after treatment | Target peptide ratio (%) | 99.4 | 97.8 | 97.6 | 97.0 |
| | | | Increased point of target peptide ratio (%) | 0.7 | 2.1 | 1.7 | 1.6 |

TABLE 48

| Target peptide | Analogue peptide | | | 3-phenylpropyl-SO₃H | naphthalen-2-ylmethyl-SO₃H | 4-hydroxybenzene-SO₃H | 4-carboxybenzyl-SO₃H |
|---|---|---|---|---|---|---|---|
| H-YERAKSNM-OH | H-YERASNM-OH | Before treatment | Target peptide ratio (%) | 89.0 | 89.6 | 89.7 | 96.0 |
| | | Solid obtained after treatment | Target peptide ratio (%) | 91.5 | 91.4 | 91.3 | 96.4 |
| | | | Increased point of target peptide ratio (%) | 2.5 | 1.8 | 1.6 | 0.4 |
| | H-YERAKNM-OH | Before treatment | Target peptide ratio (%) | 93.3 | 92.9 | 92.6 | 95.4 |
| | | Solid obtained after treatment | Target peptide ratio (%) | 95.4 | 95.4 | 95.2 | 97.0 |
| | | | Increased point of target peptide ratio (%) | 2.1 | 2.5 | 2.6 | 1.6 |

TABLE 49

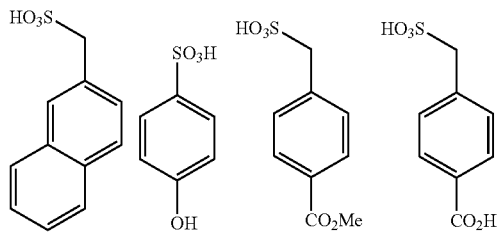

| Target peptide | Analogue peptide | | | HO₃S-naphthyl-CH₂ | SO₃H-phenyl-OH | HO₃S-CH₂-phenyl-CO₂Me | HO₃S-CH₂-phenyl-CO₂H |
|---|---|---|---|---|---|---|---|
| H-YERAKSNM-OH | H-YERASNM-OH | Before treatment | Target peptide ratio (%) | 88.1 | 88.8 | 90.1 | 88.6 |
| | | Solid obtained after treatment | Target peptide ratio (%) | 90.4 | 90.4 | 93.8 | 90.3 |
| | | | Increased point of target peptide ratio (%) | 2.3 | 1.6 | 3.7 | 1.7 |
| | H-YERAKNM-OH | Before treatment | Target peptide ratio (%) | 92.5 | 92.5 | 93.6 | 93.2 |
| | | Solid obtained after treatment | Target peptide ratio (%) | 96.3 | 95.0 | 96.5 | 95.0 |
| | | | Increased point of target peptide ratio (%) | 3.8 | 2.5 | 2.9 | 1.8 |
| | H-YERAKSN-OH | Before treatment | Target peptide ratio (%) | 87.7 | 88.5 | 89.2 | 89.3 |
| | | Solid obtained after treatment | Target peptide ratio (%) | 90.0 | 91.5 | 97.4 | 94.2 |
| | | | Increased point of target peptide ratio (%) | 2.3 | 3.0 | 8.2 | 4.9 |

As shown in Tables 47 to 49, the target peptide ratios in the obtained solid were increased, and the sulfonic acid compounds showed excellent effects in the purification of various target peptides.

INDUSTRIAL APPLICABILITY

The methods of the present application can be used to purify peptides.

The invention claimed is:

1. A method for purifying a target peptide from a peptide product obtained through a peptide synthesis, wherein the target peptide is free at the N-terminus and/or comprises at least one basic amino acid residue, the method comprising:
   (1) mixing the peptide product with a solvent in the presence of a sulfonic acid compound to provide a solid;
   (2) performing a solid-liquid separation to collect the solid.

2. The method of claim 1, wherein the sulfonic acid compound is of formula (I):

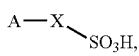

(I)

wherein
A is an optionally substituted $C_{6-10}$ aryl, an optionally substituted bicyclic heterocyclic group, $C_{2-3}$ alkenyl, or $C_{2-3}$ alkynyl;
X is
(i) a single bond,
(ii) an optionally substituted $C_{1-4}$ alkylene,
(iii) —CO—$(CH_2)_n$— wherein the CO binds to the A, or
(iv) $C_{2-4}$ alkenylene; and
n is an integer in a range of from 1 to 3.

3. The method of claim 2, wherein
A is $C_{6-10}$ aryl which may be substituted;
X is
(i) a single bond,
(ii) an optionally substituted $C_{1-4}$ alkylene,
(iii) —CO—$(CH_2)_n$— wherein the CO binds to the A, or
(iv) $C_{2-3}$ alkenylene; and
n is an integer in a range of from 1 to 3.

4. The method of claim 2, wherein
A is an optionally substituted bicyclic heterocyclic group;
X is
(i) a single bond,
(ii) $C_{1-4}$ alkylene,
(iii) —CO—$(CH_2)_n$— wherein the CO binds to the A, or
(iv) $C_{2-3}$ alkenylene; and
n is an integer in a range of from 1 to 3.

5. The method of claim 2, wherein
A is $C_{2-3}$ alkenyl; and
X is $C_{1-4}$ alkylene.

6. The method of claim 2, wherein
A is $C_{2-3}$ alkynyl; and
X is $C_{1-4}$ alkylene.

7. The method of claim 1, wherein the target peptide has 5 to 31 amino acid residues.

8. The method of claim 1, wherein the peptide product comprises a peptide analog.

9. The method of claim 8, wherein the molar ratio of the peptide analog to the target peptide is 0.7 or less in the peptide product.

10. The method of claim 1, wherein the peptide synthesis is a solid phase peptide synthesis.

11. The method of claim 1, wherein the target peptide comprises a basic amino acid residue and is optionally free at the N-terminus.

12. The method of claim 2, wherein A is a $C_{6-10}$ aryl optionally comprising 1 to 5 substituents independently selected from the group consisting of $C_{1-4}$ alkyl, —CO—$C_{6-10}$ aryl, —OH, —O—$C_{1-3}$ alkyl, —$NO_2$, —$CO_2H$, —$CO_2$—$C_{1-4}$ alkyl, halogen, —$NH_2$, —$CH_2$—$SO_3H$, —$SO_3H$, —CN, —CO—$C_{1-4}$ alkyl, —$CF_3$, and $C_{6-10}$ aryl.

13. The method of claim 2, wherein A is a $C_{6-10}$ aryl selected from the group consisting of phenyl, naphthyl, and indanyl,
wherein the $C_{6-10}$ aryl is optionally substituted with 1 to 5 substituents independently selected from the group consisting of $C_{1-4}$ alkyl, —CO—$C_{6-10}$ aryl, —OH, —O—$C_{1-3}$ alkyl, —$NO_2$, —$CO_2H$, —$CO_2$—$C_{1-4}$ alkyl, halogen, —$NH_2$, —$CH_2$—$SO_3H$, —$SO_3H$, —CN, —CO—$C_{1-4}$ alkyl, —$CF_3$, and $C_{6-10}$ aryl.

14. The method of claim 2, wherein A is an optionally substituted bicyclic heterocyclic group selected from the group consisting of 2,3,4,5-tetrahydro-1H-1-benzazepinyl, benzoxanyl, indolinyl, isoindolinyl, phthalazinyl, chromanyl, benzofuranyl, benzothiophenyl, pyrimidinyl, benzothiazolyl, quinolyl, isochromanyl, and benzotriazolyl.

15. The method of claim 2, wherein A is a bicyclic heterocyclic group optionally substituted with 1 to 5 substituents independently selected from the group consisting of $C_{6-10}$ aryl, $C_{1-4}$ alkyl, —CO—$C_{6-10}$ aryl, —OH, —O—$C_{1-3}$ alkyl, —$NO_2$, —$CO_2H$, —$CO_2$—$C_{1-4}$ alkyl, halogen, —$NH_2$, —$CH_2$—$SO_3H$, —$SO_3H$, —CN, —CO—$C_{1-4}$ alkyl, —$CF_3$, and oxo.

16. The method of claim 2, wherein A is

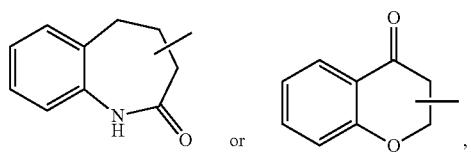

optionally substituted with one phenyl group.

17. The method of claim 2, wherein X is
(i) a single bond,
(ii) $C_{1-4}$ alkylene optionally substituted with one methyl group, one benzyl group, or one phenyl group, or
(iii) —CO—$CH_2$— wherein the CO binds to the A.

18. The method of claim 12, wherein X is
(i) a single bond,
(ii) $C_{1-4}$ alkylene optionally substituted with one methyl group, one benzyl group, or one phenyl group, or
(iii) —CO—($CH_2$)— wherein the CO binds to the A.

19. The method of claim 2, wherein X is a single bond.

20. The method of claim 16, wherein X is a single bond.

21. The method of claim 1, wherein the sulfonic acid compound is:

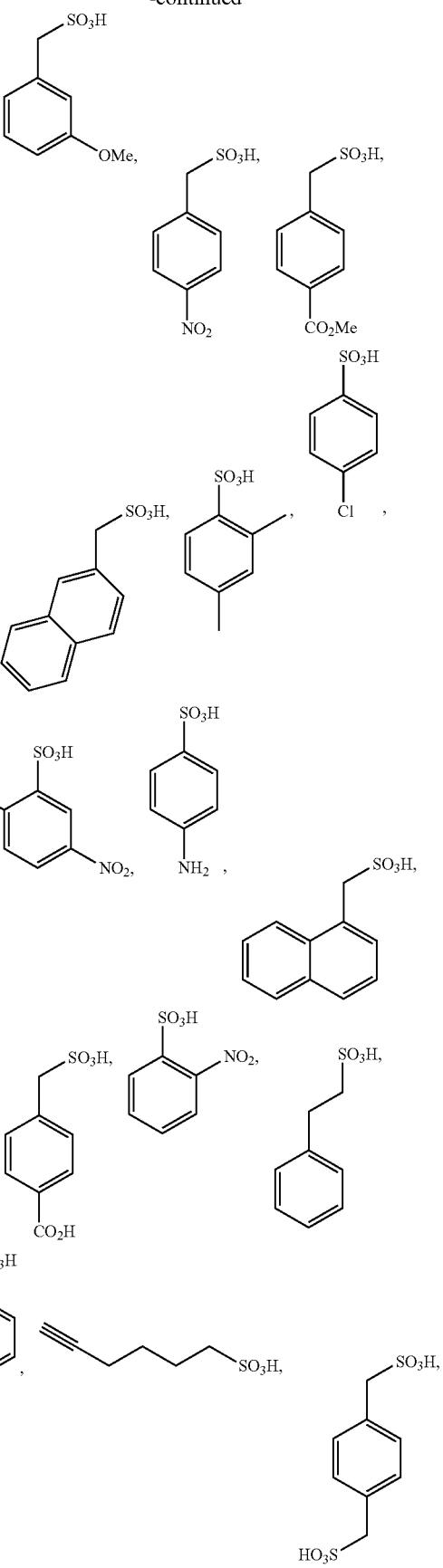

-continued
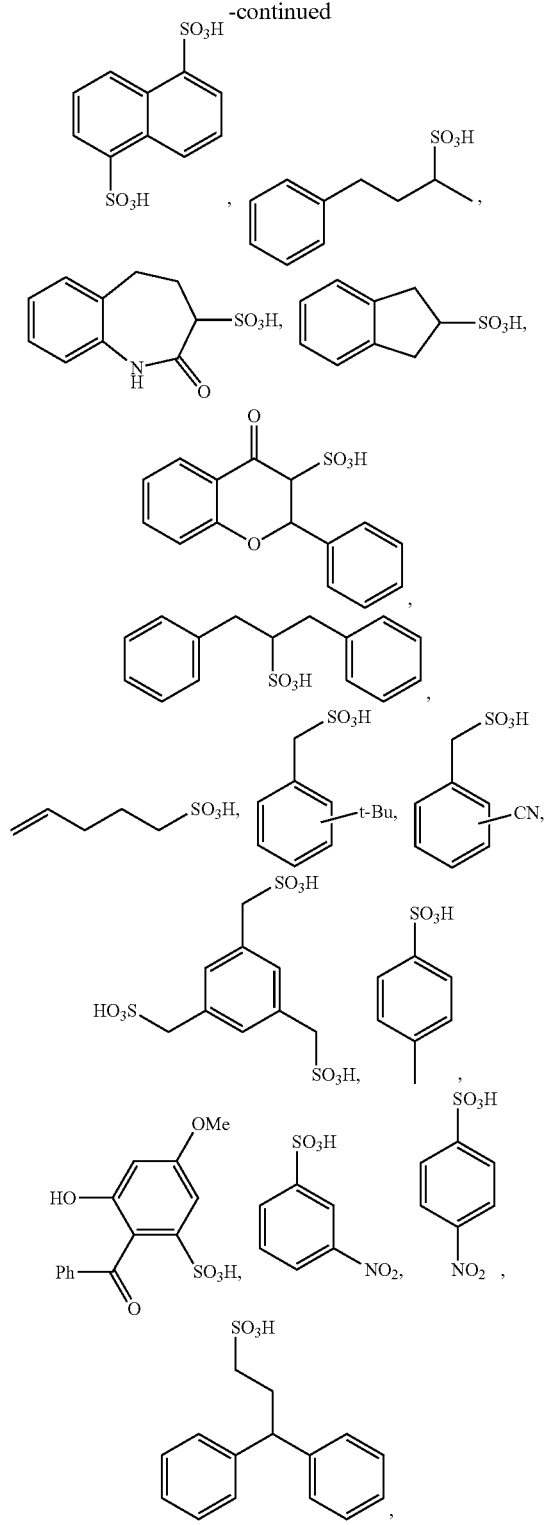
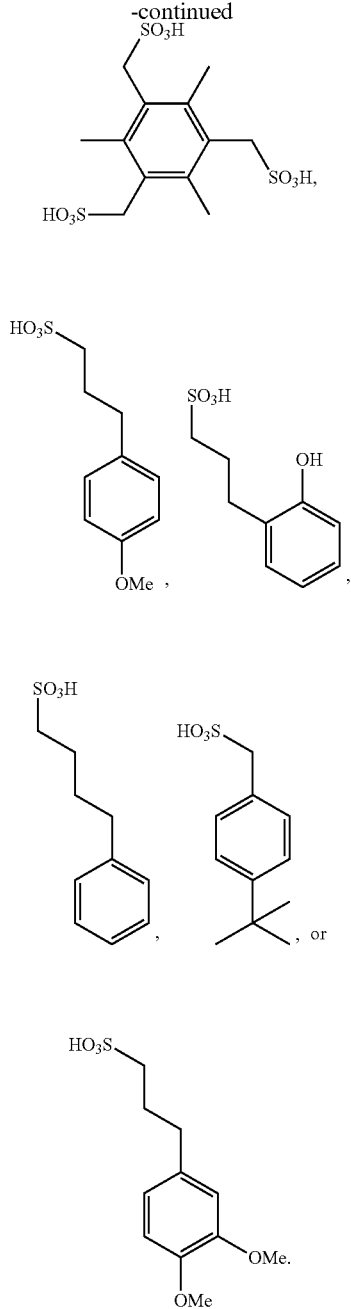
22. The method of claim 1, further comprising: removing the sulfonic acid compound.
23. The method of claim 1, wherein the method increases the molar ratio of the target peptide to an peptide analog.
24. A method for producing the target peptide, comprising the method of claim 1.
* * * * *